(12) United States Patent
Willbold et al.

(10) Patent No.: US 11,175,288 B2
(45) Date of Patent: Nov. 16, 2021

(54) METHOD FOR DETECTING INDICATORS FOR DETERMINING DISEASES

(71) Applicant: FORSCHUNGSZENTRUM JUELICH GMBH, Juelich (DE)

(72) Inventors: Dieter Willbold, Juelich (DE); Susanne Aileen Funke, Sonnefeld (DE); Eva Birkmann, Duesseldorf (DE); Kateryna Kravchenko, Essen (DE); Oliver Bannach, Duesseldorf (DE); Carsten Korth, Duesseldorf (DE); Verian Bader, Recklinghausen (DE); Steffen Huebinger, Duesseldorf (DE)

(73) Assignee: FORSCHUNGSZENTRUM JUELICH GMBH, Juelich (DE)

(*) Notice: Subject to any disclaimer, the term of this patent is extended or adjusted under 35 U.S.C. 154(b) by 0 days.

(21) Appl. No.: 14/900,361

(22) PCT Filed: Jun. 25, 2014

(86) PCT No.: PCT/EP2014/063418
§ 371 (c)(1),
(2) Date: Dec. 21, 2015

(87) PCT Pub. No.: WO2014/207049
PCT Pub. Date: Dec. 31, 2014

(65) Prior Publication Data
US 2016/0161481 A1 Jun. 9, 2016

(30) Foreign Application Priority Data
Jun. 26, 2013 (DE) .................. 102013106713.1

(51) Int. Cl.
*G01N 33/68* (2006.01)
*C07K 14/47* (2006.01)
*G01N 33/543* (2006.01)
*G01N 21/64* (2006.01)
*G01N 33/564* (2006.01)

(52) U.S. Cl.
CPC ........ *G01N 33/564* (2013.01); *C07K 14/4711* (2013.01); *G01N 33/54313* (2013.01); *G01N 33/6896* (2013.01); *G01N 21/6456* (2013.01); *G01N 21/6458* (2013.01); *G01N 2333/4703* (2013.01); *G01N 2333/4709* (2013.01); *G01N 2333/936* (2013.01); *G01N 2800/302* (2013.01)

(58) Field of Classification Search
CPC ..... G01N 2800/302; G01N 2800/2814; G01N 2800/2821; G01N 2800/2835; G01N 2333/4709; G01N 33/54313; G01N 33/6896
See application file for complete search history.

(56) References Cited

U.S. PATENT DOCUMENTS

| | | | | |
|---|---|---|---|---|
| 6,515,289 | B1* | 2/2003 | Kask | G01N 21/6408 250/459.1 |
| 2008/0220449 | A1* | 9/2008 | Vasan | C07K 16/18 435/7.9 |
| 2009/0042211 | A1* | 2/2009 | Birkmann | B01D 15/3804 435/7.1 |
| 2009/0176258 | A1 | 7/2009 | Latza | |
| 2010/0009388 | A1 | 1/2010 | An et al. | |
| 2015/0024512 | A1 | 1/2015 | Willbold et al. | |
| 2015/0037826 | A1 | 2/2015 | Willbold et al. | |

FOREIGN PATENT DOCUMENTS

| | | |
|---|---|---|
| DE | 102006010647 A1 | 9/2007 |
| DE | 102011057021 A1 | 6/2013 |
| JP | 2008-530578 A | 8/2008 |
| NO | 2013092952 A1 | 6/2013 |
| WO | 2005018424 A1 | 3/2005 |
| WO | 2007126473 A2 | 11/2007 |
| WO | 2008070229 A2 | 6/2008 |
| WO | 2010003227 A1 | 1/2010 |
| WO | 2013092951 A2 | 6/2013 |

OTHER PUBLICATIONS

Kasai T et al. Utilization of a multiple antigenic peptide as a calibration standard in the BAN50 single antibody sandwich ELISA for Abeta oligomers. Biochem. Biophys. Res. Comm. Jun. 8, 2012, 422:375-380.*

Kuhbach Ketal. Application of an amyloid beta oligomer standard in the sFIDA assay. Front. Neurosci. Jan. 2016, 10(8): 1-6. (Year: 2016).*

Sasaki D and Mitchell RA. How to obtain reproducible quantitative ELISA results. Oxford Biomedical Research. 11 pages. Retrieved from www.oxfordbiomed.com. (Year: 2001).*

Bannach O et al. Detection of prion protein particles in blood plasma of scrapie infected sheep. PLoS ONE, 7(5): e36620. (Year: 2012).*

Meso Scale Diagnostics (MSD) Technology Platform brochure, copyright 2011-2013, 16 pages total, retrieved from internet from www.mesoscale.com on Apr. 1, 2019; (Year: 2013).*

(Continued)

*Primary Examiner* — Kimberly Ballard
(74) *Attorney, Agent, or Firm* — Abel Schillinger, LLP

(57) ABSTRACT

The invention concerns a method for detecting indicators for determining diseases (disease indicators), in which aggregates of misfolded proteins play a role, and a method for selective quantitation and/or characterization of these disease indicators.

10 Claims, 6 Drawing Sheets
Specification includes a Sequence Listing.

(56) References Cited

OTHER PUBLICATIONS

Sierks MR et al. CSF levels of oligomeric alpha-synuclein and beta-amyloid as biomarkers for neurodegenerative disease. Integr Biol (Camb). 3(12):1188-1196. (Year: 2011).*

Birkmann E et al. Counting of single prion particles bound to a capture-antibody surface (surface-FIDA). Veterinary Microbiology, 123 (2007) 294-304. (Year: 2007).*

Kask P et al. Fluorescence-intensity distribution analysis and its application in biomolecular detection technology. PNAS, 1999, 96(24), 13756-13761. (Year: 1999).*

Haupts U et al. Single-molecule detection technologies in miniaturized high-throughput screening: Fluorescence intensity distribution analysis. J. Biomolecular Screening, 2003, 8(1), 19-33. (Year: 2003).*

Funke et al: "Single particle detection of Abeta aggregates associated with Alzheimer's disease" Biochemical and Biophysical Research Communications, Academic Press Inc. Orlando, FL, US, vol. 364, No. 4, pp. 902-907, Oct. 24, 2007.

Susanne Aileen Funke et al: "An Ultrasensitive Assay for Diagnosis of Alzheimer's Disease" Rejuvenation Research, vol. 11, No. 2, pp. 315-318, Apr. 1, 2008.

Susanne Aileen Funke et al: "Single-Particle Detection System for Ab Aggregates: Adaptation of Surface-Fluorescence Intensity Distribution Analysis to Laser Scanning Microscopy", Rejuvenation Research, vol. 13, No. 2-3, pp. 206-209, Dec. 4, 2009.

Wang-Dietrich: "The amyloid-beta oligomer count in cerebrospinal fluid is a biomarker for Alzheimer's disease" Journal of Alzheimer's Disease, vol. 34, pp. 985-994, Jan. 11, 2013.

Pilar Infiesta et al: "Development of an assay to measure tau oligomer levels in AD", 42nd Annual Meeting of the Society-for-Neuroscience; New Orleans. LA, USA, Oct. 17, 2012.

Jucker and Walker, Ann Neurol. 70, pp. 532-540, 2011.

Spillantini and Goedert, "Tau pathology and Neurodegeneration", Lancet Neurology 12, pp. 609-622, 2013.

Mackenzie et al., "Nomenclature and nosology for neuropathologic subtypes of frontotemporal lobar degeneration" an update, Acta Neuropathol 119, pp. 1-4, 2010.

Blennow et al., "The Neuropathology and Neurobiology of Traumatic Brain Injury", Neuron 76, pp. 886-899, Dec. 6, 2012.

Blokhuis et al., "Protein aggregation in amyotrophic lateral sclerosis", Acta Neuropathol 125, pp. 777-794, 2013.

C. A. Lemere et al., "Developing novel immunogens for a safe and effective Alzheimer's disease vaccine", Prog. Brain Res., vol. 175 (Feb. 2010) pp. 83-93.

Janissen et al., Colloids Surf B Biointerfaces, 2009, 71 (2), pp. 200-207.

S. Hübinger et al.: "Detection of [alpha]-Synclein [ . . . ]", Rejuvenation Research, Bd. 15, Nr. 2, 1. Apr. 2012 (Apr. 1, 2012), pp. 213-216.

Tokuda et al.: "Detection of elevated levels of [ . . . ]", Neurology, Lippincott Williams & Wilkins, Philadelphia, US, vol. 75, No. 20, Nov. 1, 2010 (Nov. 1, 2010), pp. 1766-1772.

Volles et al.: "Relationships between the Sequence of [ . . . ]", Journal of Molecular Bio, Academic Press, United Kingdom, vol. 366, No. 5, Feb. 9, 2007 (Feb. 9, 2007), pp. 1510-1522.

* cited by examiner

METHOD FOR DETECTING INDICATORS FOR DETERMINING DISEASES

BACKGROUND OF THE INVENTION

1. Field of the Invention

The invention concerns a method for detecting indicators for determining diseases (disease indicators), in which aggregates of misfolded proteins play a role, and a method for selective quantitation and/or characterization of these disease indicators.

2. Discussion of Background Information

Pathological aggregates of endogenous proteins, such as oligomers or fibrils, occur in many neurodegenerative diseases.

Amyloidoses are diseases characterized by extracellular deposits of insoluble, misfolded proteins. These aggregates are usually present in the form of fibers referred to as beta fibrils. The term amyloid (=starchlike) is derived from the common spectrophotometric characteristics of Congo red-stained fibrils and starch. The amyloidoses can be of both hereditary and spontaneous etiology. Some amyloidoses also present as secondary diseases.

In Alzheimer's disease (AD, Alzheimer's dementia, Latin=Alzheimer's disease), Aβ aggregates occur. As does Parkinson's disease, AD belongs to a heterogeneous group of clinical conditions whose common criteria, in many cases (but not exclusively), are extracellular, systemic or local deposits of a respective specific protein, usually in the form of conformations rich in β-pleated sheets.

However, the amyloid-beta peptide deposits (or peptide fibrils) are only the end stage of a process. The main pathological features of AD are the formation of senile or amyloid plaques consisting of the Aβ peptide, and additional neurofibrillary deposits of the tau protein. The precursor protein of the Aβ peptides, APP, is localized in the cell wall of neurons. As a result of proteolytic degradation and subsequent modification this protein gives rise to Aβ fragments of differing length and type such as Aβ 1-40, Aβ 1-42 or pGluAβ 3-42. Monomeric Aβ peptides are also produced throughout life in the healthy organism.

According to the amyloid cascade hypothesis of the 1990s, disease symptoms are triggered by Aβ deposits in the shape of plaques, but in recent years, different studies have indicated that small, freely-diffusing Aβ oligomers in particular show the highest toxicity of all Aβ species and are responsible for the occurrence and progression of AD. Aggregates of Aβ peptide are therefore directly involved in the pathogenesis of AD and may be suitable for use as biomarkers for AD (Wang-Dietrich et al., J. Alzheimer's Disease 34, 2013, 985-994). Corroboration of the diagnosis using a further routine procedure would of course be helpful, particularly for differentiation from other diseases based on endogenous misfolded proteins.

Protein aggregates are further mentioned in WO 2005/018424 A1, WO 2008/070229 A2, DE 10 2006 010 647 A1, Bannach et al. (Plosone, May 2012, Vol. 7, issue 5, e36620), WO 2010/003227 A1, DE 10 2011 057 021 A1 and WO 2013/092952 A2 (published 27 Jun. 2013).

AA amyloidosis is an extremely rare secondary complication of chronic inflammatory bowel diseases such as ulcerative colitis and Crohn's disease. In the preponderantly male patients, the kidneys, gastrointestinal tract, spleen, liver, pancreas and heart are affected (in descending frequency). AA amyloidosis manifests itself within 10 to 20 years after the onset of the primary disease. The clinical symptoms include nephrotic symptoms, proteinuria or cardiomyopathy. Systemic AA amyloidosis also affects nerve cells. A series of drugs are used to treat AA amyloidosis, including alkylating agents, methotrexate, TNF-α inhibitors, etc. Dialysis or renal transplantation may also be conducted in the case of terminal renal insufficiency. The main therapeutic goal, however, is to inhibit the synthesis of serum amyloid A precursor protein.

AL amyloidosis can present systemically or in locally limited form. It is caused by a clonal plasma cell disorder. In this disease, amyloidogenic light chains are produced, which form fibrils and are deposited in the interstitium of different organs. Most commonly affected are the kidneys, heart, intestines, liver and autonomous nervous system. The occurrence of polyneuropathy is also typical.

AApoAI is a proteinous component of high-density lipoprotein (HDL), which has the natural function of transporting water-insoluble cholesterol and phospholipids in the blood. A mutation in the N-terminal region gives AApoAI amyloidogenic properties. Hereditary AApoAI amyloidosis manifests itself in polyneuropathy of the feet and hands. This also affects the kidneys, heart, liver (elevated AP and γ-GT), peripheral nervous system, skin, larynx and testicles, in decreasing frequency.

AApoAII is a proteinous component of high-density lipoprotein (HDL), which has the natural function of transporting water-insoluble cholesterol and phospholipids in the blood. A mutation of the stop codon of the ApoAII gene gives AApoAII amyloidogenic properties. Hereditary AApoAII amyloidosis manifests itself predominantly in kidneys and heart.

ATTR amyloidosis is the most commonly-occurring hereditary amyloidosis. It is transmitted by autosomal dominant inheritance. It is attributable to a mutation of the gene for transthyretin, a transport protein that is associated with ritinol-binding protein and thyroxine in the plasma. The most common mutation, Val30Met, imparts to the protein amyloidogenic and thus pathogenic properties. In the course of ATTR amyloidosis, amyloid deposits occur in the peripheral and autonomic nervous system. The main symptoms include erectile dysfunction, gastrointestinal disorders, malabsorption and restrictive cardiomyopathy. If it is left untreated, the prognosis of ATTR amyloidosis is poor. Other than symptomatic treatment, the only remaining therapeutic option is liver transplantation.

Up to now, all diseases in clinical psychiatry, including schizophrenia or depression, have been diagnosed by purely clinical methods, in the form of an interview using a questionnaire, and if applicable, movement or behavioral tests. Because knowledge of the biological basis of mental diseases is lacking, no blood or CSF-based diagnostic tests such as those used for example in neurologic diseases, are available to corroborate the clinical diagnosis.

This situation is considered by the pharmaceutical research industry to be particularly unsatisfactory, because the lack of objective and unequivocally quantifiable tests ultimately prevents quantitative monitoring of potentially effect therapies.

The discovery of causally acting disease genes such as DISC1 has now made it possible for the first time to develop a biological diagnostic method. In a subgroup of chronic neurologic diseases such as schizophrenia and recurrent depression, DISC1 causes the development of submicroscopic protein aggregates in the brain. Using specially developed antibodies, these aggregates can be detected in the postmortem brain.

ALS is a chronic, rapidly progressing disease of the central nervous system. It primarily affects the deliberate control of the skeletal muscles. In the course of the disease, the motor neurons responsible for muscle movement degenerate. This causes severe impairment, and even complete loss, of body movements and reflexes. The average life expectancy after onset of the initial symptoms is only three years. Various etiologies have been described for ALS. The most common form of ALS is the sporadic in nature. However, there are also cases of familial hereditary ALS. What most commonly occurs in this disease is a mutation of superoxide dismutase 1 (SOD1). Recent data suggest that a hexanucleotide expansion of the gene C9orf72 causes both ALS and frontotemporal dementia.

The diagnosis of ALS may not be made until late in the course of the disease. As a rule, the diagnostic delay is one year after the onset of the first symptoms. The diagnosis of ALS currently includes a clinical appraisal, an electrophysiological examination (electromyography) and a neuropathological analysis (biopsy). A CSF tap and differential blood count can also be taken. Finally, ALS must be diagnostically differentiated from other diseases.

The pathological features of ALS include cytoplasmic inclusions of the protein FUS. In cell degeneration, these aggregates are released and can thus reach the peripheral circulation, where they can be detected for diagnosis. Other neurodegenerative diseases also show deposits of FUS aggregates, including frontotemporal lobar degeneration (FTLD), the main symptoms of which are changes in personality, social behavior, and language skills.

An alternative pathological feature of ALS are deposits of the protein SOD1 in the motor neurons. On cell degeneration, these aggregates are released and can thus reach the peripheral circulation, where they can be detected for diagnosis.

An alternative pathological feature of ALS are cytoplasmic inclusions of the ubiquinated protein TDP-43. On cell degeneration, these aggregates are released and can thus reach the peripheral circulation, where they can be detected for diagnosis.

Other neurodegenerative diseases are also associated with deposits of TDP-43 aggregates, including frontotemporal lobar degeneration (FTLD), whose main symptoms are changes in personality, social behavior and language skills. Recent studies have also indicated a connection between TDP-43-deposits and chronic Traumatic encephalopathy (CTE). CTE primarily occurs in competitive athletes and soldiers who suffer repeated craniocerebral trauma.

In diabetes mellitus type II (DMT2), aggregated endogenous proteins also play a role. For example, plaques are found in the pancreas of DMT2 that consist predominantly of islet amyloid polypeptide (IAPP). IAPP is a peptide hormone secreted in the pancreatic beta cells and secreted together with insulin. It is speculated that aggregation of IAPP plays a role in the progressive loss of islet beta cells.

There are currently no ex vivo detection systems in routine use for IAPP oligomers or aggregates in tissues or body fluids.

Parkinson's disease is a degenerative neurologic disease. The main symptoms include muscle stiffness, slowed movement, muscle tremors, and postural instability. Facultative accompanying symptoms, such as psychological disorders, have also been described. In the course of the disease, dopamine-producing neurons in the substantia nigra die off. Histopathologically, the brain tissues of Parkinson's patients show cytoplasmic inclusions, referred to as Lewy bodies, that are predominantly composed of α-synuclein, ubiquitin and other protein deposits.

Tauopathies are a group of neurodegenerative diseases characterized by accumulation of tau proteins in the brain. Hyperphosphorylation can cause the microtubule-associated tau to be converted into insoluble aggregates referred to as neurofibrillary bundles. The tauopathies include various diseases such as Alzheimer's disease, corticobasal degeneration, argyrophilic grain disease, Pick's disease, FTLD-MAPT (formerly FTDP-17, frontotemporal dementia and parkinsonism of chromosome 17), progressive supranuclear palsy, neurofibrillary tangle dementia, tauopathy with glial inclusions, as well as unclassifiable tauopathies. Recent studies also include chronic traumatic encephalopathy under the tauopathies. Some of the aforementioned diseases, such as FTLD-MAPT, are hereditary. However, the causes of most tauopathies remain unknown.

The clinical presentation of the tauopathies is highly multifaceted, comprising motor disorders (L-dopa sensitive or atypical Parkinson's syndrome, akinesia with "freezing," supranuclear palsy, and even corticobasal syndromes), behavioral and speech disorders, and psychiatric symptoms such as aggressiveness, psychotic states and depression.

Huntington's disease is a genetic neurodegenerative disease that affects muscle coordination and leads to reduced cognitive capacity and psychiatric problems. The disease strikes both men and women and is transmitted via an autosomal dominant mutation of the huntingtin gene. An expansion of a CAG triplet repeat leads to lengthening of the polyglutamine tract in the matured protein, causing it to have a stronger tendency toward misfolding and aggregation.

Familial visceral amyloidosis is caused by a mutation of the gene for lysozyme that imparts to the matured protein amyloidogenic properties. Amyloid deposits are seen systemically in numerous organs.

Disease indicators, i.e. indicators for the detection of diseases, also referred to as biomarkers, have always been used for the diagnosis of diseases. Known examples of biomarkers include urine glucose content as an indicator of diabetes mellitus or urine HCG content in pregnancy tests.

In order to provide medical care for a constantly increasing and aging population, the identification of new, specific biomarkers that ensure a definite diagnosis is needed. High specificity is needed in particular in diseases with similar symptoms and clinical features in order to allow promising treatment to be carried out. Disease indicators should also identify persons at risk as soon as possible in an early disease stage or in the case of a recurrence. The biomarkers should be present in easily accessible biomaterial, be identifiable, and allow rapid detection. This makes it possible to follow not only the course of the disease, but also the effect of treatment and disease prevention.

The object of the present invention was to provide such biomarkers, particularly for diseases that exhibit aggregates of misfolded proteins.

A further object was to provide a rapid and safe method for the selective quantitation and/or characterization thereof. In particular, the disease indicators should be suitable for routine clinical use. This means that they can be characterized in a test, preferably a rapid test, and optionally by means of standards, so that comparable and independent values are determined.

Moreover, the above-mentioned requirements for biomarkers should be fulfilled, and the corresponding improved possibilities and tools compared to the prior art should be provided.

Diagnosis of AA amyloidosis includes an assessment of the clinical presentation. In this case, however, diagnostic differentiation from numerous other diseases is problematic. Preclinically, the diagnosis can only be made by histologic detection of AA amyloid by means of Congo red staining. However, fat aspiration biopsy is required for this purpose. A routine diagnostic method for detecting amyloid protein aggregates as biomarkers in body fluids has not yet been established. AA amyloidosis is characterized by misfolding of the precursor protein serum amyloid A (AA). The AA aggregates can thus be a direct biomarker for AA amyloidosis. However, diagnostic detection is technically challenging, as AA is also produced ubiquitously throughout the healthy organism. The method must therefore be insensitive to high excess amounts of normally folded, monomeric AA.

The diagnosis of AL amyloidosis includes an assessment of the clinical presentation, which, however, can be highly variable. Moreover, diagnostic differentiation from numerous other diseases is also problematic. The gold standard is histologic detection of AL amyloid by means of Congo red staining. In addition, immunohistochemical testing should be conducted. For this purpose, however, an invasive biopsy is required. A routine diagnostic method for minimally invasive detection of amyloid protein aggregates as biomarkers in body fluids has not yet been established.

AL amyloidosis is characterized by misfolding of the IgG light chain precursor protein (AL). AL aggregates can thus be a direct biomarker for AL amyloidosis. However, diagnostic detection is technically challenging, as AL is also produced ubiquitously throughout the healthy organism. The method must therefore be insensitive to high excess amounts of normally folded, monomeric AL.

Diagnosis of AApoAI amyloidosis includes an assessment of the clinical presentation. In this case, however, diagnostic differentiation from numerous other diseases is problematic. The gold standard is histologic detection of AApoAI amyloid by means of Congo red staining. For this purpose, however, an invasive biopsy is required. A routine diagnostic method for minimally invasive detection of amyloid protein aggregates as biomarkers in body fluids has not yet been established.

AApoAI amyloidosis is characterized by misfolding of the precursor of apolipoprotein AI (AApoAI). AApoAI aggregates can thus be a direct biomarker for AApoAI amyloidosis. However, diagnostic detection is technically challenging, as AApoAI is also produced ubiquitously throughout the healthy organism. The method must therefore be insensitive to high excess amounts of normally folded, monomeric AApoAI.

Diagnosis of AApoAII amyloidosis includes an assessment of the clinical presentation. In this case, however, diagnostic differentiation from numerous other diseases is problematic. The gold standard is histologic detection of AApoAII amyloid by means of Congo red staining. For this purpose, however, an invasive biopsy is required. A routine diagnostic method for minimally invasive detection of amyloid protein aggregates as biomarkers in body fluids has not yet been established.

AApoAII amyloidosis is characterized by misfolding of the precursor of apolipoprotein AII (AApoAII). The AApoAII aggregates can thus be a direct biomarker for AApoAII amyloidosis. However, diagnostic detection is technically challenging, as AApoAII is also produced ubiquitously throughout the healthy organism. The method must therefore be insensitive to high excess amounts of normally folded, monomeric AApoAII.

The diagnosis of ATTR amyloidosis includes an assessment of the clinical presentation. In this case, however, diagnostic differentiation from numerous other diseases is problematic. In addition, there are differences in the time of the initial symptoms, course thereof and regional phenotype. The gold standard is histologic detection of ATTR amyloids by means of Congo red staining. For this purpose, however, an invasive biopsy is required. A routine diagnostic method for detecting amyloid protein aggregates as biomarkers in body fluids has not yet been established.

ATTR amyloidosis is characterized by misfolding of the precursor protein transthyretin (TTR). ATTR aggregates can thus be a direct biomarker for ATTR amyloidosis. However, diagnostic detection is technically challenging, as ATTR is also produced ubiquitously throughout the healthy organism. The method must therefore be insensitive to high excess amounts of normally folded, monomeric ATTR.

At present, schizophrenic psychoses cannot be diagnosed until three to five years after the appearance of the first symptoms. There is currently no routinely-used diagnostic method based on the detection of a biomarker for chronic neurologic diseases such as schizophrenia. For developing such a therapy, the identification and standardization of a biomarker in the early or even presymptomatic course of the disease is of immense and probably decisive importance. This also applies to genetically caused cases, because the course of the disease and its treatment can also be followed in such cases.

Characteristic for many diseases of the central nervous systems is the appearance of misfolded, aggregated proteins in the course of the disease. Recent studies have indicated a connection between chronic neurologic diseases, such as schizophrenia or recurrent depression, and aggregated DISC1 (disrupted in schizophrenia 1) protein. These DISC1 aggregates could be a direct biomarker for schizophrenia, recurrent depression and other DISC1opathies. However, diagnostic detection is technically challenging, as DISC1 is also produced in the healthy organism. The method must therefore be insensitive to high excess amounts of normally folded, monomeric DISC1.

There is currently no routinely-used diagnostic method based on the detection of a biomarker, neither for ALS nor for FTLD. There is also no causal therapy at present. Only neuroprotective and symptomatic therapies are in use. For developing such a therapy, the identification and standardization of a biomarker in the early or even presymptomatic course of the disease is of immense and probably decisive importance. This also applies to genetically caused cases, because the course of the disease and its treatment can also be followed in such cases.

Characteristic for many diseases of the central nervous systems is the appearance of misfolded, aggregated proteins in the course of the disease. In amyotrophic lateral sclerosis (ALS) and frontotemporal lobar degeneration (FTLD), cytoplasmic deposits of the RNA-binding protein FUS (fused in sarcoma) have been described. These FUS aggregates could be a direct biomarker for the diseases described. However, diagnostic detection is technically challenging, as FUS is also produced ubiquitously throughout the healthy organism. The method must therefore be insensitive to high excess amounts of normally folded, monomeric FUS.

Blood sugar level is currently considered a generally recognized biomarker for DMT2, by means of which a definite diagnosis can be achieved for patients. If blood sugar level is regulated using insulin, detection of DMT2 is no longer possible. This is particularly important in analysis of stored blood used for transfusions, as this blood may constitute a potential risk for the recipient. For developing causal therapy for DMT2, the identification and standardization of a biomarker in the early or even presymptomatic course of the disease is of immense and probably decisive importance. This also applies to genetically caused cases, because the course of the disease and its treatment can also be followed in such cases.

For many years, a connection has been reported between diabetes mellitus type 2 (DMT2) and Alzheimer's dementia (AD). According to studies, around 80% of AD patients suffer from DMT2 or show higher blood glucose levels. Mice with DMT2 and AD also show similar behavioral, cognitive, and vascular anomalies. The two diseases show similar pathological features: the occurrence of amyloid plaques in the pancreas (DMT2) or in the brain (AD) resulting from protein folding and subsequent fibril formation of the IAPP or Aβ peptide. The small aggregates in particular are considered to be the main causative agents in the occurrence and progression of DMT2 and AD. IAPP aggregates can therefore be a direct biomarker for DMT2. However, diagnostic detection is technically challenging, as IAPP is also produced ubiquitously throughout the healthy organism. The method must therefore be insensitive to high excess amounts of normally folded, monomeric IAPP.

There is currently no routinely-used diagnostic method for ALS based on the detection of a biomarker. There is also no causal therapy at present. Only neuroprotective and symptomatic therapies are in use. For developing such a therapy, the identification and standardization of a biomarker in the early or even presymptomatic course of the disease is of immense and probably decisive importance. This also applies to genetically caused cases, because the course of the disease and its treatment can also be followed in such cases.

Characteristic for many diseases of the central nervous systems is indeed the appearance of misfolded, aggregated proteins in the course of the disease. Deposits of superoxide dismutase 1 (SOD1) have been described in amyotrophic lateral sclerosis (ALS). These SOD1 aggregates could be a direct biomarker for ALS. However, diagnostic detection is technically challenging, as SOD1 is also produced ubiquitously throughout the healthy organism. The method must therefore be insensitive to high excess amounts of normally folded, monomeric SOD1.

Parkinson's disease is diagnosed by a procedure referred to as the L-dopa test. In this test, patients are given L-dopa in combination with a decarboxylase inhibitor. If this treatment brings about a clear improvement in symptoms, Parkinson's disease can be diagnosed with a high degree of certainty.

However, there is currently no routinely-used diagnostic method for Parkinson's disease based on minimally invasive detection of a biomarker in body fluids. For developing such a therapy, the identification and standardization of a biomarker in the early or even presymptomatic course of the disease is of immense and probably decisive importance. This also applies to genetically caused cases, because the course of the disease and its treatment can also be followed in such cases.

Characteristic for many diseases of the central nervous systems is indeed the appearance of misfolded, aggregated proteins in the course of the disease. Parkinson's disease is characterized by pathological accumulation of aggregated α-synuclein. These α-synuclein aggregates could be a direct biomarker for Parkinson's disease and other α-synucleinopathies. However, diagnostic detection is technically challenging, as α-synuclein is also produced in the healthy organism. The method must therefore be insensitive to high excess amounts of normally folded, monomeric α-synuclein.

The neuropathological phenotype of different tauopathies is identified post-mortem. This is made difficult by the considerably overlapping of different neurological changes. In addition, diverse pathologies are often present in combination, which underscores the need for biomarker research. There is currently no routinely-used diagnostic method for the tauopathies based on the detection of a biomarkers in body fluids. There is also no causal therapy at present. Only neuroprotective and symptomatic therapies are in use. For developing such a therapy, the identification and standardization of a biomarker in the early or even presymptomatic course of the disease is of immense and probably decisive importance. This also applies to genetically caused cases, because the course of the disease and its treatment can also be followed in such cases.

Characteristic for many diseases of the central nervous systems is indeed the appearance of misfolded, aggregated proteins in the course of the disease. Tauopathies are characterized by pathological deposits of the tau proteins. These tau aggregates could be a direct biomarker for different diseases. However, diagnostic detection is technically challenging, as tau is also produced ubiquitously throughout the healthy organism. The method must therefore be insensitive to high excess amounts of normally folded, monomeric tau.

For ALS, as well as FTLD and CTE, there is currently no routine diagnostic method in use that is based on the detection of a biomarker. There is also no causal therapy at present. Only neuroprotective and symptomatic therapies are in use. For developing such a therapy, the identification and standardization of a biomarker in the early or even presymptomatic course of the disease is of immense and probably decisive importance. This also applies to genetically caused cases, because the course of the disease and its treatment can also be followed in such cases.

Characteristic for many diseases of the central nervous systems is the appearance of misfolded, aggregated proteins in the course of the disease. In amyotrophic lateral sclerosis (ALS) and frontotemporal lobar degeneration (FTLD), deposits of TAR DNA binding protein 43 (TDP-43) have been described. These TDP-43 aggregates could be a direct biomarker for the diseases described. However, diagnostic detection is technically challenging, as TDP-43 is also produced ubiquitously throughout the healthy organism. The method must therefore be insensitive to high excess amounts of normally folded, monomeric TDP-43. On suspicion of Huntington's disease, a genetic test can be conducted that reliably identifies the disease. However, there is currently no routinely-used diagnostic method for Huntington's disease based on minimally invasive detection of a biomarkers in body fluids. For developing such a therapy, the identification and standardization of a biomarker in the early or even presymptomatic course of the disease is of immense and probably decisive importance. This also applies to genetically caused Huntington's disease, because the course of the disease and its treatment can also be followed in such cases.

Characteristic for many diseases of the central nervous systems is the appearance of misfolded, aggregated proteins in the course of the disease. Huntington's disease is characterized by pathological accumulation of aggregated huntingtin. These huntingtin aggregates could be a direct biomarker for Huntington's disease. However, diagnostic detection is technically challenging, as huntingtin is also produced in the healthy organism. The method must therefore be insensitive to high excess amounts of normally folded, monomeric huntingtin.

The diagnosis of ALys amyloidosis includes an assessment of the clinical presentation. In this case, however, diagnostic differentiation from numerous other diseases is problematic. The gold standard is histologic detection of ALys amyloid by means of Congo red staining and immunohistochemistry. For this purpose, however, an invasive biopsy is required. A routine diagnostic method for minimally invasive detection of amyloid protein aggregates as biomarkers in body fluids has not yet been established.

Familial visceral amyloidosis is characterized by misfolding of the lysozyme precursor protein (ALys). ALys aggregates can thus be a direct biomarker for ALys amyloidosis. However, diagnostic detection is technically challenging, as lysozyme is also produced ubiquitously throughout the healthy organism. The method must therefore be insensitive to high excess amounts of normally folded, monomeric ALys.

It was also the object of the present invention to provide a routine procedure for quantitative determination of disease indicators, particularly several disease indicators next to one another in the same sample. The process should also provide the possibility of analyzing the sample with only a few, or preferably no process steps.

Many neurodegenerative diseases and amyloidoses are characterized by the concomitant appearance of different aggregated protein species. An example is Alzheimer's dementia, in which deposits of both amyloid beta and tau are observed (Jucker and Walker, Annals of Neurology 70, 532-540, 2011; Spillantini and Goedert, Lancet Neurology 12, 609-622, 2013, which are incorporated herein by reference). In frontotemporal lobar degeneration (FTLD), tau and TDP-43 coexist as pathological protein aggregates (Mackenzie et al., Acta Neuropathologica 119, 1-4, 2010). Moreover, TDP-43 pathology also manifests itself in amyotrophic lateral sclerosis and chronic traumatic encephalopathy (Blennow et al., Neuron 76, 886-899, 2012; Blokhuis et al., Acta Neuropathologica 125, 777-794, 2013, which are incorporated herein by reference).

The method must ensure sufficient specificity to test for different aggregate types in parallel and/or concomitantly. Therefore, another object of the invention was to provide a method with concomitant high specificity in testing for different aggregate types, and thus to exclude interference in the examination of an aggregate type by a second aggregate type. It should also be possible to test for aggregate mixed forms consisting of different protein monomers.

The protein aggregates of the aforementioned diseases described so far constitute only one main pathological characteristic of the respective disease. Their use as biomarkers is not established.

SUMMARY OF THE INVENTION

This object is achieved by means of a method for qualitative and/or quantitative determination of disease indicators, characterized in that a sample is tested for at least one aggregate type, and preferably at least two aggregate types of endogenous misfolded proteins, comprising the following steps:
a) application of the sample to be tested to a substrate,
b) addition of probes labeled for detection that label the respective aggregate by specifically binding to it and
c) detection of the labeled aggregates, wherein step b) can be carried out before step a) and
the disease is selected from the group composed of:
AA amyloidosis, AL amyloidosis, AApoAI amyloidosis, AApoAII amyloidosis, ATTR amyloidosis, schizophrenia and other DISC1opathies, amyotrophic lateral sclerosis, frontotemporal lobar degeneration and other FUS proteinopathies, diabetes mellitus type 2, Parkinson's disease and other synucleinopathies, tauopathies, chronic traumatic encephalopathy and other TDP-3 proteinopathies, Huntington's disease, familial visceral amyloidosis and/or Alzheimer's dementia and if Aβ aggregates were determined in the sample, the sample is tested for at least one further aggregate type of an endogenous misfolded protein.

In an embodiment, the process is characterized in that without further processing and/or treatment of the sample, after testing for a first aggregate type, testing is conducted for at least one more, e.g. a second different aggregate type of endogenous misfolded protein.

In a further embodiment, the method is characterized in that the sample is tested for at least two different aggregate types in one process step.

In a further embodiment, the method is characterized in that the sample is tested for at least two different aggregate types on the same substrate.

In a further embodiment, the process is characterized in that the aggregate-type endogenous misfolded protein is selected from the group consisting of serum amyloid A protein aggregates, IgG light chain aggregates, AapoAI aggregates, AapoAII aggregates, ATTR aggregates, DISC1 aggregates, FUS aggregates, IAPP aggregates, SOD1 aggregates, α-synuclein aggregates, tau aggregates, TDP-43 aggregates, huntingtin aggregates, lysozyme aggregates and Aβ aggregates.

In a further embodiment, the method is characterized in that the detection in step c) is carried out by means of a method with a spatially resolved signal, preferably the sFIDA-method.

In a further embodiment, the method is characterized in that before step a), capture molecules are immobilized on the substrate.

In a further embodiment, the method is characterized in that the capture molecules and/or the probe are labeled with fluorescent dyes.

In a further embodiment, the method is characterized in that the capture molecules and/or the probe have specific antibodies to an epitope of the proteins that form the aggregates.

In a further embodiment, the method is characterized in that an internal or external standard is used.

In a further embodiment, the method is characterized in that the capture molecules, probes and/or standards comprise a polymer composed of monomer sequences that are identical in sequence to a partial region of the endogenous proteins or show homology of at least 50% over the corresponding partial region, wherein these polymers do not aggregate and the endogenous proteins are those that aggregate.

Standards for selective quantitation and/or characterization of the aforementioned disease indicators containing a polymer [is used], composed of monomer sequences that are identical in sequence to a partial region of the endogenous proteins or show homology of at least 50% over the corresponding partial region, are also the subject matter of the invention, wherein these polymers do not aggregate and the endogenous proteins are those that aggregate.

The standard molecules according to the invention are used to inactivate the respective protein aggregates, for example by binding or destroying the protein aggregates, or prophylactically in order to prevent formation of the protein aggregates. Therefore, standards for use in medicine, as drugs, and/or for use in therapeutic, diagnostic and/or surgical procedures are also the subject matter of the invention.

Further subject matter is a substrate comprising precisely defined regions with capture molecules for the above-mentioned disease indicators and/or aggregates.

Further subject matter of the invention is a differential diagnosis for determining diseases exhibiting aggregates of misfolded proteins comprising the following steps:
 i) quantitative determination of disease indicators detected in the method according to the invention;
 ii) comparison of these data with the standard values;
 iii) detection of a significantly different quantity of disease indicators in this comparison;
 iv) attribution of the discrepancy to a disease selected from the group composed of AA amyloidosis, AL amyloidosis, AApoAI amyloidosis, AApoAII amyloidosis, ATTR amyloidosis, schizophrenia and other DISC1opathies, amyotrophic lateral sclerosis, frontotemporal lobar degeneration and other FUS proteinopathies, diabetes mellitus type 2, Parkinson's disease and other synucleinopathies, tauopathies, chronic traumatic encephalopathy and other TDP-43 proteinopathies, Huntington's disease, familial visceral amyloidosis and/or Alzheimer's dementia.

The term "aggregate type" is understood within the meaning of the invention to refer to an aggregate of a certain defined composition of endogenous misfolded proteins. In an alternative, an aggregate type is composed (constructed) of the same peptides (monomers), i.e. of peptides of the same amino acid sequence or different homologs of one and the same peptide. Other alternatives comprise an aggregate type composed of different peptides (monomers), i.e. of peptides having different amino acid sequences or homologs of the different peptides. Both alternatives can also be present in one sample.

In an embodiment of the present invention, "qualitative determination of disease indicators" refers to the identification of new, specific biomarkers. In other words, disease indicators are identified and newly defined. According to the invention, disease indicators are defined by the presence, optionally in a specified concentration, and/or absence of one or more aggregates of endogenous misfolded proteins respectively.

In a further embodiment, "qualitative determination of disease indicators" refers to testing for or determination of the presence and/or absence of these biomarkers.

Within the meaning of the present invention, "quantitative determination of disease indicators" refers in an first alternative to determination of the concentration of the biomarkers. In a second alternative, the composition, size and/or shape of the biomarkers is determined. It is also possible to carry out both alternatives, preferably simultaneously, in one process step.

Quantitative determination of disease indicators is equivalent to selective quantitation and/or characterization of aggregate types as biomarkers. As soon as the characteristics of a disease indicator are defined, this is followed by its quantitative determination, i.e. its selective quantitation: i.e. determination of concentration that includes the Information on presence or absence; and/or its characterization: i.e. determination of the composition, size and/or shape.

In an alternative of the present invention, a sample is tested for at least two aggregate types of endogenous misfolded proteins. In an alternative of the present invention, a sample is tested for at least three aggregate types of endogenous misfolded protein. In an alternative of the present invention, a sample is tested for at least four aggregate types of endogenous misfolded proteins. In an alternative of the present invention, a sample is tested for at least five aggregate types of endogenous misfolded proteins. In an alternative of the present invention, a sample is tested for at least six aggregate types of endogenous misfolded proteins. In an alternative of the present invention, a sample is tested for at least seven aggregate types of endogenous misfolded proteins. In an alternative of the present invention, a sample is tested for at least eight aggregate types of endogenous misfolded proteins. In an alternative of the present invention, a sample is tested for at least nine aggregate types of endogenous misfolded proteins. In an alternative of the present invention, a sample is tested for at least ten aggregate types of endogenous misfolded proteins. In an alternative of the present invention, a sample is tested for at least 11, 12, 13, 14, 15 or more aggregate types of endogenous misfolded proteins.

In an embodiment of the present invention, the aggregates are made up of peptides or monomers of SEQ ID NOs: 1-15 and/or homologs thereof allocated as follows:

Serum amyloid A protein aggregates: SEQ ID NO: 1; IgG light chain aggregates: SEQ ID NO: 2; AapoAI aggregates: SEQ ID NO: 3; AapoAII aggregates: SEQ ID NO: 4; ATTR aggregates: SEQ ID NO: 5; DISC1 aggregates: SEQ ID NO: 6; FUS aggregates: SEQ ID NO: 7; IAPP aggregates: SEQ ID NO: 8; SOD1 aggregates: SEQ ID NO: 9; α-synuclein aggregates: SEQ ID NO: 10; tau aggregates: SEQ ID NO: 11; TDP-43 aggregates: SEQ ID NO: 12; huntingtin aggregates: SEQ ID NO: 13; lysozyme aggregates: SEQ ID NO: 14 and Aβ aggregates: SEQ ID NO: 15.

In an embodiment, testing is conducted for at least one aggregate type from above-mentioned group and one further aggregate type.

However, there may also be mixed aggregates composed of at least two different proteins or monomers, referred to as aggregate mixed forms.

Within the meaning of the invention, the term "testing for aggregate type of endogenous misfolded proteins" or synonyms thereof such as "testing" refer to qualitative and/or quantitative determination (analysis) of the respective aggregate type. In qualitative determination, presence or absence is determined, while in quantitative determination, concentration, composition, size and/or shape are determined.

The term "without further processing and/or treatment" of the sample used in testing for a second aggregate type, in one alternative according to the invention, means that between two tests for different aggregate types, no processing and/or treatment of the sample takes place. In another alternative, no chemical reactions take place in the sample after testing for a first or a second aggregate type. Preferably, the first and second, and optionally every further test takes place in a sample aliquot. Optionally, the sample can be subjected only to physical or mechanical effects such as temperature change or pipetting. In a further or additional alternative, the sample is not subjected to any physical or mechanical effects. In a further or additional alternative, the sample used in testing for a second aggregate type has the same chemical composition as the sample used in testing for the first aggregate type, but the same compounds are optionally present in changed concentrations. Moreover, the sample used in testing for a second aggregate type optionally contains the capture molecules, probes and/or standards used in testing for the first aggregate type, and optionally the corresponding compounds of an aggregate, capture molecule and/or probe. In a further or additional alternative, the probes used in testing for a second aggregate type are added only after testing for the first aggregate type, so that the only chemical reaction is binding of the specific probe for the second aggregate type to said aggregate, provided it is contained in the sample.

The circumstances described above apply analogously to testing for a third, fourth, fifth, sixth, seventh, eighth, ninth, tenth and/or further aggregate type.

In an embodiment, the invention concerns a method for detecting indicators for determining diseases that exhibit aggregates of misfolded proteins comprising the following steps:
 a) application of the sample to be tested to a substrate,
 b) addition of probes labeled for detection that label the respective aggregate by specifically binding to it and
 c) detection of the labeled aggregates,
 wherein step b) can be carried out before step a) and
 the disease is selected from the group composed of AA amyloidosis, AL amyloidosis, AApoAI amyloidosis, AApoAII amyloidosis, ATTR amyloidosis, schizophrenia and other DISC1opathies, amyotrophic lateral sclerosis, frontotemporal lobar degeneration and other FUS proteinopathies, diabetes mellitus type 2, Parkinson's disease and other synucleinopathies, tauopathies, chronic traumatic encephalopathy and other TDP-43 proteinopathies, Huntington's disease and/or familial visceral amyloidosis.

In accordance with the definition of the NIH, the biomarkers according to the invention, also referred to as disease indicators, are parameters by means of which a property can be objectively measured in order to use it as an indicator for normal biological pathogenic processes or therapeutic responses to a therapeutic Intervention. The disease inhibitors determined and used according to the invention are qualitatively and quantitatively characterized by means of a physical and/or chemical method.

Aggregates within the meaning of the present invention are
 particles consisting of several, preferably identical components that are not covalently bonded to one another and/or
 non-covalent agglomerations of several monomers and heteroaggregates, "coaggregates," i.e. aggregates of different monomers.

For the method according to the invention, samples are taken from the human or animal body and are not returned to said body.

In an alternative of the method, samples containing the potential biomarkers are compared with samples from healthy individuals and/or those diagnosed with a disease for detection, and in particular qualitative determination, of disease indicators. This diagnosis is based e.g. on an appraisal of the clinical presentation or evaluation of other diagnostic procedures. By comparing the amount of aggregates detected, it is possible to assess their suitability as biomarkers.

In an alternative, disease indicators suitable for routine clinical use are provided. According to the invention, biomarkers are suitable for routine clinical use, provided that there is scientifically verifiable and reproducible evidence to this effect, particularly based on physical and/or chemical methods.

A method for selective quantitation and/or characterization of the disease indicators comprising the following steps:
 a) application of the sample to be tested to a substrate,
 b) addition of probes labeled for detection that label the respective aggregate by specifically binding to it and
 c) detection of the labeled aggregates,
 wherein step b) can be carried out before step a) and
 the disease is selected from the group composed of:
 AA amyloidosis, AL amyloidosis, AApoAI amyloidosis, AApoAII amyloidosis, ATTR amyloidosis, schizophrenia and other DISC1opathies, amyotrophic lateral sclerosis, frontotemporal lobar degeneration and other FUS proteinopathies, diabetes mellitus type 2, Parkinson's disease and other synucleinopathies, tauopathies, chronic traumatic encephalopathy and other TD P-43 proteinopathies, Huntington's disease and/or familial visceral amyloidosis, is also the subject matter of the invention.

A method for determining the composition, size and/or shape of aggregates is therefore also the subject matter of the present invention. In this case, the process steps mentioned and described above are used.

In a variant of the present invention, the sample is pretreated, preferably according to one or more of the following processes:
 heating (to a temperature up to the boiling point of the sample)
 one or more freezing-thawing cycles,
 dilution with water or buffer,
 treatment with enzymes such as proteases, nucleases, lipases,
 centrifuging,
 precipitation,
 competition with probes in order to eliminate any antibodies present.

According to the invention, a material is selected as a substrate that exhibits the lowest possible nonspecific binding capacity, particularly with respect to aggregates of misfolded proteins.

In an embodiment of the present invention, a glass substrate is selected.

The substrate can be coated with hydrophilic substances, preferably poly-D-lysine, polyethylene glycol (PEG), preferably heterobiofunctional polyethylene glycol (NHS-PEG-COOH) or dextran, particularly dextran, and preferably carboxymethyldextran (CMD).

In an embodiment of the present invention, the glass surface is hydroxylated and then activated with amino groups.

In order to prepare the substrate for coating, one or more of the following steps is carried out:
 washing of a glass substrate or glass carrier in an ultrasound bath or plasma cleaner, or incubating for at least 3 hours in 5 M NaOH,
 rinsing with water and subsequent drying under nitrogen,
 Immersion in a solution of concentrated sulfuric acid and hydrogen peroxide in a 3:1 ratio for activation of the hydroxyl groups,
 rinsing with water to a neutral pH, then with ethanol and drying under a nitrogen atmosphere,
 immersion in a solution of 3-aminopropyltriethoxysilane (APTES) (1-7%) in dry toluene of a solution of ethanolamine,
 rinsing with acetone or DMSO and water and drying under a nitrogen atmosphere.

For coating with dextran, preferably carboxymethyldextran (CMD), the substrate is incubated with an aqueous solution of CMD (in a concentration of 10 mg/mL or 20 mg/mL) and optionally incubated with N-ethyl-N-(3-dimethylaminpropyl)carbodiimide (EDC) (200 mM) and N-hydroxysuccinimide (NHS) (50 mM), and then washed.

In a variant, the carboxymethyldextran is covalently bonded to the glass surface that was first hydroxylated and then activated with amine groups as described above.

Microtiter plates, preferably with glass bottoms, can also be used as a substrate. As concentrated sulfuric acid cannot be used with polystyrene frames, activation of the glass surface in a variant of the invention is carried out analogously to the method of Janissen et al. (Colloids Surf B Biointerfaces, 2009, 71 (2), 200-207).

In an embodiment of the present invention, the glass surface is incubated with sodium hydroxide solution (5 M) for 15 minutes at room temperature, rinsed three times with water, mixed with hydrochloric acid, and again incubated for 15 minutes at room temperature. After washing thee times with water and twice with ethanol, the substrate (glass surface) is dried under a nitrogen atmosphere.

In order to produce amino groups on the glass surface, this surface is incubated overnight with ethanolamine (5.6 M) at room temperature. The substrate is then washed three times with DMSO, twice with ethanol, and dried under a nitrogen atmosphere.

Heterobiofunctional polyethylene glycol (NHS-PEG-COOH, MW 3,400 Da) is dissolved to 50 mM in DMSO at 70° C. for 1 minute, cooled to room temperature, and adjusted with 2% triethylamine. Incubation with this solution is carried out for at least one hour at room temperature. The solution is removed and the glass surface is washed three times with water.

In order to activate the PEG coating, 100 mM of NHS and EDC each is dissolved in MES buffer (0.1 M, pH 5) and mixed in a 1:1 ratio to final concentrations of 50 mM respectively. The substrate is incubated with this solution for 30-60 minutes. After removal of the solution, washing is carried out three times with MES buffer (0.1 M, pH 5).

The capture antibodies are diluted to 30 ng/µL in PBS, and the substrate is incubated therewith for 1-3 hours at room temperature. The solution is then removed, and washing is carried out three times with PBST and then three times with PBS.

3% BSA was first centrifuged at 100,000 g (1 hour at 4° C.). The supernatant is incubated with the substrate for one hour at room temperature. The BSA solution is removed, and washing is carried out three times with PBST.

The sample (e.g. aggregates of recombinant protein and natural patient sample) is—if necessary—diluted in PBS and applied. The substrate with the sample is centrifuged at 1,000 g for one hour at 4° C. in a swing-out centrifuge. The supernatant is removed, and the glass surface is washed three times with PBST and three times with PBS.

Fluorescence-labeled antibodies are used as detection probes. These are diluted to 1-2 ng/µL in PBS and mixed with 1.5% BSA. The batches are centrifuged at 100,000 g for one hour at 4° C. The supernatants are applied to the substrate and incubated for 1-2 hours at room temperature. The solution is then removed and washed five times with PBST and five times with PBS.

In an embodiment of the present invention, the sample is applied directly to the substrate (noncoated substrate), and is optionally covalently bonded to the optionally activated surface of the substrate.

In an alternative of the present invention, capture molecules are immobilized in the substrate in order to capture and fix aggregates of misfolded endogenous proteins.

Preferably, antibodies of the endogenous proteins that aggregate are used as capture molecules. The antibodies specifically bind to an epitope of the endogenous proteins that aggregate.

In an alternative, the capture molecules are covalently bonded to the substrate.

In a further alternative, the capture molecules are covalently bonded to the coating, preferably a dextran layer.

In an embodiment of the present invention, the capture molecules (antibodies), optionally after activation of the CMD-coated carrier using a mixture of EDC/NHS (200 or 50 mM), are immobilized on the substrate.

Remaining carboxylate end groups to which no capture molecules were bonded can be deactivated.

Ethanolamine in DMSO is used for deactivation of these carboxylate end groups on the CMD spacer. Before application of the samples, the substrates or carriers are rinsed with PBS.

The sample to be prepared is incubated on the substrate prepared in this manner.

In an embodiment, the capture molecules and/or probes comprise a polymer composed of monomer sequences that are identical in sequence to a partial region of the endogenous proteins or show homology of at least 50% over the corresponding partial region, wherein these polymers do not aggregate and the endogenous proteins are those that aggregate.

In this sense, the term "monomer sequence" refers to a partial region of the individual proteins that form aggregates of misfolded proteins.

Preferably, the monomer sequences are regions that form an epitope to which antibodies bind that bind specifically to the proteins that form aggregates.

In an embodiment of the invention, the polypeptides of the sequences with SEQ ID Nos. 1-15 and homologs thereof, which were formed by genetic mutations in particular, are to be understood as endogenous proteins. The endogenous proteins may also be oligomers or polymers of these peptides. The SEQ ID Nos: 1-15 are also referred to as peptides or polypeptides.

"Homologs" or "homologous sequences" is understood within the meaning of the invention to refer to an amino acid sequence that shows identity with an amino acid sequence of a peptide from an endogenous pathogenic aggregate, oligomers of the misfolded proteins, or the misfolded proteins, of at least 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. Instead of the term "identity," the terms "homolog" or "homology" are used in the same sense in the present description. The identity between two nucleic acid sequences or polypeptide sequences is calculated by comparison using the program BESTFIT based on the algorithm of Smith, T. F. and Waterman, M. S (Adv. Appl. Math. 2: 482-489 (1981)), setting the following parameters for amino acids: gap creation penalty: 8 and gap extension penalty: 2; and the following parameters for nucleic acids: gap creation penalty: 50 and gap extension penalty: 3. Preferably, the identity between two nucleic acid sequences or polypeptide sequences is defined by identity of the nucleic acid sequence/polypeptide sequence over the entire respective sequence length, as it is calculated by comparison using the program GAP based on the algorithm of Needleman, S. B. and Wunsch, C D. (J. Mol. biol. 48: 443-453), setting the following parameters for amino acids: gap creation penalty: 8 and gap extension penalty: 2; and the following parameters for nucleic acids: gap creation penalty: 50 and gap extension penalty: 3.

Two amino acid sequences are identical within the meaning of the present invention, if they have the same amino acid sequence.

In a further step, aggregates of probes labeled for later detection are marked.

In an embodiment, the capture molecules and/or the probes are labeled with fluorescent dyes.

In an alternative, the capture molecules and/or probes contain specific antibodies to an epitope of the proteins formed by the aggregates.

In a variant of the present invention, antibodies are used as probes. Capture molecules and probes can be identical.

In an embodiment of the present invention, the capture molecules and probes are different. This makes it possible e.g. to use different antibodies as capture molecules and probes.

In a further embodiment of the present invention, capture molecules and probes that are identical to one another, with the exception of possible dye labeling, are used. In an alternative of the present invention, different probes are used that are identical to one another, with the exception of possible dye labeling. In a further alternative of the present invention, at least two or more different capture molecules and/or probes are used that contain or constitute different antibodies and optionally also have different dye labeling.

However, different molecules, such as different antibodies or molecules containing antibodies, can also be used as capture molecules.

Several different molecules, such as those containing or comprising different antibodies, can also be used as probes.

For later quality control of the surface, pertaining for example to the uniformity of the coating with capture molecules, capture molecules labeled with fluorescent dyes can be used. For this purpose, a dye is preferably used that does not interfere with detection. This allows subsequent structural inspection, as well as standardization of the measurement results.

For detection, the probes are labeled so that they emit an optically detectable signal selected from the group composed of fluorescence, bioluminescence and chemiluminescence emission, as well as absorption.

In an alternative, the probes are labeled with dyes. These are preferably fluorescent dyes.

In an embodiment of the present invention, least 1, 2, 3, 4, 5, 6 or more different probes are used. The probes may differ both in their specific binding to the aggregates and in their different labeling, e.g. with fluorescent dyes.

Probes that are suitable for using FRET (fluorescence resonance energy transfer) in detection can also be combined with one another.

The use of several different probes labeled with different fluorescent dyes increases the specificity of the correlation signal obtained in measurements. In addition, this also allows the masking of monomers, i.e. non-aggregated molecules. The detection of monomers in particular can be excluded, if the probe and capture molecule are identical, or if both recognized an overlapping epitope.

The utilization or use of aggregate-specific or oligomer-specific probes is therefore also the subject matter of the present invention. These bind specifically to a certain aggregate or oligomer, preferably of the above-mentioned species of misfolded proteins. By means of specific binding to a certain aggregate or oligomer, the type and/or the size, as well as the composition of the aggregate or oligomer, can be determined.

Aggregate-specific or oligomer-specific probes are therefore also the subject matter of the present invention.

Within the meaning of the present invention, the term monomer refers to a peptide molecule, an individual protein that forms aggregates of misfolded proteins. Depending on the species of origin (human and/or animal) and processing, the exact amino acid sequence of a monomer can differ in length and type. Preferred monomers are selected from SEQ ID NOs: 1-15, as well as homologs thereof.

Within the meaning of the present invention, the term oligomers refers to both aggregates and oligomers, including small, freely diffusing oligomers. An oligomer within the meaning of the invention is a polymer composed of 2, 3, 4, 5, 6, 7, 8, 9, 10, 11, 12, 13, 14, 15, 16, 17, 18, 19 or 20 monomers or multiples thereof. In this case, all of the monomers in an oligomer can, but do not have to, be identical to one another.

Therefore, aggregates are understood to refer both to oligomers and to small, free oligomers.

In a further alternative, endogenous proteins labeled with fluorescent dyes can be used as probes.

Endogenous fluids or tissues can be used as the sample to be tested. In an embodiment of the present invention, the sample is selected from CSF (CSF), blood, plasma, urine, saliva, mucosa and/or biopsy material. The samples can be subjected to various processing steps known to the person having ordinary skill in the art.

An advantage of the present invention is the possibility of determining aggregates in untreated samples, preferably CSF.

In a variant of the present invention, internal or external standards are used.

Such standards comprise or constitute a polymer composed of monomer sequences, preferably one of the sequences according to SEQ ID NOs: 1-15 or parts of one of SEQ ID NOs: 1-15 that is identical in sequence to a partial region of the endogenous proteins or shows homology of at least 50% over the corresponding partial region, wherein these polymers do not aggregate, and the endogenous proteins are those that aggregate.

According to the invention, monomer detection of endogenous proteins is excluded by using in the test system three different or three differently labeled probes that bind to a similar or the same epitope. Alternatively or additionally, the detection of monomers can be excluded in that low-intensity signals are not evaluated by means of an intensity cutoff. As larger aggregates have several binding sites for the two probes labeled with different dyes, monomer detection can be alternatively or additionally excluded by means of cross-correlation of these signals.

Detection of labeled aggregates is conducted by scanning or other types of surface imaging. Detection is preferably conducted by confocal fluorescence microscopy, fluorescence correlation spectroscopy (FCS), particularly in combination with cross-correlation and single particle immunosolvent laser scanning assay and/or laser scanning microscopy (LSM). Alternatively, detection is carried out by total internal reflection fluorescence microscopy (TIRFM).

In an alternative of the present invention, detection is carried out with a confocal laser scanning microscope.

In an embodiment of the present invention, a laser focus such as that used in laser scanning microscopy, or an FCS (fluorescence correlation spectroscopy system), is used for this purpose, as well as the corresponding super-resolving variants, such as STED or SIM. Alternatively, detection can be carried out using a TIRF microscope, as well as the corresponding super-resolving variants thereof, such as STORM or dSTORM.

Accordingly, in the embodiment of the invention, methods that are based on a non-spatially resolved signal, such as ELISA or sandwich ELISA, are excluded.

A high spatial resolution is advantageous in detection. In an embodiment of the method according to the invention, so many data points are collected that it is possible to detect an aggregate against a background signal that is caused e.g. by device-specific noise, other nonspecific signals, or nonspecific bonded probes. In this manner, as many values are read out (readout values) as there are temporally and spatially resolved events, such as pixels. Because of this spatial resolution, each event is determined against the respective background, thus providing an advantage over the ELISA method with only one readout value, few readout values and/or without a spatially resolved signal.

In an alternative, several different probes are used in the method according to the invention. In this manner, the data, i.e. the values read out, can be duplicated, as separate information is received for each point, each aggregate or each detection event, depending on the respective probe that emits the signal. This increases the specificity of the signal for each event. In this manner, the composition of each detected aggregate can also be determined, i.e. the species of the aggregate and the composition of monomers or mixtures thereof.

In this case, the number of different probes is limited only by the interference of the fluorescent dyes to be used. Therefore, 1, 2, 3, 4 or more different probe-dye combinations can be used.

Spatially and temporally resolved data are of essential importance for evaluation according to the above-described method if more than one probe is used. These data can pertain e.g. to the type and/or intensity of the fluorescence. According to the invention, in evaluating these data for the probes used and detected, the number of aggregates and their shape, size and/or composition are determined. Data on the size of the oligomers can be directly or indirectly obtained, regardless of whether the particles are smaller or larger than the temporal or spatial resolution of the imaging method used. In an embodiment, algorithms can be used for background minimization and/or intensity threshold values can be used.

Dyes known to the person having ordinary skill in the art can be used as a fluorescent dye. Alternatively, GFP (green fluorescence protein), conjugates and/or fusion proteins thereof, and quantum dots can be used.

The use of internal or external standards makes the test results objectively comparable to one another, and therefore conclusive.

In an embodiment of the present invention, an internal or external standard is used for quantitation of aggregates.

Based on analysis of the distribution of fluorescence intensity (FIDA fluorescence intensity distribution analysis), the method according to the invention is referred to as surface FIDA (surface FIDA, sFIDA). Detection is carried out by confocal fluorescence microscopy, fluorescence correlation spectroscopy (FCS), laser-scanning microscopy (LSM) and/or total internal reflection fluorescence microscopy (TIRFM), preferably LSM and/or total internal reflection fluorescence microscopy (TIRFM).

In an embodiment of the invention, up to 50 individual images per well (1000×1000 pixels, 114 nm/pixel) can be taken per fluorescence channel with a high-sensitivity CCD camera.

Background signals in the image data are removed by applying an intensity threshold. The mean number of pixels with grayscale values above the threshold is determined (sFIDA readout). If several detection probes are used, only the events colocalized in all fluorescence channels are evaluated.

The sFIDA-method was described in Bannach et al. (2012. Detection of prion protein particles in blood plasma of scrapie infected sheep. PloS one 7, e36620), as well as Wang-Dietrich et al. (2013. The amyloid-beta oligomer count in cerebrospinal fluid is a biomarker for Alzheimer's disease. Journal of Alzheimer's disease 34, 985-994), which are incorporated herein by reference.

By selecting the capture and probe molecules, it is possible to determine the size the oligomers must have in order to contribute to the detection (signal). For example, monomers, dimers, trimers, etc. can be detected. However, capture and probe molecules can also be used that are the smallest detectable unit of e.g. dimers or other polymers.

In an embodiment, the capture molecules and/or probes are used that constitute or comprise a polymer composed of monomer sequences, preferably one of the sequences according to SEQ ID NOs: 1-15 or parts of one of the SEQ ID NOs: 1-15, which are identical to a partial region of the endogenous proteins or show a homology of at least 50% over the corresponding partial region, wherein these polymers do not aggregate, and the endogenous proteins are those that aggregate.

With the method according to the invention, the precise analysis of small, freely diffusible aggregates is also possible. Because of their size, which is below the resolution of an optical microscope, small oligomers are difficult to differentiate from background fluorescence (caused e.g. by unbound antibodies).

In addition to its extremely high sensitivity, the method according to the invention also shows linearity with respect to the number of aggregates over a wide range.

The use of small, freely diffusible Aβ aggregates in combination with tau aggregates as biomarkers for the detection and recognition of protein aggregation diseases, particularly AD, is therefore also the subject matter of the present invention. The invention also concerns a method for the recognition and/or detection of protein aggregation diseases, particularly selected from the group composed of AA amyloidosis, AL amyloidosis, AApoAI amyloidosis, AApoAII amyloidosis, ATTR amyloidosis, schizophrenia and other DISC1opathies, amyotrophic lateral sclerosis, frontotemporal lobar degeneration and other FUS proteinopathies, diabetes mellitus type 2, Parkinson's disease and other synucleinopathies, tauopathies, chronic traumatic encephalopathy and other TDP-43 proteinopathies, Huntington's disease, familial visceral amyloidosis and/or Alzheimer's dementia, characterized in that a sample of a body fluid from a patient, preferably CSF or blood, and in particular CSF, is analyzed by the above-described method according to the invention.

In an embodiment, the object is achieved by means of the following procedure, referred to as the sFIDA assay:

1. A surface (preferably glass) is pretreated so that it has the lowest possible nonspecific binding capacity (e.g. it is covalently coated with a dextran layer by chemical modification). To this surface are bonded (preferably covalent) capture molecules for AA-containing particles (e.g. anti-AA antibodies). The capture molecules can all be identical, or they can be mixtures of different capture molecules.

2. The samples to be tested (CSF, blood, plasma, urine, saliva, mucous membrane, biopsy material) are then to be applied to the surface prepared in this manner, with or without prior processing steps. Nonspecifically bonded substances can then be removed by means of washing steps.

3. AA particles potentially present in the sample (e.g. AA aggregates) are labeled with a probe suitable for further detection (e.g. a fluorescent-dye bonded anti-AA-antibody).

Preferred fluorescent dyes could also include quantum dots. Preferably, the AA-containing particles are labeled with at least one more probe (e.g. a fluorescent-dye-bound anti-AA antibody). The use of several different probes that are linked to different fluorescent dyes on the one hand increases the specificity of the correlation signal finally obtained, and on the other allows masking of the AA monomers. In particular, if one of the detection probes is identical to the capture molecule (from step 1) or both recognize an overlapping epitope, the detection of AA monomers can be excluded. In order to increase specificity, the amyloid-specific dye thioflavin T can be used as an additional detection probe.

In an alternative, AA antibodies, preferably anti-serum amyloid A antibody clones 115, mc1 and/or 291, are used as capture molecules and/or probes. In an alternative, (AF488-labeled) EPR 4134 is used as a capture molecule and/or probe.

4. Steps 2 and 3 can also be interchanged. Excess probes can be removed by means of suitable washing steps.

5. Detection of labeled aggregates is conducted by scanning (e.g. by means of a laser focus such as those used in laser scanning microscopy, or for example TIRFM) or by other types of surface imaging (e.g. using a TIRF microscope). The higher the temporal and spatial resolution in this case, the greater the number of data points allowing detection of an individual aggregate against a background signal (e.g. due to device-specific noise, nonspecific signals, or nonspecific bonded probes). Thus, there is not just one readout value (as would be the case with ELISA), but as many readout values as there are temporally and spatially resolved events (e.g. pixels). Through the use of several different probes (see step 3), this information is even multiplied, and the information can be separately obtained for each point, each aggregate or each detection event that sends a signal to the probes. The specificity of the signal can thus be increased for each event.

6. The temporally and spatially resolved data (e.g. fluorescence intensity) of all the used and detected probes are used, for example, to determine the number of aggregates, their size, and their composition. In this case, for example, background minimization algorithms can be used and/or intensity threshold values can be used for further evaluation.

7. In order to make the test results mutually comparable (among distances, times, and experimenters), standards (internal and/or external) can be used.

In an embodiment, the object is achieved by means of the following procedure, referred to as the sFIDA assay:

1. A surface (preferably glass) is pretreated so that it has the lowest possible nonspecific binding capacity (e.g. it is covalently coated with a dextran layer or polyethylene glycol by chemical modification). To this surface are bonded (preferably covalent) capture molecules for AL-containing particles (e.g. anti-AL antibodies). The capture molecules can all be identical, or they can be mixtures of different capture molecules.

2. The samples to be tested (CSF, blood, plasma, urine, saliva, mucous membrane, biopsy material) are then to be applied to the surface prepared in this manner, with or without prior processing steps. Nonspecifically bonded substances can then be removed by means of washing steps.

3. AL particles potentially present in the sample (e.g. AL aggregates) are labeled with a probe suitable for further detection (e.g. a fluorescent-dye bonded anti-AL antibody). Preferred fluorescent dyes could also include quantum dots. Preferably, the AL-containing particles are labeled with at least one more probe (e.g. a fluorescent-dye-bound anti-AL antibody). The use of several different probes that are linked to different fluorescent dyes on the one hand increases the specificity of the correlation signal finally obtained, and on the other allows masking of the AL monomers. In particular, if one of the detection probes is identical to the capture molecule (from step 1) or both recognize an overlapping epitope, detection of AL monomers can be excluded. In order to increase specificity, the amyloid-specific dye thioflavin T can be used as an additional detection probe.

In an alternative, anti-lambda light chain antibody clones EPR5367, HP6054 and/or 2G9 are used as capture molecules and/or probes. In an alternative, (AF488-labeled) EPR 5367 is used as a capture molecule and/or probe.

4. Steps 2 and 3 can also be interchanged. Excess probes are removed by means of suitable washing steps.

5. Detection of labeled aggregates is conducted by scanning (e.g. by means of a laser focus such as those used in laser scanning microscopy) or by other types of surface imaging (e.g. using a TIRF microscope). The higher the temporal and spatial resolution, the greater the number of data points allowing detection of an individual aggregate against a background signal (e.g. due to device-specific noise, nonspecific signals, or nonspecific bonded probes). Thus, there is not just one readout value (as would be the case with ELISA), but as many readout values as there are temporally and spatially resolved events (e.g. pixels). Through the use of several different probes (see step 3), this information is even multiplied, and the information can be separately obtained for each point, each aggregate or each detection event that sends a signal to the probes. The specificity of the signal can thus be increased for each event.

6. The temporally and spatially resolved data of all the used and detected probes (e.g. fluorescence intensity) are used, for example, to determine the number of aggregates, their size, and their composition. In this case, for example, background minimization algorithms can be used and/or intensity threshold values can be used for further evaluation.

7. In order to make the test results mutually comparable (among distances, times, and experimenters), standards (internal and/or external) can be used.

In an embodiment, the object is achieved by means of the following procedure, referred to as the sFIDA assay:

1. A surface (preferably glass) is pretreated so that it has the lowest possible nonspecific binding capacity (e.g. it is covalently coated with a dextran layer or polyethylene glycol by chemical modification). To this surface are bonded (preferably covalent) capture molecules for AApoAI-containing particles (e.g. anti-AApoAI antibodies). The capture molecules can all be identical, or they can be mixtures of different capture molecules.

2. The samples to be tested (CSF, blood, plasma, urine, saliva, mucous membrane, biopsy material) are then to be applied to the surface prepared in this manner, with or without prior processing steps. Nonspecifically bonded substances can then be removed by means of washing steps.

3. AApoAI particles potentially present in the sample (e.g. AApoAI aggregates) are labeled with a probe suitable for further detection (e.g. a fluorescent-dye bonded anti-AApoAI antibody). Preferred fluorescent dyes could also include quantum dots. Preferably, the AApoAI-containing particles are labeled with at least one more probe (e.g. a fluorescent-dye-bound anti-AApoAI antibody). The use of several different probes that are linked to different fluorescent dyes on the one hand increases the specificity of the correlation signal finally obtained, and on the other allows masking of the AApoAI monomers. In particular, if one of the detection probes is identical to the capture molecule (from step 1) or both recognize an overlapping epitope, detection of AApoAI monomers can be excluded. In order to increase specificity, the amyloid-specific dye thioflavin T can be used as an additional detection probe.

In an alternative, anti-apolipoprotein AI antibody clones 12C8, 1409 and/or G2 are used as capture molecules and/or probes. In an alternative, (AF488-labeled) EPR 1368Y is used as a capture molecule and/or probe.

4. Steps 2 and 3 can also be interchanged. Excess probes can be removed by means of suitable washing steps.

5. Detection of labeled aggregates is conducted by scanning (e.g. by means of a laser focus such as those used in laser scanning microscopy) or by other types of surface imaging (e.g. using a TIRF microscope). The higher the temporal and spatial resolution, the greater the number of data points allowing detection of an individual aggregate against a background signal (e.g. due to device-specific noise, nonspecific signals, or nonspecific bonded probes). Thus, there is not just one readout value (as would be the case with ELISA), but as many readout values as there are temporally and spatially resolved events (e.g. pixels). Through the use of several different probes (see step 3), this information is even multiplied, and the information can be separately obtained for each point, each aggregate or each detection event that sends a signal to the probes. The specificity of the signal can thus be increased for each event.

6. The temporally and spatially resolved data (e.g. fluorescence intensity) of all the used and detected probes are used, for example, to determine the number of aggregates, their size, and their composition. In this case, for example, background minimization algorithms can be used and/or intensity threshold values can be used for further evaluation.

7. In order to make the test results mutually comparable (among distances, times, and experimenters), standards (internal and/or external) can be used.

In an embodiment, the object is achieved by means of the following procedure, referred to as the sFIDA assay:

1. A surface (preferably glass) is pretreated so that it has the lowest possible nonspecific binding capacity (e.g. it is covalently coated with a dextran layer or polyethylene glycol by chemical modification). To this surface are bonded (preferably covalent) capture molecules for AApoAII-containing particles (e.g. anti-AApoAII antibodies). The capture molecules can all be identical, or they can be mixtures of different capture molecules.

2. The samples to be tested (CSF, blood, plasma, urine, saliva, mucous membrane, biopsy material) are then to be applied to the surface prepared in this manner, with or without prior processing steps. Nonspecifically bonded substances can then be removed by means of washing steps.

3. AApoAII particles potentially present in the sample (e.g. AApoAII aggregates) are labeled with a probe suitable for further detection (e.g. a fluorescent-dye bonded anti-AApoAII antibody). Preferred fluorescent dyes could also include quantum dots. The AApoAII-containing particles are preferably labeled with at least one further probe (e.g. a fluorescent dye-bound anti-AApoAII antibody). The use of several different probes that are linked to different fluorescent dyes on the one hand increases the specificity of the correlation signal finally obtained, and on the other allows masking of the AApoAII monomers. In particular, if one of the detection probes is identical to the capture molecule (from step 1) or both recognize an overlapping epitope, detection of AApoAII monomers can be excluded. In order to increase specificity, the amyloid-specific dye thioflavin T can be used as an additional detection probe.

In an alternative, anti-apolipoprotein AII antibody clones 4F3, EPR2913 and/or EP2912 are used as capture molecules and/or probes.

4. Steps 2 and 3 can also be interchanged. Excess probes can be removed by means of suitable washing steps.

5. Detection of labeled aggregates is conducted by scanning (e.g. by means of a laser focus such as those used in laser scanning microscopy) or by other types of surface imaging (e.g. using a TIRF microscope). In this case, the higher the spatial resolution, the greater the number of data points allowing detection of an individual aggregate against a background signal (e.g. due to device-specific noise, nonspecific signals, or nonspecific bonded probes). Thus, there is not just one readout value (as would be the case with ELISA), but as many readout values as spatially resolved events (e.g. pixels). Through the use of several different probes (see step 3), this information is even multiplied, and the information can be separately obtained for each point, each aggregate or each detection event that sends a signal to the probes. The specificity of the signal can thus be increased for each event.

6. The temporally and spatially resolved data (e.g. fluorescence intensity) of all the used and detected probes are used, for example, to determine the number of aggregates, their size, and their composition. In this case, for example, background minimization algorithms can be used and/or intensity threshold values can be used for further evaluation.

7. In order to make the test results mutually comparable (among distances, times, and experimenters), standards (internal and/or external) can be used.

In an embodiment, the object is achieved by means of the following procedure, referred to as the sFIDA assay:

1. A surface (preferably glass) is pretreated so that it has the lowest possible nonspecific binding capacity (e.g. it is covalently coated with a dextran layer or polyethylene glycol by chemical modification). To this surface are bonded (preferably covalent) capture molecules for ATTR-containing particles (e.g. anti-ATTR antibodies). The capture molecules can all be identical, or they can be mixtures of different capture molecules.

2. The samples to be tested (CSF, blood, plasma, urine, saliva, mucous membrane, biopsy material) are then to be applied to the surface prepared in this manner, with or without prior processing steps. Nonspecifically bonded substances can then be removed by means of washing steps.

3. ATTR particles potentially present in the sample (e.g. ATTR aggregates) are labeled with a probe suitable for further detection (e.g. a fluorescent-dye bonded anti-ATTR antibody). Preferred fluorescent dyes could also include quantum dots. Preferably, the ATTR-containing particles are labeled with at least one more probe (e.g. a fluorescent-dye-bound anti-ATTR antibody). The use of several different probes that are linked to different fluorescent dyes on the one hand increases the specificity of the correlation signal finally obtained, and on the other allows masking of the ATTR monomers. In particular, if one of the detection probes is identical to the capture molecule (from step 1) or both recognize an overlapping epitope, detection of ATTR monomers can be excluded. In order to increase specificity, the amyloid-specific dye thioflavin T can be used as an additional detection probe.

In an alternative, anti-prealbumin antibody clones EP2929Y, EPR3119 and/or 10E1 are used as capture molecules and/or probes.

4. Steps 2 and 3 can also be interchanged. Excess probes are removed by means of suitable washing steps.

5. Detection of labeled aggregates is conducted by scanning (e.g. by means of a laser focus such as those used in laser scanning microscopy) or by other types of surface imaging (e.g. using a TIRF microscope). The higher the temporal and spatial resolution, the greater the number of data points allowing detection of an individual aggregate against a background signal (e.g. due to device-specific noise, nonspecific signals, or nonspecific bonded probes). Thus, there is not just one readout value (as would be the case with ELISA), but as many readout values as there are temporally and spatially resolved events (e.g. pixels). Through the use of several different probes (see step 3), this information is even multiplied, and the information can be separately obtained for each point, each aggregate or each detection event that sends a signal to the probes. The specificity of the signal can thus be increased for each event.

6. The temporally and spatially resolved data (e.g. fluorescence intensity) of all the used and detected probes are used, for example, to determine the number of aggregates, their size, and their composition. In this case, for example, background minimization algorithms can be used and/or intensity threshold values can be used for further evaluation.

7. In order to make the test results mutually comparable (among distances, times, and experimenters), standards (internal and/or external) can be used.

In an embodiment, the object is achieved by means of the following procedure, referred to as the sFIDA assay:

1. A surface (preferably glass) is pretreated so that it has the lowest possible nonspecific binding capacity (e.g. it is covalently coated with a dextran layer or polyethylene glycol by chemical modification). To this surface are bonded (preferably covalent) capture molecules for DISC1-containing particles (e.g. anti-DISC1 antibodies). The capture molecules can all be identical, or they can be mixtures of different capture molecules.

2. The samples to be tested (CSF, blood, plasma, urine, saliva, mucous membrane, biopsy material) are then to be applied to the surface prepared in this manner, with or without prior processing steps. Nonspecifically bonded substances can then be removed by means of washing steps.

3. DISC1 particles potentially present in the sample (e.g. DISC1-aggregates) are labeled with a probe suitable for further detection (e.g. a fluorescent-dye bonded anti-DISC1 antibody). Preferred fluorescent dyes could also include quantum dots. Preferably, the DISC1-containing particles are labeled with at least one more probe (e.g. a fluorescent-dye-bound anti-DISC1 antibody). The use of several different probes that are linked to different fluorescent dyes on the one hand increases the specificity of the correlation signal finally obtained, and on the other allows masking of the DISC1 monomers. In particular, if one of the detection probes is identical to the capture molecule (from step 1) or both recognize an overlapping epitope, detection of DISC1 monomers can be excluded. In order to increase specificity, the amyloid-specific dye thioflavin T can be used as an additional detection probe.

In an alternative, anti-DISC1 antibody clones 14F2, 2C7 and/or FFD5 are used as capture molecules and/or probes. In an alternative, anti-DISC1-AK 14F2 is used as a capture antibody and 14F2-AF633 as a detection probe.

4. Steps 2 and 3 can also be interchanged. Excess probes can be removed by means of suitable washing steps.

5. Detection of labeled aggregates is conducted by scanning (e.g. by means of a laser focus such as those used in laser scanning microscopy) or by other types of surface imaging (e.g. using a TIRF microscope). The higher the temporal and spatial resolution, the greater the number of data points allowing detection of an individual aggregate against a background signal (e.g. due to device-specific noise, nonspecific signals, or nonspecific bonded probes). Thus, there is not just one readout value (as would be the case with ELISA), but as many readout values as there are temporally and spatially resolved events (e.g. pixels). Through the use of several different probes (see step 3), this information is even multiplied, and the information can be separately obtained for each point, each aggregate or each detection event that sends a signal to the probes. The specificity of the signal can thus be increased for each event.

6. The temporally and spatially resolved data (e.g. fluorescence intensity) of all the used and detected probes are used, for example, to determine the number of aggregates, their size, and their composition. In this case, for example, background minimization algorithms can be used and/or intensity threshold values can be used for further evaluation.

7. In order to make the test results mutually comparable (among distances, times, and experimenters), standards (internal and/or external) can be used.

In an embodiment, the object is achieved by means of the following procedure, referred to as the sFIDA assay:

1. A surface (preferably glass) is pretreated so that it has the lowest possible nonspecific binding capacity (e.g. it is covalently coated with a dextran layer or polyethylene glycol by chemical modification). To this surface are bonded (preferably covalent) capture molecules for FUS-containing particles (e.g. anti-FUS antibodies). The capture molecules can all be identical, or they can be mixtures of different capture molecules.

2. The samples to be tested (CSF, blood, plasma, urine, saliva, mucous membrane, biopsy material) are then to be applied to the surface prepared in this manner, with or without prior processing steps. Nonspecifically bonded substances can then be removed by means of washing steps.

3. FUS particles potentially present in the sample (e.g. FUS aggregates) are labeled with a probe suitable for further detection (e.g. a fluorescent-dye bonded anti-FUS antibody). Preferred fluorescent dyes could also include quantum dots. Preferably, the FUS-containing particles are labeled with at least one more probe (e.g. a fluorescent-dye-bound anti-FUS antibody). The use of several different probes that are linked to different fluorescent dyes on the one hand increases the specificity of the correlation signal finally obtained, and on the other allows masking of the FUS monomers. In particular, if one of the detection probes is identical to the capture molecule (from step 1) or both recognize an overlapping epitope, detection of FUS monomers can be excluded. In order to increase specificity, the amyloid-specific dye thioflavin T can be used as an additional detection probe.

In an alternative, anti-TLS/FUS antibody clones EP 5812, EPR5813 and/or CL0190 are used as capture molecules and/or probes.

4. Steps 2 and 3 can also be interchanged. Excess probes can be removed by means of suitable washing steps.

5. Detection of labeled aggregates is conducted by scanning (e.g. by means of a laser focus such as those used in laser scanning microscopy) or by other types of surface imaging (e.g. using a TIRF microscope). The higher the temporal and spatial resolution, the greater the number of data points allowing detection of an individual aggregate against a background signal (e.g. due to device-specific noise, nonspecific signals, or nonspecific bonded probes). Thus, there is not just one readout value (as would be the case with ELISA), but as many readout values as there are temporally and spatially resolved events (e.g. pixels). Through the use of several different probes (see step 3), this information is even multiplied, and the information can be separately obtained for each point, each aggregate or each detection event that sends a signal to the probes. The specificity of the signal can thus be increased for each event.

6. The temporally and spatially resolved data of all the used and detected probes (e.g. fluorescence intensity) are used, for example, to determine the number of aggregates, their size, and their composition. In this case, for example, background minimization algorithms can be used and/or intensity threshold values can be used for further evaluation.

7. In order to make the test results mutually comparable (among distances, times, and experimenters), standards (internal and/or external) can be used.

In an embodiment, the object is achieved by means of the following procedure, referred to as the sFIDA assay:

1. A surface (preferably glass) is pretreated so that it has the lowest possible nonspecific binding capacity (e.g. it is covalently coated with a dextran layer or polyethylene glycol by chemical modification). To this surface are bonded (preferably covalent) capture molecules for IAPP-containing particles (e.g. anti-IAPP antibodies). The capture molecules can all be identical, or they can be mixtures of different capture molecules.

2. The samples to be tested (CSF, blood, plasma, urine, saliva, mucous membrane, biopsy material) are then to be applied to the surface prepared in this manner, with or without prior processing steps. Nonspecifically bonded substances can then be removed by means of washing steps.

3. IAPP particles potentially present in the sample (e.g. IAPP aggregates) are labeled with a probe suitable for further detection (e.g. a fluorescent-dye bonded anti-IAPP antibody). Preferred fluorescent dyes could also include quantum dots. Preferably, the IAPP-containing particles are labeled with at least one more probe (e.g. a fluorescent-dye-bound anti-IAPP antibody). The use of several different probes that are linked to different fluorescent dyes on the one hand increases the specificity of the correlation signal finally obtained, and on the other allows masking of the IAPP monomers. In particular, if one of the detection probes is identical to the capture molecule (from step 1) or both recognize an overlapping epitope, detection of IAPP monomers can be excluded. In order to increase specificity, the amyloid-specific dye thioflavin T can be used as an additional detection probe.

In an alternative, anti-amylin antibody clone R10/99 is used as a capture molecule and/or probe.

4. Steps 2 and 3 can also be interchanged. Excess probes can be removed by means of suitable washing steps.

5. Detection of labeled aggregates is conducted by scanning (e.g. by means of a laser focus such as those used in laser scanning microscopy) or by other types of surface imaging (e.g. using a TIRF microscope). The higher the temporal and spatial resolution, the greater the number of data points allowing detection of an individual aggregate against a background signal (e.g. due to device-specific noise, nonspecific signals, or nonspecific bonded probes). Thus, there is not just one readout value (as would be the case with ELISA), but as many readout values as there are temporally and spatially resolved events (e.g. pixels). Through the use of several different probes (see step 3), this information is even multiplied, and the information can be separately obtained for each point, each aggregate or each detection event that sends a signal to the probes. The specificity of the signal can thus be increased for each event.

6. The temporally and spatially-resolved data (e.g. fluorescence intensity) of all the used and detected probes are used, for example, to determine the number of aggregates, their size, and their composition. In this case, for example, background minimization algorithms can be used and/or intensity threshold values can be used for further evaluation.

7. In order to make the test results mutually comparable (among distances, times, and experimenters), standards (internal and/or external) can be used.

In an embodiment, the object is achieved by means of the following procedure, referred to as the sFIDA assay:

1. A surface (preferably glass) is pretreated so that it has the lowest possible nonspecific binding capacity (e.g. it is covalently coated with a dextran layer or polyethylene glycol by chemical modification). To this surface are bonded (preferably covalent) capture molecules for SOD1-containing particles (e.g. anti-SOD1 antibodies). The capture molecules can all be identical, or they can be mixtures of different capture molecules.

2. The samples to be tested (CSF, blood, plasma, urine, saliva, mucous membrane, biopsy material) are then to be applied to the surface prepared in this manner, with or without prior processing steps. Nonspecifically bonded substances can then be removed by means of washing steps.

3. SOD1 particles potentially present in the sample (e.g. SOD1 aggregates) are labeled with a probe suitable for further detection (e.g. a fluorescent-dye bonded anti-SOD1 antibody). Preferred fluorescent dyes could also include quantum dots. Preferably, the SOD1-containing particles are labeled with at least one more probe (e.g. a fluorescent-dye-bound anti-SOD1 antibody). The use of several different probes that are linked to different fluorescent dyes on the one hand increases the specificity of the correlation signal finally obtained, and on the other allows masking of the SOD1 monomers. In particular, if one of the detection probes is identical to the capture molecule (from step 1) or both recognize an overlapping epitope, detection of SOD1 monomers can be excluded. In order to increase specificity, the amyloid-specific dye thioflavin T can be used as an additional detection probe.

In an alternative, anti-superoxide dismutase 1 antibody clones 2F5, 71G8 and/or EPR1726 are used as capture molecules and/or probes. In an alternative, (AF488-labeled) EPR 1726 is used as a capture molecule and/or probe.

4. Steps 2 and 3 can also be interchanged. Excess probes can be removed by means of suitable washing steps.

5. Detection of labeled aggregates is conducted by scanning (e.g. by means of a laser focus such as those used in laser scanning microscopy) or by other types of surface imaging (e.g. using a TIRF microscope). The higher the temporal and spatial resolution, the greater the number of data points allowing detection of an individual aggregate against a background signal (e.g. due to device-specific noise, nonspecific signals, or nonspecific bonded probes). Thus, there is not just one readout value (as would be the case with ELISA), but as many readout values as there are temporally and spatially resolved events (e.g. pixels). Through the use of several different probes (see step 3), this information is even multiplied, and the information can be separately obtained for each point, each aggregate or each detection event that sends a signal to the probes. The specificity of the signal can thus be increased for each event.

6. The temporally and spatially resolved data (e.g. fluorescence intensity) of all the used and detected probes are used, for example, to determine the number of aggregates, their size, and their composition. In this case, for example, background minimization algorithms can be used and/or intensity threshold values can be used for further evaluation.

7. In order to make the test results mutually comparable (among distances, times, and experimenters), standards (internal and/or external) can be used.

In an embodiment, the object is achieved by means of the following procedure, referred to as the sFIDA-assays:

1. A surface (preferably glass) is pretreated so that it has the lowest possible nonspecific binding capacity (e.g. it is covalently coated with a dextran layer or polyethylene glycol by chemical modification). To this surface are bonded (preferably covalent) capture molecules for α-synuclein-containing particles (e.g. anti-α-synuclein antibodies). The capture molecules can all be identical, or they can be mixtures of different capture molecules.

2. The samples to be tested (CSF, blood, plasma, urine, saliva, mucous membrane, biopsy material) are then to be applied to the surface prepared in this manner, with or without prior processing steps. Nonspecifically bonded substances can then be removed by means of washing steps.

3. α-synuclein particles potentially present in the sample (e.g. α-synuclein aggregates) are labeled with a probe suitable for further detection (e.g. a fluorescent-dye bonded α-synuclein antibody). Preferred fluorescent dyes could also include quantum dots. Preferably, the α-synuclein-containing particles are labeled with at least one more probe (e.g. a fluorescent-dye-bound anti-α-synuclein antibody). The use of several different probes that are linked to different fluorescent dyes on the one hand increases the specificity of the correlation signal finally obtained, and on the other allows masking of the α-synuclein monomers. In particular, if one of the detection probes is identical to the capture molecule (from step 1) or both recognize an overlapping epitope, detection of α-synuclein monomers can be excluded. In order to increase specificity, the amyloid-specific dye thioflavin T can be used as an additional detection probe.

In an alternative, anti-α-synuclein antibody clones 2B2A11, 3H2897 and/or 211 are used as capture molecules and/or probes. In an alternative, anti-αSyn-Aβ 2B2A11 is used as a capture molecule and fluorescence-labeled anti-αSyn-ABs 3H2897-AF633 or 211-AF488 are used as detection probes.

4. Steps 2 and 3 can also be interchanged. Excess probes can be removed by means of suitable washing steps.

5. Detection of labeled aggregates is conducted by scanning (e.g. by means of a laser focus such as those used in laser scanning microscopy) or by other types of surface imaging (e.g. using a TIRF microscope). The higher the temporal and spatial resolution, the greater the number of data points allowing detection of an individual aggregate against a background signal (e.g. due to device-specific noise, nonspecific signals, or nonspecific bonded probes). Thus, there is not just one readout value (as would be the case with ELISA), but as many readout values as there are temporally and spatially resolved events (e.g. pixels). Through the use of several different probes (see step 3), this information is even multiplied, and the information can be separately obtained for each point, each aggregate or each detection event that sends a signal to the probes. The specificity of the signal can thus be increased for each event.

6. The temporally and spatially-resolved data (e.g. fluorescence intensity) of all the used and detected probes are used, for example, to determine the number of aggregates, their size, and their composition. In this case, for example, background minimization algorithms can be used and/or intensity threshold values can be used for further evaluation.

7. In order to make the test results mutually comparable (among distances, times, and experimenters), standards (internal and/or external) can be used.

In an embodiment, the object is achieved by means of the following procedure, referred to as the sFIDA assay:

1. A surface (preferably glass) is pretreated so that it has the lowest possible nonspecific binding capacity (e.g. it is covalently coated with a dextran layer or polyethylene glycol by chemical modification). To this surface are bonded (preferably covalent) capture molecules for tau-containing particles (e.g. anti-tau antibodies). The capture molecules can all be identical, or they can be mixtures of different capture molecules.

2. The samples to be tested (CSF, blood, plasma, urine, saliva, mucous membrane, biopsy material) are then to be applied to the surface prepared in this manner, with or without prior processing steps. Nonspecifically bonded substances can then be removed by means of washing steps.

3. Tau particles potentially present in the sample (e.g. tau aggregates) are labeled with a probe suitable for further detection (e.g. a fluorescent-dye bonded anti-tau antibody). Preferred fluorescent dyes could also include quantum dots. Preferably, the tau-containing particles are labeled with at least one more probe (e.g. a fluorescent-dye-bound anti-tau antibody). The use of several different probes that are linked to different fluorescent dyes on the one hand increases the specificity of the correlation signal finally obtained, and on the other allows masking of the tau monomers. In particular, if one of the detection probes is identical to the capture molecule (from step 1) or both recognize an overlapping epitope, detection of tau monomers can be excluded. In order to increase specificity, the amyloid-specific dye thioflavin T can be used as an additional detection probe.

In an alternative, anti-tau antibody clones E178, tau 46 and/or tau 5 are used as capture molecules and/or probes. In an alternative, anti-tau 6E10/Atto488 and/or Nab228 are used as capture molecules and/or probes.

4. Steps 2 and 3 can also be interchanged. Excess probes can be removed by means of suitable washing steps.

5. Detection of labeled aggregates is conducted by scanning (e.g. by means of a laser focus such as those used in laser scanning microscopy) or by other types of surface imaging (e.g. using a TIRF microscope). The higher the temporal and spatial resolution, the greater the number of data points allowing detection of an individual aggregate against a background signal (e.g. due to device-specific noise, nonspecific signals, or nonspecific bonded probes). Thus, there is not just one readout value (as would be the case with ELISA), but as many readout values as there are temporally and spatially resolved events (e.g. pixels). Through the use of several different probes (see step 3), this information is even multiplied, and the information can be separately obtained for each point, each aggregate or each detection event that sends a signal to the probes. The specificity of the signal can thus be increased for each event.

6. The temporally and spatially resolved data (e.g. fluorescence intensity) of all the used and detected probes are used, for example, to determine the number of aggregates, their size, and their composition. In this case, for example, background minimization algorithms can be used and/or intensity threshold values can be used for further evaluation.

7. In order to make the test results mutually comparable (among distances, times, and experimenters), standards (internal and/or external) can be used.

In an embodiment, the object is achieved by means of the following procedure, referred to as the sFIDA assay:

1. A surface (preferably glass) is pretreated so that it has the lowest possible nonspecific binding capacity (e.g. it is covalently coated with a dextran layer or polyethylene glycol by chemical modification). To this surface are bonded (preferably covalent) capture molecules for TDP-43-containing particles (e.g. anti-TDP-43 antibodies). The capture molecules can all be identical, or they can be mixtures of different capture molecules.

2. The samples to be tested (CSF, blood, plasma, urine, saliva, mucous membrane, biopsy material) are then to be applied to the surface prepared in this manner, with or without prior processing steps. Nonspecifically bonded substances can then be removed by means of washing steps.

3. TDP-43 particles potentially present in the sample (e.g. TDP-43 aggregates) are labeled with a probe suitable for further detection (e.g. a fluorescent-dye bonded anti-TDP-43 antibody). Preferred fluorescent dyes could also include quantum dots. Preferably, the TDP-43-containing particles are labeled with at least one more probe (e.g. a fluorescent-dye-bound anti-TDP-43 antibody). The use of several different probes that are linked to different fluorescent dyes on the one hand increases the specificity of the correlation signal finally obtained, and on the other allows masking of the TDP-43 monomers. In particular, if one of the detection probes is identical to the capture molecule (from step 1) or both recognize an overlapping epitope, detection of TDP-43 monomers can be excluded.

In order to increase specificity, the amyloid-specific dye thioflavin T can be used as an additional detection probe.

In an alternative, anti-TARDBP antibody clones EPR5810, 3H8 and/or K1B8 are used as capture molecules and/or probes. In an alternative, (AF488-labeled) EPR 5810 is used as a capture molecule and/or probe.

4. Steps 2 and 3 can also be interchanged. Excess probes are removed by means of suitable washing steps.

5. Detection of labeled aggregates is conducted by scanning (e.g. by means of a laser focus such as those used in laser scanning microscopy) or by other types of surface imaging (e.g. using a TIRF microscope). The higher the temporal and spatial resolution, the greater the number of data points allowing detection of an individual aggregate against a background signal (e.g. due to device-specific noise, nonspecific signals, or nonspecific bonded probes). Thus, there is not just one readout value (as would be the case with ELISA), but as many readout values as there are temporally and spatially resolved events (e.g. pixels). Through the use of several different probes (see step 3), this information is even multiplied, and the information can be separately obtained for each point, each aggregate or each detection event that sends a signal to the probes. The specificity of the signal can thus be increased for each event.

6. The temporally and spatially resolved data (e.g. fluorescence intensity) of all the used and detected probes are used, for example, to determine the number of aggregates, their size, and their composition. In this case, for example, background minimization algorithms can be used and/or intensity threshold values can be used for further evaluation.

7. In order to make the test results mutually comparable (among distances, times, and experimenters), standards (internal and/or external) can be used.

In an embodiment, the object is achieved by means of the following procedure, referred to as the sFIDA-assays:

1. A surface (preferably glass) is pretreated so that it has the lowest possible nonspecific binding capacity (e.g. it is covalently coated with a dextran layer or polyethylene glycol by chemical modification). To this surface are bonded (preferably covalent) capture molecules for huntingtin-containing particles (e.g. anti-huntingtin antibodies). The capture molecules can all be identical, or they can be mixtures of different capture molecules.

2. The samples to be tested (CSF, blood, plasma, urine, saliva, mucous membrane, biopsy material) are then to be applied to the surface prepared in this manner, with or without prior processing steps. Nonspecifically bonded substances can then be removed by means of washing steps.

3. Huntingtin particles potentially present in the sample (e.g. huntingtin aggregates) are labeled with a probe suitable for further detection (e.g. a fluorescent-dye bonded anti-huntingtin antibody). Preferred fluorescent dyes could also include quantum dots. Preferably, the huntingtin-containing particles are labeled with at least one more probe (e.g. a fluorescent-dye-bound anti-huntingtin antibody). The use of several different probes that are linked to different fluorescent dyes on the one hand increases the specificity of the correlation signal finally obtained, and on the other allows masking of the huntingtin monomers. In particular, if one of the detection probes is identical to the capture molecule (from step 1) or both recognize an overlapping epitope, detection of huntingtin monomers can be excluded.

In order to increase specificity, the amyloid-specific dye thioflavin T can be used as an additional detection probe.

In an alternative, anti-huntingtin antibody clones EP867Y, D7F7 and/or HIP-1 are used as capture molecules and/or probes.

4. Steps 2 and 3 can also be interchanged. Excess probes can be removed by means of suitable washing steps.

5. Detection of labeled aggregates is conducted by scanning (e.g. by means of a laser focus such as those used in laser scanning microscopy) or by other types of surface imaging (e.g. using a TIRF microscope). The higher the temporal and spatial resolution, the greater the number of data points allowing detection of an individual aggregate against a background signal (e.g. due to device-specific noise, nonspecific signals, or nonspecific bonded probes). Thus, there is not just one readout value (as would be the case with ELISA), but as many readout values as there are temporally and spatially resolved events (e.g. pixels). Through the use of several different probes (see step 3), this information is even multiplied, and the information can be separately obtained for each point, each aggregate or each detection event that sends a signal to the probes. The specificity of the signal can thus be increased for each event.

6. The temporally and spatially resolved data (e.g. fluorescence intensity) of all the used and detected probes are used, for example, to determine the number of aggregates, their size, and their composition. In this case, for example, background minimization algorithms can be used and/or intensity threshold values can be used for further evaluation.

7. In order to make the test results mutually comparable (among distances, times, and experimenters), standards (internal and/or external) can be used.

In an embodiment, the object is achieved by means of the following procedure, referred to as the sFIDA-assays:

1. A surface (preferably glass) is pretreated so that it has the lowest possible nonspecific binding capacity (e.g. it is covalently coated with a dextran layer or polyethylene glycol by chemical modification). To this surface are bonded (preferably covalent) capture molecules for ALys-containing particles (e.g. anti-ALys antibodies). The capture molecules can all be identical, or they can be mixtures of different capture molecules.

2. The samples to be tested (CSF, blood, plasma, urine, saliva, mucous membrane, biopsy material) are then to be applied to the surface prepared in this manner, with or without prior processing steps. Nonspecifically bonded substances can then be removed by means of washing steps.

3. ALys particles potentially present in the sample (e.g. ALys aggregates) are labeled with a probe suitable for further detection (e.g. a fluorescent-dye bonded anti-ALys antibody). Preferred fluorescent dyes could also include quantum dots. Preferably, the ALys-containing particles are labeled with at least one more probe (e.g. a fluorescent-dye-bound anti-ALys antibody). The use of several different probes that are linked to different fluorescent dyes on the one hand increases the specificity of the correlation signal finally obtained, and on the other allows masking of the ALys monomers. In particular, if one of the detection probes is identical to the capture molecule (from step 1) or both recognize an overlapping epitope, detection of ALys monomers can be excluded. In order to increase specificity, the amyloid-specific dye thioflavin T can be used as an additional detection probe.

In an alternative, anti-lysozyme antibody clones BGN/06/961 and/or BGN/0696 2B10 are used as capture molecules and/or probes. In an alternative, (AF488-labeled) EPR 2994 is used as a capture molecule and/or probe.

4. Steps 2 and 3 can also be interchanged. Excess probes can be removed by means of suitable washing steps.

5. Detection of labeled aggregates is conducted by scanning (e.g. by means of a laser focus such as those used in laser scanning microscopy) or by other types of surface imaging (e.g. using a TIRF microscope). The higher the temporal and spatial resolution, the greater the number of data points allowing detection of an individual aggregate against a background signal (e.g. due to device-specific noise, nonspecific signals, or nonspecific bonded probes). Thus, there is not just one readout value (as would be the case with ELISA), but as many readout values as there are temporally and spatially resolved events (e.g. pixels). Through the use of several different probes (see step 3), this information is even multiplied, and the information can be separately obtained for each point, each aggregate or each detection event that sends a signal to the probes. The specificity of the signal can thus be increased for each event.

6. For evaluation, the temporally and spatially resolved data (e.g. fluorescence intensity) of all the used and detected probes are used, for example, to determine the number of aggregates, their size, and their composition. In this case, for example, background minimization algorithms can be used and/or intensity threshold values can be used for further evaluation.

7. In order to make the test results mutually comparable (among distances, times, and experimenters), standards (internal and/or external) can be used.

In an embodiment, the subject matter of the present invention is a method for selective quantitation and/or characterization of aggregates of the type serum amyloid A protein aggregates in body fluids as biomarkers for AA amyloidosis. In an embodiment, testing is conducted for a further aggregate type selected from the group composed of IgG light chain aggregates, AapoAI aggregates, AapoAII aggregates, ATTR aggregates, DISC1 aggregates, FUS aggregates, IAPP aggregates, SOD1 aggregates, α-synuclein aggregates, tau aggregates, TDP-43 aggregates, huntingtin aggregates, lysozyme aggregates and Aβ aggregates.

In an embodiment, the subject matter of the present invention is a method for selective quantitation and/or characterization of mixed aggregates of the type serum amyloid A protein aggregates with one or more proteins selected from the group composed of IgG light chain aggregates, AapoAI aggregates, AapoAII aggregates, ATTR aggregates, DISC1 aggregates, FUS aggregates, IAPP aggregates, SOD1 aggregates, α-synuclein aggregates, tau aggregates, TDP-43 aggregates, huntingtin aggregates, lysozyme aggregates and Aβ aggregates in body fluids as biomarkers for AA amyloidosis.

In an embodiment, the subject matter of the present invention is a method for selective quantitation and/or characterization of aggregates of the type IgG light chain aggregates in body fluids as biomarkers for AL amyloidosis. In an embodiment, testing is conducted for a further aggregate type selected from the group composed of serum amyloid A protein aggregates, AapoAI aggregates, AapoAII aggregates, ATTR aggregates, DISC1 aggregates, FUS aggregates, IAPP aggregates, SOD1 aggregates, α-synuclein aggregates, tau aggregates, TDP-43 aggregates, huntingtin aggregates, lysozyme aggregates and Aβ aggregates.

In an embodiment, the subject matter of the present invention is a method for selective quantitation and/or characterization of mixed aggregates of the type IgG light chain aggregates with one or more proteins selected from the group composed of serum amyloid A protein aggregates, AapoAI aggregates, AapoAII aggregates, ATTR aggregates, DISC1 aggregates, FUS aggregates, IAPP aggregates, SOD1 aggregates, α-synuclein aggregates, tau aggregates, TDP-43 aggregates, huntingtin aggregates, lysozyme aggregates and Aβ aggregates in body fluids as biomarkers for AL amyloidosis.

In an embodiment, the subject matter of the present invention is a method for selective quantitation and/or characterization of aggregates of the type AApoAI aggregates in body fluids as biomarkers for AapoAI amyloidosis. In an embodiment, testing is conducted for a further aggregate type selected from the group composed of serum amyloid A protein aggregates, IgG light chain aggregates, AapoAII aggregates, ATTR aggregates, DISC1 aggregates, FUS aggregates, IAPP aggregates, SOD1 aggregates, α-synuclein aggregates, tau aggregates, TDP-43 aggregates, huntingtin aggregates, lysozyme aggregates and Aβ aggregates.

In an embodiment, the subject matter of the present invention is a method for selective quantitation and/or characterization of mixed aggregates of the type AapoAI aggregates with one or more proteins selected from the group composed of serum amyloid A protein aggregates, IgG light chain aggregates, AapoAII aggregates, ATTR aggregates, DISC1 aggregates, FUS aggregates, IAPP aggregates, SOD1 aggregates, α-synuclein aggregates, tau aggregates, TDP-43 aggregates, huntingtin aggregates, lysozyme aggregates and Aβ aggregates in body fluids as biomarkers for AapoAI amyloidosis.

In an embodiment, the subject matter of the present invention is a method for selective quantitation and/or characterization of aggregates of the type AApoAII aggregates in body fluids as biomarkers for AapoAII amyloidosis. In an embodiment, testing is conducted for a further aggregate type selected from the group composed of serum amyloid A protein aggregates, IgG light chain aggregates, AapoAI aggregates, ATTR aggregates, DISC1 aggregates, FUS aggregates, IAPP aggregates, SOD1 aggregates, α-synuclein aggregates, tau aggregates, TDP-43 aggregates, huntingtin aggregates, lysozyme aggregates and Aβ aggregates.

In an embodiment, the subject matter of the present invention is a method for selective quantitation and/or characterization of mixed aggregates of the type AapoAII aggregates with one or more proteins selected from the group composed of serum amyloid A protein aggregates, IgG light chain aggregates, AapoAI aggregates, ATTR aggregates, DISC1 aggregates, FUS aggregates, IAPP aggregates, SOD1 aggregates, α-synuclein aggregates, tau aggregates, TDP-43 aggregates, huntingtin aggregates, lysozyme aggregates and Aβ aggregates in body fluids as biomarkers for AApoAII amyloidosis.

In an embodiment, the subject matter of the present invention is a method for selective quantitation and/or characterization of aggregates of the type ATTR aggregates in body fluids as biomarkers for ATTR amyloidosis. In an embodiment, testing is conducted for a further aggregate type selected from the group composed of serum amyloid A protein aggregates, IgG light chain aggregates, AapoAI aggregates, AapoAII aggregates, DISC1 aggregates, FUS aggregates, IAPP aggregates, SOD1 aggregates, α-synuclein aggregates, tau aggregates, TDP-43 aggregates, huntingtin aggregates, lysozyme aggregates and Aβ aggregates.

In an embodiment, the subject matter of the present invention is a method for selective quantitation and/or characterization of mixed aggregates of the type ATTR aggregates with one or more proteins selected from the group composed of serum amyloid A protein aggregates, IgG light chain aggregates, AapoAI aggregates, AapoAII aggregates, DISC1 aggregates, FUS aggregates, IAPP aggregates, SOD1 aggregates, α-synuclein aggregates, tau aggregates, TDP-43 aggregates, huntingtin aggregates, lysozyme aggregates and Aβ aggregates in body fluids as biomarkers for ATTR amyloidosis.

In an embodiment, the subject matter of the present invention is a method for selective quantitation and/or characterization of aggregates of the type DISC1 aggregates in body fluids as biomarkers for schizophrenia and other DISC1opathies. In an embodiment, testing is conducted for a further aggregate type selected from the group composed of serum amyloid A protein aggregates, IgG light chain aggregates, AapoAI aggregates, AapoAII aggregates, ATTR aggregates, FUS aggregates, IAPP aggregates, SOD1 aggregates, α-synuclein aggregates, tau aggregates, TDP-43 aggregates, huntingtin aggregates, lysozyme aggregates and Aβ aggregates, preferably FUS aggregates, SOD1 aggregates and/or TDP-43 aggregates.

In an embodiment, the subject matter of the present invention is a method for selective quantitation and/or characterization of mixed aggregates of the type DISC1 aggregates with one or more proteins selected from the group composed of serum amyloid A protein aggregates, IgG light chain aggregates, AapoAI aggregates, AapoAII aggregates, ATTR aggregates, FUS aggregates, IAPP aggregates, SOD1 aggregates, α-synuclein aggregates, tau aggregates, TDP-43 aggregates, huntingtin aggregates, lysozyme aggregates and Aβ aggregates in body fluids as biomarkers for schizophrenia and other DISC1opathies.

In an embodiment, the subject matter of the present invention is a method for selective quantitation and/or characterization of aggregates of the type FUS aggregates in body fluids as biomarkers for amyotrophic lateral sclerosis, frontotemporal lobar degeneration and other FUS proteinopathies. In an embodiment, testing is conducted for a further aggregate type selected from the group composed of serum amyloid A protein aggregates, IgG light chain aggregates, AapoAI aggregates, AapoAII aggregates, ATTR aggregates, DISC1 aggregates, IAPP aggregates, SOD1 aggregates, α-synuclein aggregates, tau aggregates, TDP-43 aggregates, huntingtin aggregates, lysozyme aggregates and Aβ-aggregate, preferably DISC1 aggregates, SOD1 aggregates and/or TDP-43 aggregates.

In an embodiment, the subject matter of the present invention is a method for selective quantitation and/or characterization of mixed aggregates of the type FUS aggregates with one or more proteins selected from the group composed of serum amyloid A protein aggregates, IgG light chain aggregates, AapoAI aggregates, AapoAII aggregates, ATTR aggregates, DISC1 aggregates, IAPP aggregates, SOD1 aggregates, α-synuclein aggregates, tau aggregates, TDP-43 aggregates, huntingtin aggregates, lysozyme aggregates and Aβ aggregates in body fluids as biomarkers for amyotrophic lateral sclerosis, frontotemporal lobar degeneration and other FUS proteinopathies.

In an embodiment, the subject matter of the present invention is a method for selective quantitation and/or characterization of aggregates of the type IAPP aggregates in body fluids as biomarkers for diabetes mellitus type 2.

In an embodiment, testing is conducted for a further aggregate type selected from the group composed of serum amyloid A protein aggregates, IgG light chain aggregates, AapoAI aggregates, AapoAII aggregates, ATTR aggregates, DISC1 aggregates, FUS aggregates, SOD1 aggregates, α-synuclein aggregates, tau aggregates, TDP-43 aggregates, huntingtin aggregates, lysozyme aggregates and Aβ aggregates.

In an embodiment, the subject matter of the present invention is a method for selective quantitation and/or characterization of mixed aggregates of the type IAPP aggregates with one or more proteins selected from the group composed of serum amyloid A protein aggregates, IgG light chain aggregates, AapoAI aggregates, AapoAII aggregates, ATTR aggregates, DISC1 aggregates, FUS aggregates, SOD1 aggregates, α-synuclein aggregates, tau aggregates, TDP-43 aggregates, huntingtin aggregates, lysozyme aggregates and Aβ aggregates in body fluids as biomarkers for diabetes mellitus type 2.

In an embodiment, the subject matter of the present invention is a method for selective quantitation and/or characterization of aggregates of the type SOD1 aggregates in body fluids as biomarkers for amyotrophic lateral sclerosis. In an embodiment, testing is conducted for a further aggregate type selected from the group composed of serum amyloid A protein aggregates, IgG light chain aggregates, AapoAI aggregates, AapoAII aggregates, ATTR aggregates, DISC1 aggregates, FUS aggregates, IAPP aggregates, α-synuclein aggregates, tau aggregates, TDP-43 aggregates, huntingtin aggregates, lysozyme aggregates and Aβ aggregates, preferably DISC1 aggregates, FUS aggregates and/or TDP-43 aggregates.

In an embodiment, the subject matter of the present invention is a method for selective quantitation and/or characterization of mixed aggregates of the type SOD1 aggregates with one or more proteins selected from the group composed of serum amyloid A protein aggregates, IgG light chain aggregates, AapoAI aggregates, AapoAII aggregates, ATTR aggregates, DISC1 aggregates, FUS aggregates, IAPP aggregates, α-synuclein aggregates, tau aggregates, TDP-43 aggregates, huntingtin aggregates, lysozyme aggregates and Aβ aggregates in body fluids as biomarkers for amyotrophic lateral sclerosis.

In an embodiment, the subject matter of the present invention is a method for selective quantitation of aggregates of the type α-synuclein aggregates in body fluids as biomarkers for Parkinson's disease and other synucleinopathies. In an embodiment, testing is conducted for a further aggregate type selected from the group composed of serum amyloid A protein aggregates, IgG light chain aggregates, AapoAI aggregates, AapoAII aggregates, ATTR aggregates, DISC1 aggregates, FUS aggregates, IAPP aggregates, SOD1 aggregates, tau aggregates, TDP-43 aggregates, huntingtin aggregates, lysozyme aggregates and Aβ aggregates.

In an embodiment, the subject matter of the present invention is a method for selective quantitation and/or characterization of mixed aggregates of the type α-synuclein aggregates with one or more proteins selected from the group composed of serum amyloid A protein aggregates, IgG light chain aggregates, AapoAI aggregates, AapoAII aggregates, ATTR aggregates, DISC1 aggregates, FUS aggregates, IAPP aggregates, SOD1 aggregates, tau aggregates, TDP-43 aggregates, huntingtin aggregates, lysozyme aggregates and Aβ aggregates in body fluids as biomarkers for Parkinson's disease and other synucleinopathies.

In an embodiment, the subject matter of the present invention is a method for selective quantitation and/or characterization of aggregates of the type tau aggregates in body fluids as biomarkers for tauopathies. In an embodiment, testing is conducted for a further aggregate type selected from the group composed of serum amyloid A protein aggregates, IgG light chain aggregates, AapoAI aggregates, AapoAII aggregates, ATTR aggregates, DISC1 aggregates, FUS aggregates, IAPP aggregates, SOD1 aggregates, α-synuclein aggregates, TDP-43 aggregates, huntingtin aggregates, lysozyme aggregates and Aβ aggregates, preferably Aβ aggregates.

In an embodiment, the subject matter of the present invention is a method for selective quantitation and/or characterization of mixed aggregates of the type tau aggregates with one or more proteins selected from the group composed of serum amyloid A protein aggregates, IgG light chain aggregates, AapoAI aggregates, AapoAII aggregates, ATTR aggregates, DISC1 aggregates, FUS aggregates, IAPP aggregates, SOD1 aggregates, α-synuclein aggregates, TDP-43 aggregates, huntingtin aggregates, lysozyme aggregates and Aβ aggregates in body fluids as biomarkers for tauopathies.

In an embodiment, the subject matter of the present invention is a method for selective quantitation and/or characterization of aggregates of the type TDP-43 aggregates in body fluids as biomarkers for amyotrophic lateral sclerosis, frontotemporal lobar degeneration, chronic traumatic encephalopathy and other TDP-43 proteinopathies. In an embodiment, testing is conducted for a further aggregate type selected from the group composed of serum amyloid A protein aggregates, IgG light chain aggregates, AapoAI aggregates, AapoAII aggregates, ATTR aggregates, DISC1 aggregates, FUS aggregates, IAPP aggregates, SOD1 aggregates, α-synuclein aggregates, tau aggregates, huntingtin aggregates, lysozyme aggregates and Aβ aggregates, preferably DISC1 aggregates, FUS aggregates and/or SOD1 aggregates.

In an embodiment, the subject matter of the present invention is a method for selective quantitation and/or characterization of mixed aggregates of the type TDP-43 aggregates with one or more proteins selected from the group composed of serum amyloid A protein aggregates, IgG light chain aggregates, AapoAI aggregates, AapoAII aggregates, ATTR aggregates, DISC1 aggregates, FUS aggregates, IAPP aggregates, SOD1 aggregates, α-synuclein aggregates, tau aggregates, huntingtin aggregates, lysozyme aggregates and Aβ-aggregates in body fluids as biomarkers for TDP-43-proteinopathies.

In an embodiment, the subject matter of the present invention is a method for selective quantitation and/or characterization of aggregates of the type huntingtin aggregates in body fluids as biomarkers for Huntington's disease. In an embodiment, testing is conducted for a further aggregate type selected from the group composed of serum amyloid A protein aggregates, IgG light chain aggregates, AapoAI aggregates, AapoAII aggregates, ATTR aggregates, DISC1 aggregates, FUS aggregates, IAPP aggregates, SOD1 aggregates, α-synuclein aggregates, tau aggregates, TDP-43 aggregates, lysozyme aggregates and Aβ aggregates.

In an embodiment, the subject matter of the present invention is a method for selective quantitation and/or characterization of mixed aggregates of the type huntingtin aggregates with one or more proteins selected from the group composed of serum amyloid A protein aggregates, IgG light chain aggregates, AapoAI aggregates, AapoAII aggregates, ATTR aggregates, DISC1 aggregates, FUS aggregates, IAPP aggregates, SOD1 aggregates, α-synuclein aggregates, tau aggregates, TDP-43-aggregates, lysozyme aggregates and Aβ aggregates in body fluids as biomarkers for Huntington's disease.

In an embodiment, the subject matter of the present invention is a method for selective quantitation and/or characterization of aggregates of the type lysozyme aggregates in body fluids as biomarkers for familial visceral amyloidosis. In an embodiment, testing is conducted for a further aggregate type selected from the group composed of serum amyloid A protein aggregates, IgG light chain aggregates, AapoAI aggregates, AapoAII aggregates, ATTR aggregates, DISC1 aggregates, FUS aggregates, IAPP aggregates, SOD1 aggregates, α-synuclein aggregates, tau aggregates, TDP-43 aggregates, huntingtin aggregates and Aβ aggregates.

In an embodiment, the subject matter of the present invention is a method for selective quantitation and/or characterization of mixed aggregates of the type lysozyme aggregates with one or more proteins selected from the group composed of serum amyloid A protein aggregates, IgG light chain aggregates, AapoAI aggregates, AapoAII aggregates, ATTR aggregates, DISC1 aggregates, FUS aggregates, IAPP aggregates, SOD1 aggregates, α-synuclein aggregates, tau aggregates, TDP-43 aggregates, huntingtin aggregates and Aβ aggregates in body fluids as biomarkers for familial visceral amyloidosis.

In an embodiment, the subject matter of the present invention is a method for selective quantitation and/or characterization of aggregates of the type Aβ aggregates and at least one further aggregate type, preferably of the type tau aggregates, in body fluids as biomarkers for Alzheimer's dementia. In an embodiment, testing is conducted for a further aggregate type selected from the group composed of serum amyloid A protein aggregates, IgG light chain aggregates, AapoAI aggregates, AapoAII aggregates, ATTR aggregates, DISC1 aggregates, FUS aggregates, IAPP aggregates, SOD1 aggregates, α-synuclein aggregates, TDP-43 aggregates, huntingtin aggregates and lysozyme aggregates.

A standard used for the selective quantitation and/or characterization of the indicators containing a polymer, composed of monomer sequences that are identical in sequence to a partial region of the endogenous proteins or show homology of at least 50% over the corresponding partial region, wherein these polymers do not aggregate and the endogenous proteins are those that aggregate, is also the subject matter of the present invention.

A standard within the meaning of the present invention refers to a generally valid and accepted, fixed reference value, which is used for comparing and determining properties and/or amounts, particularly for determining the size and amount of (pathogenic) aggregates of endogenous (misfolded) proteins. The standard within the meaning of the present invention can be used for calibrating equipment and/or measurements.

It is of essential importance for the standards according to the invention that the standards do not aggregate, preferably by using monomer sequences that do not aggregate because the corresponding partial region of endogenous proteins is not responsible for aggregation, or which do not aggregate due to blocking of the groups responsible for aggregation.

In this sense, the term "monomer sequence" as used here refers to a partial region, a fragment of the individual proteins (monomers) that form aggregates of misfolded proteins.

In an embodiment, the partial region is an epitope or a homolog showing at least 50% identity thereto and the biological activity of an epitope, preferably of an epitope contained in one of the SEQ ID Nos.: 1-15.

A monomer sequence selected in this manner is incorporated in the desired number in constructing the standards according to the invention and/or linked to one another according to the invention.

The standards according to the invention are polymers composed of the above-described monomer sequences, preferably epitopes, optionally containing further elements.

In a further embodiment of the present invention, the above-described monomer sequences, preferably epitopes, and/or homologs thereof having the biological activity of the corresponding epitope and the same or the largest number of monomers relative to the respective number of one of the remaining monomer species of the standards and/or relative to the number of all other monomers.

The standard molecule according to the invention is a polymer of the above-defined monomer sequences. Oligomer within the meaning of the invention is a polymer composed of a 2, 3, 4, 5, 6, 7, 8, 9, 10, 11, 12, 13, 14, 15, 16, 17, 18, 19 or 20-monomer sequence, or multiples thereof, preferably 2-16, 4-16, 8-16, particularly preferably 8 or 16, or multiples thereof.

In an alternative of the present invention, the standards are water-soluble.

In an alternative of the present invention, the standards according to the invention are composed of identical monomer sequences.

In an alternative of the present invention, the standards according to the invention are composed of different monomer sequences.

In an alternative of the present invention, such aforementioned monomer sequences are arranged side by side in a linear conformation.

In an alternative of the present invention, such aforementioned monomer sequences are arranged side by side to form a branched oligomer according to the invention.

In an alternative of the present invention, such aforementioned monomer sequences are arranged side by side to form a cross-linked oligomer according to the invention.

Branched or cross-linked oligomers according to the invention can be produced by joining individual components using lysine or by means of click chemistry.

As described above, the standards according to the invention, i.e. the oligomers or polymers according to the invention, may also comprise, in addition to the monomer sequences, preferably epitopes, present in a precisely defined number, additional amino acids, spacers and/or functional groups, by means of which the monomer sequences, preferably epitopes, are covalently linked to one another.

In an alternative, direct linking of the monomer sequences, preferably epitopes with cysteine, in particular by means of disulfide bridging via cysteine, is excluded (in order to prevent reducing agents from dissolving the bridges). Moreover, in a further variant, direct linking of the spacers to the monomer sequence on the one hand and to cysteine on the other is excluded.

The duplication of the epitopes by means of functional groups can be carried out before or after synthesis of the individual components.

Characteristic for the standards according to the invention is covalent linking of the monomer sequences.

The monomer sequences to be used according to the invention can be identical to the sequence of a protein or show a homology of 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% with the sequence of one of the full-length proteins that form aggregates.

Alternatively, monomer sequences are used according to the invention to construct standard molecules that are identical with a partial region of a full-length protein or show a homology of 50, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% with a partial region of a full-length protein.

Of essential importance for the sequences used according to the invention is their property of not aggregating (or doing so only in a controlled manner according to the conditions) and/or their activity as epitopes.

In an alternative, the standards advantageously show higher water-solubility than pathogenic aggregates or oligomers of endogenous proteins.

In an embodiment of the present invention, the standards have a precisely defined number of epitopes that are covalently linked to one another (directly or via amino acids, spacers and/or functional groups) for binding of the corresponding binding partners.

In this sense, with respect to the standards, binding partners are selected from the group composed of antibodies, nanobodies and affibodies. Binding partners are also all molecules having sufficient binding affinity for the aggregates to be detected, e.g. dyes (thioflavin T, Congo red, etc.).

A standard molecule according to the invention can contain epitopes for at least 2, 3, 4, 5, 6, 7, 8, 9, 10 or more different binding partners.

Epitopes characteristic for different binding partners can be incorporated into the standards according to the invention by using monomer sequences that are identical to different regions of one or different proteins (that form aggregates of misfolded proteins), or show at least 50% homology therewith but have the activity of the corresponding epitope.

In an embodiment of the present invention, the standard molecules contain what are referred to as spacers.

A spacer is understood to be a molecule that is incorporated into the standard molecule via covalent links and possesses certain physical and/or chemical properties, by means of which the properties of the standard molecule are changed. In an embodiment of the standards according to the invention, hydrophilic or hydrophobic, and preferably hydrophilic spacers are used. hydrophilic spacers are selected from the group of molecules composed of polyethylene glycol, sugar, glycerin, poly-L lysine or β-Alanine. In an alternative of the present invention, the standards according to the invention contain (further) functional groups.

Functional groups are understood to refer to molecules that are covalently bonded to the standard molecules. In a variant, the functional groups contain biotin groups. This enables strong covalent binding to streptavidin. Standard molecules containing biotin groups can therefore be bonded to molecules containing streptavidin groups. If the standard molecules according to the invention contain biotin and/or streptavidin groups, this allows larger standards to be constructed or several, optionally different standard molecules to be bonded to a scaffold.

In a further alternative of the present invention, the standard molecules contain dyes for spectrophotometric determination and/or aromatic amino acids. Aromatic amino acids are e.g. tryptophan, tyrosine, phenylalanine or histidine, or can be selected from these groups. Incorporation of tryptophan allows spectrophotometric determination of the concentration of standards in solution.

In a further embodiment of the present invention, the standards are constructed as dendrimers. The dendrimers according to the invention are made up of the above described monomer sequences to be used according to the invention and can contain a central scaffold molecule. The scaffold molecule is preferably a streptavidin monomer, and particularly preferably a polymer, particularly a tetramer.

In a variant, the dendrimers according to the invention contain monomer sequences possessing a sequence that is identical to a partial region of the proteins, or shows at least 50% homology with the corresponding partial region.

According to the invention, the term at least 50% homology is also understood to refer to a higher homology selected from the group composed of 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100%.

Dendrimers containing polypeptides whose sequence is identical in the corresponding partial region to the endogenous proteins or show a homology of at least 50% over the corresponding partial region with the endogenous proteins are also the subject matter of the present invention.

The dendrimers according to the invention can comprise any of the above-described characteristics of the standards or any desired combination thereof.

An alternative of the present invention comprises:
a dendrimer containing a precisely defined number of epitopes for the covalent binding of binding partners,
a dendrimer containing epitopes of one or more of the proteins that form aggregates of misfolded proteins, preferably according to SEQ ID NOs: 1-15,
a dendrimer, characterized by having higher water solubility than the pathogenic aggregates of endogenous proteins,
a dendrimer containing functional groups,
a dendrimer containing at least one spacer molecule and/or
a dendrimer containing dyes for spectrophotometric determination and/or aromatic amino acids.

According to the invention, the dendrimers have radial symmetry.

In a variant, branching of the first generation of dendrimers takes place via lysine, in particular three lysine amino acids.

In a further alternative of the present invention, in the standards, in particular dendrimers, the polypeptide sequences, preferably epitopes, are not linked via a bond to a sulfur atom, via a thioether bond and/or not via cysteine (optionally by means of disulfide bridging by cysteine) to one another or to other elements of the standards such as amino acids, spacers and/or functional groups and/or other above-described elements, particularly not covalently bonded. Moreover, in a further variant, the polypeptide sequences, preferably epitopes, and a spacer bonded thereto, are not linked on the spacer via a bond to a sulfur atom, via a thioether bond and/or via cysteine to one another or to other elements of the standards such as amino acids, further spacers and/or functional groups and/or other above-described elements, particularly not covalently bonded.

The present invention further concerns a method for production of a standard as described above.

In an embodiment, the standard according to the invention is produced by means of a peptide synthesis or recombinant method known to the person having ordinary skill in the art.

The use of an above-described standard or an above-described dendrimer for quantitation of pathogenic aggregates or oligomers of endogenous proteins is also the subject matter of the present invention.

According to the invention, the standards according to the invention are used in a method for the quantitation of pathogenic aggregates or oligomers of endogenous proteins.

The standards according to the invention are used in an embodiment of the present invention for calibration in the surface FIDA method (sFIDA), ELISA (sandwich ELISA) or FACS.

In a further embodiment, the present invention concerns a kit that comprises a standard according to the invention. The compounds and/or components of the kit of the present invention can be packed in containers, optionally with/in buffer and/or solution. Alternatively, some components can be packed in the same container. In addition or alternatively thereto, one or more of the components can be absorbed on a solid carrier such as a glass plate, chip or nylon membrane, or the recess of a microtiter plate.

Such a kit can contain one or more of the following components:
substrate of glass coated with a hydrophobic substance, preferably dextran, preferably carboxymethyldextran or polyethylene glycol, and preferably heterobiofunctional polyethylene glycol (NHS-PEG-COOH);
standard;
capture molecule;
probe;
substrate with capture molecule.

The kit can also contain instructions for use of the kit for any of the embodiments desired.

In an alternative of the present invention, the standards for quantitation of pathogenic aggregates or oligomers of endogenous proteins are used, wherein:
in a first step, the standards or the dendrimers are labeled with binding partners and the number of binding partners bonded to the standards or dendrimers is determined,
in a second step, pathogenic aggregates or oligomers of endogenous proteins are labeled with probes, and the number of probes binding to one respective pathogenic aggregate or oligomer each is determined,
in a third step, the number of binding partners binding to one standard or dendrimer each from step 1 is compared with the number of probes binding to one aggregate from step 2, and
in a fourth step, the number and the size of the oligomers from the body fluid is thus determined.

In a variant of the present invention, the standards according to the invention, preferably dendrimers, are used for calibration of the surface FIDA method. In a first step, endogenous pathogenic aggregates from body fluids are immobilized on a glass surface. After immobilization, the aggregates are labeled with two different probes. The detection probes are preferably labeled with different fluorescent dyes. This makes them visible under the microscope, e.g. a laser scanning microscope.

The standards according to the invention can also be used as capture molecules and/or probes, or parts thereof. Capture molecules and/or probes containing the standards according to the invention are therefore also the subject matter of the present invention.

The subject matter of the present invention is a substrate comprising precisely defined regions with capture molecules for the disease indicators and/or aggregates.

This substrate is used in a method for the diagnosis of a disease selected from the group composed of Alzheimer's dementia, AA amyloidosis, AL amyloidosis, AapoAI amyloidosis, AapoAII amyloidosis, ATTR amyloidosis, schizophrenia and other DISC1opathies, amyotrophic lateral sclerosis, frontotemporal lobar degeneration and other FUS proteinopathies, diabetes mellitus type 2, Parkinson's disease and other synucleinopathies, tauopathies, chronic traumatic encephalopathy and other TDP-43 proteinopathies, Huntington's disease, familial visceral amyloidosis and/or Alzheimer's dementia.

All process steps after removal of the sample are carried out ex vivo (in vitro), i.e. outside of the human or animal body.

The sample can be taken from a human or an animal. Aggregate types of endogenous misfolded proteins are found in the following diseases and can be used as biomarkers or parts of a biomarker: Table A, lines 1-15.

TABLE A

| | Biomarker or part thereof | Disease |
|---|---|---|
| 1 | Serum amyloid A protein aggregates | AA amyloidosis |
| 2 | IgG light chain aggregates | AL amyloidosis |
| 3 | AApoAI aggregates | AApoAI amyloidosis |
| 4 | AApoAII aggregates | AApoAII amyloidosis |
| 5 | ATTR aggregates | ATTR amyloidosis |
| 6 | DISC1 aggregates | Schizophrenia and other DISC1opathies |
| 7 | FUS aggregates | Amyotrophic lateral sclerosis, frontotemporal lobar degeneration and other FUS proteinopathies |
| 8 | IAPP aggregates | Diabetes mellitus type 2 |
| 9 | SOD1 aggregates | Amyotrophic lateral sclerosis |
| 10 | α-synuclein aggregates | Parkinson's disease and other synucleinopathies |
| 11 | Tau aggregates | Tauopathies |
| 12 | TDP-43 aggregates | Amyotrophic lateral sclerosis, frontotemporal lobar degeneration, chronic traumatic encephalopathy and other TDP-43 proteinopathies |
| 13 | Huntingtin aggregates | Huntington's disease |
| 14 | Lysozyme aggregates | Familial visceral amyloidosis |
| 15 | Aβ aggregates | Alzheimer's dementia |

In an embodiment of the present invention, a biomarker of Table A is also to be used as a disease indicator for a disease of Table A other than those shown in the same cell of the biomarkers in the table.

For example, tau aggregates, or as shown in the table, DISC1 aggregates, FUS aggregates, α-synuclein aggregates, and tau aggregates or TDP-43 aggregates for different diseases can be used as biomarkers for Alzheimer's dementia.

For example, mixed aggregates, for example composed of tau and α-synuclein, can be used as biomarkers for e.g. Parkinson's disease. Other mixed aggregates can also be used as biomarkers.

Therefore, not only is it possible to diagnose combinations of diseases, but other diseases can also be excluded based on these results. This also makes a more precise diagnosis possible.

The subject matter of the present invention is a differential diagnostic method for determining diseases that exhibit aggregates of misfolded proteins comprising the following steps:

i) determination of the amount of misfolded protein aggregates in a sample in a method comprising:

a) taking the sample from a human or animal body, and optionally, pretreatment and application of the sample to be tested to a substrate, b) addition of probes labeled for detection that label the respective aggregate by specifically binding to it and c) detection of the labeled aggregates, wherein step b) can be carried out before step a) and the disease is selected from the group composed of AA amyloidosis, AL amyloidosis, AApoAI amyloidosis, AApoAII amyloidosis, ATTR amyloidosis, schizophrenia and other DISC1opathies, amyotrophic lateral sclerosis, frontotemporal lobar degeneration and other FUS proteinopathies, diabetes mellitus type 2, Parkinson's disease and other synucleinopathies, tauopathies, chronic traumatic encephalopathy and other TDP-43 proteinopathies, Huntington's disease, familial visceral amyloidosis and/or Alzheimer's dementia;

ii) comparison of these data with the standard values;

iii) detection of a significantly higher amount of protein aggregates in this comparison;

iv) attribution of the discrepancy to a disease according to the disease indicators.

Specific capture molecules that bind to two different aggregates of endogenous proteins are immobilized on the substrate according to the invention in at least two precisely defined regions. In an alternative, 3, 4, 5, 6, 7, 8, 9, 10, 11, 12, 13, 14, 15, 16 or more different specific capture molecules are immobilized on the substrate in precisely defined regions. A differential diagnosis can therefore be carried out according to the binding and subsequent detection of the aggregates.

In an alternative, 16 or more different capture molecules per well can be applied (spotted) onto defined subsurfaces. Different aggregate types and even heterogeneous aggregates of different monomers can thus be identified in a single sample. Small amounts of body fluids are therefore sufficient. Moreover, the grid position can also be used to identify the aggregates.

In an alternative, a mixture of different capture antibodies can be immobilized in a single substrate (well), or using a "spotting" method, different capture molecules (e.g. antibodies) that for example specifically bind one or more of the probes or specifically bind one or more of the aggregated proteins can be applied to different positions within a single surface, e.g. the bottom of a microtiter plate well. By using different probes, each carrying different a different fluorophore, different aggregate species can therefore be analyzed almost simultaneously in a single sample aliquot.

In this way, aggregate-mixed forms consisting of different protein monomers can also be identified.

Therefore, it is not only possible to diagnose combinations of diseases, but other diseases can also be excluded based on these results. This also makes a more precise diagnosis possible.

An advantage of the method according to the invention is that by means of a single patient sample comprising a number of entities accompanying protein aggregates, it is possible to test for all possible aggregate types that are based on endogenous misfolded proteins. Another advantage is the possibility of directly testing protein aggregates for aggregate types ex vivo in samples such as blood and cerebrospinal fluid samples or urine, saliva, mucosa, or biopsy material, particularly blood and cerebrospinal fluid samples.

By means of the method according to the invention, new disease indicators can be qualitatively and/or quantitatively determined. Disease indicators or biomarkers, characterized by the presence of an aggregate type of endogenous misfolded proteins that are tested for according to the invention, and optionally, by the presence and/or absence of at least one further aggregate type, are therefore also the subject matter of the present invention.

By means of the method according to the invention and the new biomarkers, one of the diseases based on misfolded protein aggregates (as mentioned above) can be identified and clearly differentiated from the other diseases of the group, optionally with similar or consistent symptoms.

A biomarker determined by means of the method according to the invention, which is selected based on the presence of at least one aggregate type of endogenous misfolded proteins from the group consisting of serum amyloid A protein aggregates, IgG light chain aggregates, AapoAI aggregates, AapoAII aggregates, ATTR aggregates, DISC1 aggregates, FUS aggregates, IAPP aggregates, SOD1 aggregates, α-synuclein aggregates, tau aggregates, TDP-43 aggregates, huntingtin aggregates, lysozyme aggregates and Aβ aggregates or aggregate mixed forms thereof and optionally based on the presence and/or absence of at least one more of the above-mentioned aggregate types or aggregate mixed forms is therefore also the subject matter of the present invention.

The method according to the invention can further be used to set the limit values of the concentration of protein aggregates that are relevant for a disease or the diagnosis of a disease.

The subject matter of the present invention is a kit for differential diagnosis containing one or more of the following components:
  substrate as described above,
  standard as described above,
  probe,
  solutions,
  buffer,
wherein the disease is selected from the group composed of AA amyloidosis, AL amyloidosis, AApoAI amyloidosis, AApoAII amyloidosis, ATTR amyloidosis, schizophrenia and other DISC1opathies, amyotrophic lateral sclerosis, frontotemporal lobar degeneration and other FUS proteinopathies, diabetes mellitus type 2, Parkinson's disease and other synucleinopathies, tauopathies, chronic traumatic encephalopathy and other TDP-43 proteinopathies, Huntington's disease, familial visceral amyloidosis and/or Alzheimer's dementia.

The use of the method according to the invention for the diagnosis, early diagnosis and/or prognosis of the above-mentioned diseases is also the subject matter of the present invention.

The use of the method according to the invention for monitoring therapies of the above-mentioned diseases, as well as monitoring and/or testing the efficacy of active ingredients and/or treatment procedures is also the subject matter of the present invention. This can be used in clinical tests, studies, and in treatment monitoring. For this purpose, samples are measured by the method according to the invention and the results are compared.

The use of the method according to the invention and biomarkers to determine whether a person is enrolled in a clinical study is also the subject matter of the present invention. For this purpose, samples are measured by the method according to the invention, and the decision is made based on a limit value.

A method for determining the efficacy of active ingredients and/or treatment procedures by means of the method according to the invention, in which the results of samples are compared to one another is also the subject matter of the present invention. The samples are body fluids taken before, after, or at different times after administration of active ingredients or conducting the treatment procedure. Based on the results, active ingredients and/or treatment procedures that reduced the aggregates are selected. According to the invention, results are compared to a control that did not receive the active ingredient and/or undergo the treatment procedure.

BRIEF DESCRIPTION OF THE DRAWINGS

The accompanying drawings graphically represent results of the sFIDA assays described below under the headings "3. Use with aggregates of recombinant protein", "4. Use on native samples" and "5. Differential diagnostic use of sFIDA". In particular.

DETAILED DESCRIPTION OF EMBODIMENTS OF THE PRESENT INVENTION

Examples

1. Materials and Methods

Figure 1A:
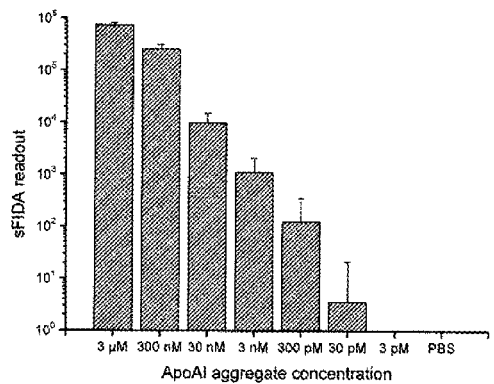
FIGS. 1A to 1F show sFIDA readouts at various concentrations of different protein aggregates.
Figure 1B:
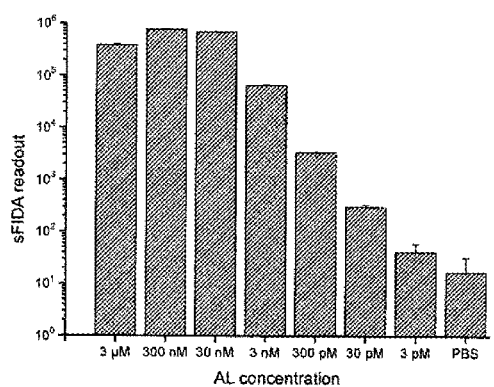
Figure 1C:
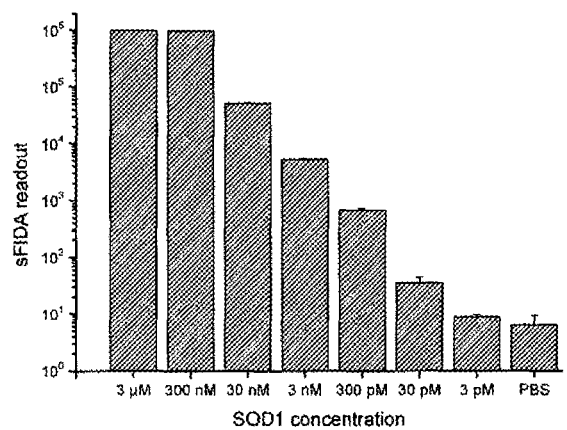
Figure 1D:
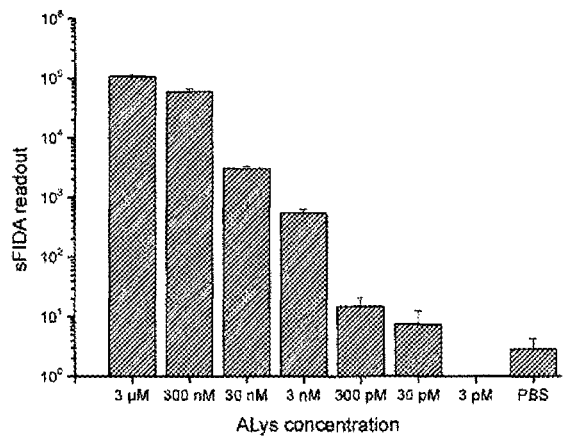
Figure 1E:
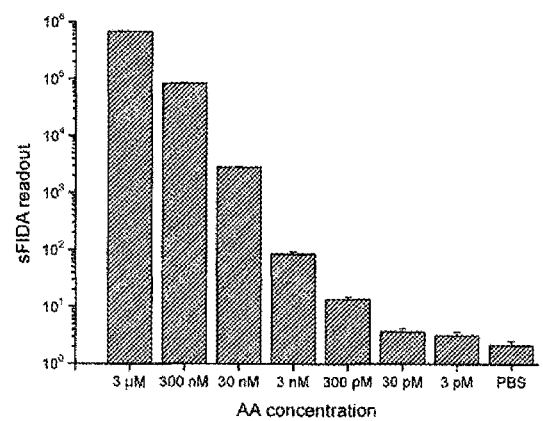
Figure 1F:
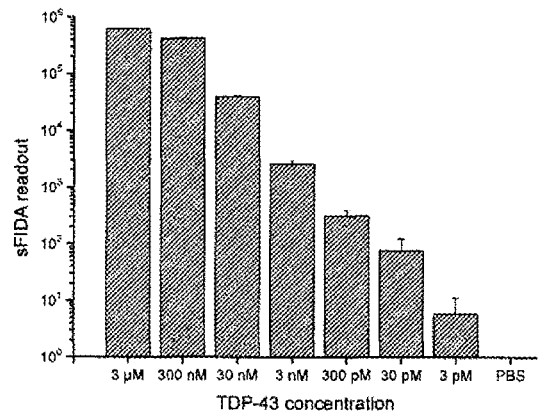

In the assay, multiwell plates with a 170 μm thick glass bottom were used as sample carriers (SensoPlate Plus 384 Greiner Bio-One, Kremsmünster, Austria). All reagents and solutions used were obtained with the highest degree of purity and sterilized until particle-free prior to use.

In the first step, each sample chamber (well) was filled with 100 μL sodium hydroxide solution (5 M), incubated for 15 minutes at room temperature, rinsed three times with water, mixed with 100 μL hydrochloric acid and again incubated for 15 minutes at room temperature. After washing thee times with water and twice with ethanol, the wells were dried under a nitrogen atmosphere.

In order to produce amino groups on the glass surface, 20 μL of ethanolamine (5.6 M) was placed in each of the wells and incubated overnight at room temperature. The wells were washed three times with DMSO, twice with ethanol, and dried under a nitrogen atmosphere.

Heterobiofunctional polyethylene glycol (NHS-PEG-COOH, MW 3.400 Da) was dissolved to 50 mM in DMSO at 70° C. for 1 min, cooled to room temperature, and adjusted with 2% triethylamine. 15 μL of this solution was added to each of the wells, and incubation was carried out for at least one hour at room temperature. The solution was removed from the wells, and the wells were washed three times with water.

In order to activate the PEG coating, NHS and EDC (carbodiimide) were diluted to 100 mM each in MES buffer (0.1 M, pH 5, MES: 2-N-morpholinoethanesulfonic acid) and mixed in a 1:1 ratio to final concentrations of 50 mM respectively. 30 μL each of this solution was added to the wells and incubated for 30-60 minutes. After removal of the solution, the wells were washed three times with MES buffer (0.1 M, pH 5).

The capture antibodies were diluted to 30 ng/µL in PBS. 15 µL of this solution was added to the wells and incubated for 1-3 hours at room temperature. The solution was then removed, and washing was carried out three times with PBST (PBS with Tween 20) and then three times with PBS.

3% BSA was first centrifuged at 100,000 g (1 hour at 4° C.). 50 µL each of the supernatants was added to the wells and incubated for one hour at room temperature. The BSA solution was removed, and washing was carried out three times with PBST.

The sample (e.g. aggregates of recombinant protein and natural patient sample) was—if necessary—diluted in PBS, 15 µL each of this solution was added to the wells. The multiwell plate was centrifuged at 1,000 g for one hour at 4° C. in a swing-out centrifuge. The supernatant was removed and the wells were washed three times with PBST and three times with PBS.

Fluorescence-labeled antibodies were used as detection probes. These were diluted to 1-2 ng/µL in PBS and mixed with 1.5% BSA. The batches were centrifuged at 100,000 g for one hour at 4° C. 15 µL each of the supernatant was placed in the wells and incubated for 1-2 hours at room temperature. The solution was then removed and washing was carried out five times with PBST and five times with PBS.

The surface fluorescence was visualized by total internal reflection fluorescence microscopy (TIRFM). Alternatively, the protein particles can be visualized by confocal laser scanning at the level of the glass surface. Up to 50 individual images per well (1000×1000 pixels, 114 nm/pixel) were taken per fluorescence channel with a high-sensitivity CCD camera.

Background signals in the image data were removed by applying an intensity threshold. The mean number of pixels with grayscale values above the threshold was determined (sFIDA readout). If several detection probes were used, only the events colocalized in all fluorescence channels were evaluated.

2. sFIDA Protocol
2.1. Pretreatment
15 min NaOH (5M) 100 µL/well
3×H$_2$O
15 min HCl (1M) 100 µL/well
3×H$_2$O
rinse 2×EtOH rinse
dry with N$_2$
2.2. Glass Activation (Amino Groups)
20 µL/well ethanolamine (5.6 M) [x] incubation ON (overnight) room temperature or longer 4° C.
3×DMSO
2×EtOH
dry with N$_2$
2.3. Spacer NHS-PEG-COOH
(briefly) dissolve 17 mg PEG in 100 µL DMSO at 70° C., allow to cool, 2 µL triethylamine (TEA)
15 µL/well [x] incubation: min. 1 h
3×H$_2$O
2.4. PEG Activation with NHS/EDC (50 mM)
dilute 5.8 mg NHS and 9.6 mg EDC in 500 µL MES (0.1M), directly apply 1:1 mixing
30 µL well [x] incubation: 30 min-max. 1 h
quickly 3×MES (0.1 M)
2.5 Capture
dilute capture antibodies in PBS (30 ng/µL)
15 µL well→incubation 1-3 h RT or longer 4° C.
3×PBST, 3×PBS
2.6. Blocking
3% BSA 1 h at 100,000×g, 4° C. (Rotor TLA-45)
50 µl/well [x] incubation 1 h
3×PBST
3×PBS
  Day 2
2.7. Target
15 µL target, diluted in PBS
incubation 1 h centr., 1000 g, 25° C.,
HH: 3×0.2% SDS/PBS; 5×PBST; 5×PBS
plasma and recombinant aggregates: 3×PBST; 3×PBS
2.8. Detection Antibodies
1-2 ng/µL in 1.5% BSA with PBS after 100,000×g, 4° C. (Rotor TLA-45)
15 µL each of supernatant/well [x] incubation>=1-2 h, RT
5×PBST
5×PBS
(100 µL of the corresponding solution each was used for washing steps)

3. Use with Aggregates of Recombinant Protein

The basic feasibility of the sFIDA assay for detection of different aggregate species was first demonstrated. As examples, aggregates of different proteins (AapoAI, AL, SOD1, ALys, AA, TDP-43) were prepared, and corresponding dilution series were tested in an sFIDA assay. In this case, the same antibodies directed against the specific protein respectively were used as capture and detection antibodies. Each detection probe was labeled with Alexafluor 488. All of the aggregates were detectable in a concentration-dependent manner to the picomolar range by means of sFIDA.

FIG. 1A-F: sFIDA of different protein aggregates. The protein aggregates were diluted in the indicated concentrations in PBS buffer and analyzed by sFIDA assay. PBS buffer was used as a negative control. A) ApoAI, capture and detection probe (AF488-labeled) EPR 1368Y; B) AL, capture and detection probe (AF488-labeled) EPR 5367; C) SOD1, capture and detection probe (AF488-labeled) EPR 1726; D) ALys, capture and detection probe (AF488-labeled) EPR 2994 (2); E) AA, capture and detection probe (AF488-labeled) EPR 4134; F) TDP-43, capture and detection probe (AF488-labeled) EPR 5810.

4. Use on Native Samples

In order to demonstrate in an illustrative manner that protein aggregates can be detected in blood and cerebrospinal fluid samples (CSF samples) or urine, saliva, mucosa, or biopsy material, protein aggregates (α-synuclein and DISC1) were diluted in CSF and analyzed by sFIDA. For the detection of α-synuclein, anti-αSyn-Aβ 2B2A11 was used as a capture antibody, and fluorescence-labeled anti-αSyn-ABs 3H2897-AF633 or 211-AF488 were used as detection probes. For detection of DISC1 aggregates, anti-DISC1-AK 14F2 was used as a capture antibody and 14F2-AF633 as a detection probe. Both synuclein and DISC1 aggregates can be detected in a concentration-dependent manner to the picomolar range by means of sFIDA (see FIGS. 2A and B).

Figure 2A:
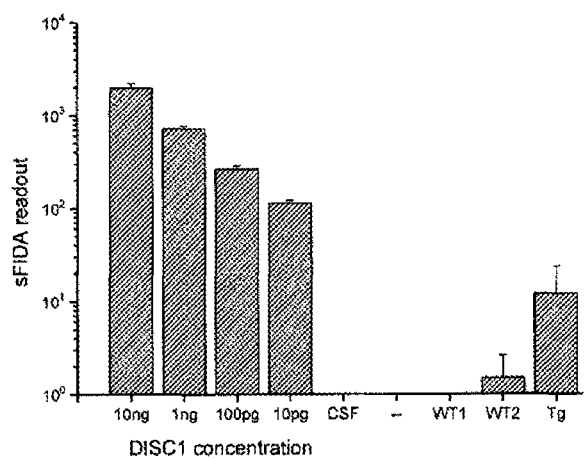
FIGS. 2A and 2B show sFIDA readouts of protein aggregates in cerebrospinal fluid samples.

In order to investigate the molecular basis of schizophrenia, a rat model was developed at the laboratory of Carsten Korth that strongly expresses the protein DISC1. In order to test whether this protein is natively present in aggregates, CSF samples from a transgenic animal were analyzed by sFIDA. Compared to two controls, the transgenic sample showed a clearly elevated titer of DISC1 aggregates (FIG. 2A, samples WT1, WT2, Tg).

Figure 2B:
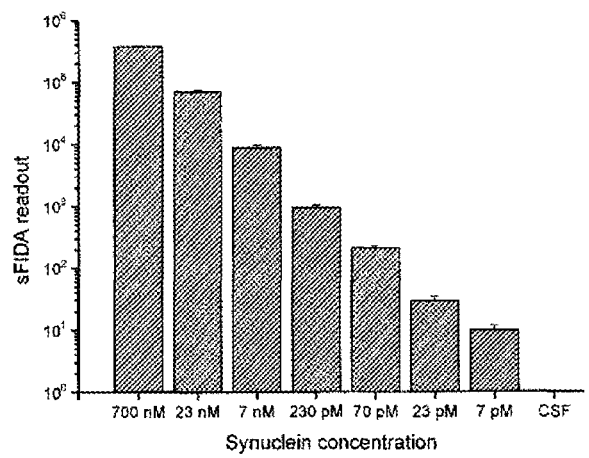

FIG. 2: sFIDA detection of protein aggregates in CSF. Aggregates of recombinant protein were diluted in human CSF and tested in an sFIDA assay. A) DISC1 detection. mAβ 14F2 was used as a capture antibody and detection probe (AF633-labeled). In addition to recombinant DISC1 aggregates (10 pg-10 ng) CSF samples from rats (WT1, WT2, Tg) were subjected to sFIDA analysis. B) Synuclein detection by means of 2D sFIDA. Anti-αSyn-Aβ 2B2A11 was used as a capture antibody and fluorescence-labeled anti-αSyn-ABs 3H2897-AF633 or 211-AF488 were used as detection probes. Only the signals colocalized in both fluorescence channels above a threshold values were taken into consideration.

5. Differential Diagnostic Use of sFIDA

A sample was distributed to different reaction chambers (wells) coated with different capture antibodies. Alternatively, a mixture of different capture antibodies can be immobilized in a single well, or different capture antibodies can be applied using a "spotting" method to different positions within a single surface, e.g. the bottom of a microtiter plate well.

By using different probes, each carrying a different fluorophore, different aggregate species were therefore analyzed almost simultaneously in a single sample aliquot.

Figure 3:
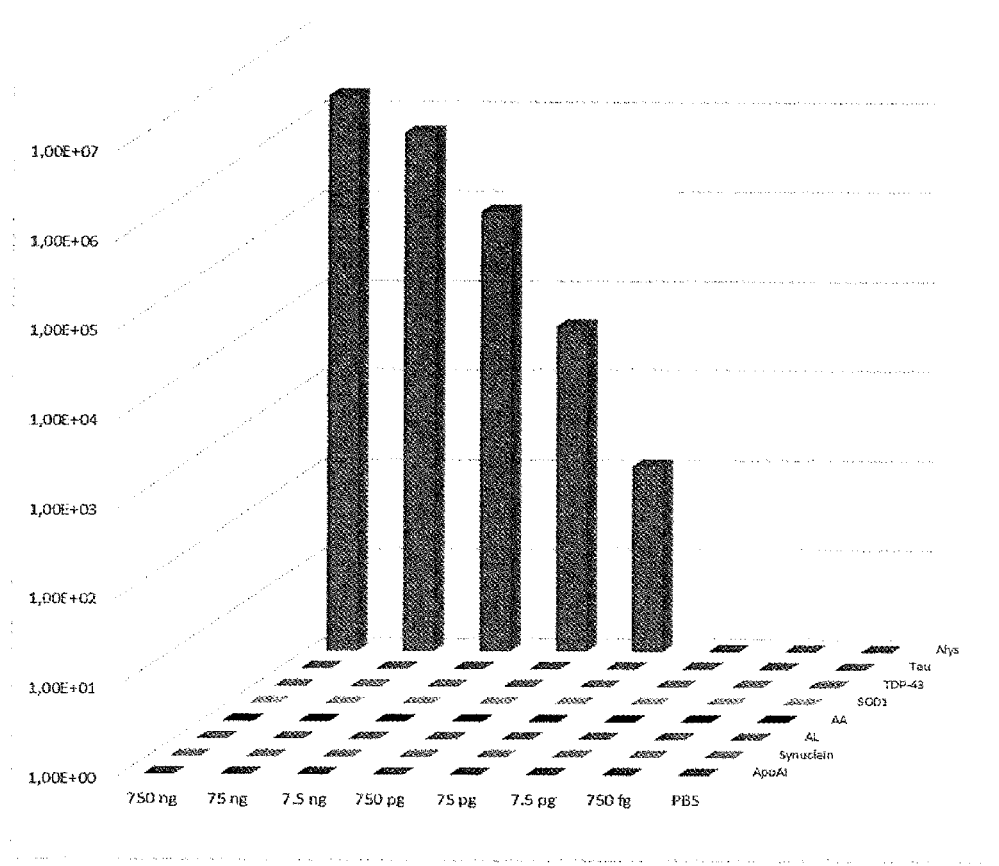
FIG. 3 shows the results of a specificity (cross-reactivity) analysis in an ALys-specific sFIDA assay carried out with recombinant ALys aggregates of other protein aggregates.

It was shown in this example that an ALys-specific sFIDA assay (anti-lysozyme antibody as probe and capture antibody) shows no cross-reactivity with other protein aggregates over a broad concentration range (FIG. 3). Anti-lysozyme antibodies used as probes and capture antibodies interact only with aggregates of the type ALys.

In a further example, it was shown that the presence of other proteins does not adversely effect the detectability of amyloid beta aggregates. For this purpose, a mixture of amyloid-beta aggregates and tau aggregates was subjected to sFIDA analysis.

FIG. 3. Specificity analysis. In an ALys-specific sFIDA assay with capture antibodies, rabbit monoclonal EPR2994 (2) and detection probe EPR2994(2)-AF488, as well as a dilution of recombinant ALys aggregates of other protein aggregates (tau, TDP-43, SOD1, AA, AL, synuclein, ApoAI) were tested for cross-reactivity.

Figure 4:
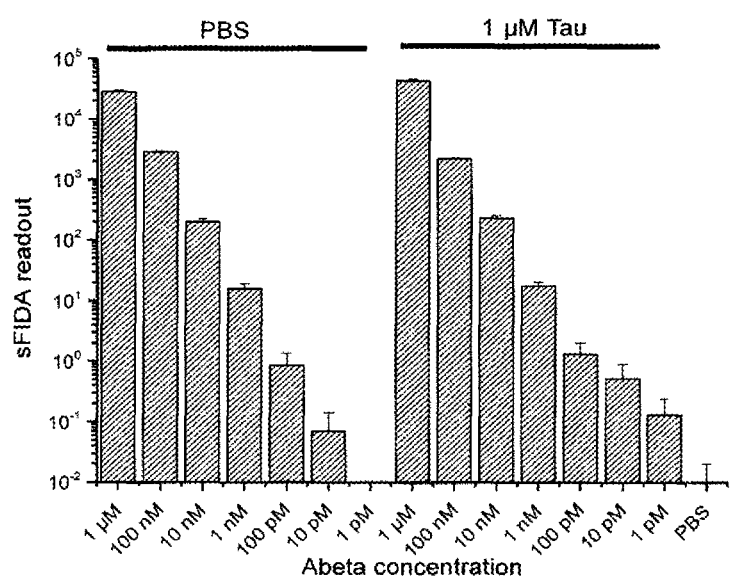
FIG. 4 shows Aβ-specific sFIDA readouts at various concentrations in the presence and absence of tau protein.

FIG. 4: Aβ-specific sFIDA in the presence of tau protein. Protein aggregates of Aβ were diluted in the indicated concentrations and analyzed with and without the presence of 1 μM tau protein aggregate by Aβ-specific sFIDA assay (detection probe 6E10/Atto488, capture antibody Nab228).

What is claimed is:

1. A method for the qualitative and/or quantitative determination of disease indicators in which a sample is tested for at least two aggregate types of endogenous misfolded proteins, wherein the sample is tested for at least two different aggregate types on the same substrate without further processing and/or treatment and the method comprises:

(a) application of the sample to be tested to a substrate,
(b) addition of probes labeled for detection with fluorescent dyes, which probes label a respective aggregate by specifically binding to it, and
(c) detection of labeled aggregates by surface-based Fluorescence Intensity Distribution Analysis (sFIDA), carried out by a method with a temporally and spatially resolved signal and with high spatial resolution wherein a pixel is determined against a respective background, and wherein
(b) can be carried out before (a);
the disease is selected from tauopathies, AA (amyloid A) amyloidosis, AL (amyloid light chain) amyloidosis, AApoAI (amyloid apolipoprotein AI) amyloidosis, (amyloid apolipoprotein AII) AApoAII amyloidosis, ATTR (amyloid transthyretin) amyloidosis, schizophrenia and other DISC1 (disrupted in schizophrenia 1) opathies, amyotrophic lateral sclerosis, frontotemporal lobar degeneration and other FUS (fused in sarcoma) proteinopathies, diabetes mellitus type 2, Parkinson's disease and other synucleinopathies, chronic traumatic encephalopathy and other TDP-43 (transactive response DNA binding protein 43 kDa) proteinopathies, Huntington's disease, familial visceral amyloidosis and/or Alzheimer's dementia; and
the aggregate type of endogenous misfolded proteins is selected from tau aggregates, serum amyloid A protein aggregates, IgG (immunoglobulin G) light chain aggregates, AapoAI aggregates, AapoAII aggregates, ATTR aggregates, DISC1 aggregates, FUS aggregates, IAPP (islet amyloid polypeptide) aggregates, SOD1 (superoxide dismutase 1) aggregates, α-synuclein aggregates, TDP-43 aggregates, huntingtin aggregates, lysozyme aggregates, Aβ aggregates, and mixed aggregates.

2. The method of claim 1, wherein prior to (a) capture molecules are immobilized on the substrate.

3. The method of claim 1, wherein capture molecules immobilized on the substrate and/or the probes comprise specific antibodies to an epitope of the proteins which form the aggregates.

4. The method of claim 1, wherein the sample is tested for at least three aggregate types of endogenous misfolded proteins.

5. The method of claim 1, wherein the method is a method for a differential diagnosis of a disease selected from tauopathies, AA amyloidosis, AL amyloidosis, AApoAI amyloidosis, AApoAII amyloidosis, ATTR amyloidosis, schizophrenia and other DISC1opathies, amyotrophic lateral sclerosis, frontotemporal lobar degeneration and other FUS proteinopathies, diabetes mellitus type 2, Parkinson's disease and other synucleinopathies, chronic traumatic encephalopathy and other TDP-43 proteinopathies, Huntington's disease, familial visceral amyloidosis and/or Alzheimer's dementia vs. another disease selected from the above-mentioned diseases and comprises:

(i) quantitative determination of disease indicators according to claim 1;
(ii) comparison of obtained data with standard values;
(iii) detection of a significantly different quantity of disease indicators as discrepancy in the comparison; and
(iv) attribution of the discrepancy to a disease selected from the above-mentioned diseases.

6. The method of claim 1, wherein the method is a method for a differential diagnosis and wherein after a quantification of a disease indicator for a disease selected from tauopathies, AA amyloidosis, AL amyloidosis, AApoAI amyloidosis, AApoAll amyloidosis, ATTR amyloidosis, schizophrenia and other DISC1opathies, amyotrophic lateral sclerosis, frontotemporal lobar degeneration and other FUS proteinopathies, diabetes mellitus type 2, Parkinson's disease and other synucleinopathies, chronic traumatic encephalopathy and other TDP-43 proteinopathies, Huntington's disease, familial visceral amyloidosis and/or Alzheimer's dementia, obtained data are compared with standard values, a significantly different quantity of disease indicators is detected as discrepancy in the comparison and the discrepancy is attributed to an above-mentioned disease.

7. The method of claim 1, wherein the aggregates comprise small, freely diffusing oligomers.

8. The method of claim 1, wherein a quantitative determination of disease indicators is carried out, which determination comprises a determination of composition, size and/or shape of aggregates.

9. The method of claim 7, wherein a quantitative determination of disease indicators is carried out, which determination comprises a determination of composition, size and/or shape of aggregates.

10. The method of claim 1, wherein the aggregates comprise one or more peptides or monomers of SEQ ID Nos: 1-9 and 12-14.

\* \* \* \* \*

SEQUENCE LISTING

<160> NUMBER OF SEQ ID NOS: 15

<210> SEQ ID NO 1
<211> LENGTH: 122
<212> TYPE: PRT
<213> ORGANISM: Homo sapiens

<400> SEQUENCE: 1

Met Lys Leu Leu Thr Gly Leu Val Phe Cys Ser Leu Val Leu Gly Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Val Trp Ala Ala Glu Ala Ile Ser Asp Ala Arg
65                  70                  75                  80

Glu Asn Ile Gln Arg Phe Phe Gly His Gly Ala Glu Asp Ser Leu Ala
            85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
        115                 120

<210> SEQ ID NO 2
<211> LENGTH: 213
<212> TYPE: PRT
<213> ORGANISM: Homo sapiens

<400> SEQUENCE: 2

Met Arg Pro Gly Thr Gly Gln Gly Gly Leu Glu Ala Pro Gly Glu Pro
1               5                   10                  15

Gly Pro Asn Leu Arg Gln Arg Trp Pro Leu Leu Leu Leu Gly Leu Ala
            20                  25                  30

Val Val Thr His Gly Leu Leu Arg Pro Thr Ala Ala Ser Gln Ser Arg

```
                35                  40                  45
Ala Leu Gly Pro Gly Ala Pro Gly Gly Ser Ser Arg Ser Ser Leu Arg
 50                  55                  60

Ser Arg Trp Gly Arg Phe Leu Leu Gln Arg Gly Ser Trp Thr Gly Pro
 65                  70                  75                  80

Arg Cys Trp Pro Arg Gly Phe Gln Ser Lys His Asn Ser Val Thr His
                 85                  90                  95

Val Phe Gly Ser Gly Thr Gln Leu Thr Val Leu Ser Gln Pro Lys Ala
            100                 105                 110

Thr Pro Ser Val Thr Leu Phe Pro Pro Ser Glu Glu Leu Gln Ala
        115                 120                 125

Asn Lys Ala Thr Leu Val Cys Leu Met Asn Asp Phe Tyr Pro Gly Ile
130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser
                165                 170                 175

Ser Tyr Leu Ser Leu Thr Pro Glu Gln Trp Arg Ser Arg Arg Ser Tyr
            180                 185                 190

Ser Cys Gln Val Met His Glu Gly Ser Thr Val Glu Lys Thr Val Ala
        195                 200                 205

Pro Ala Glu Cys Ser
        210

<210> SEQ ID NO 3
<211> LENGTH: 267
<212> TYPE: PRT
<213> ORGANISM: Homo sapiens

<400> SEQUENCE: 3

Met Lys Ala Ala Val Leu Thr Leu Ala Val Leu Phe Leu Thr Gly Ser
 1               5                  10                  15

Gln Ala Arg His Phe Trp Gln Asp Glu Pro Pro Gln Ser Pro Trp
             20                  25                  30

Asp Arg Val Lys Asp Leu Ala Thr Val Tyr Val Asp Val Leu Lys Asp
             35                  40                  45

Ser Gly Arg Asp Tyr Val Ser Gln Phe Glu Gly Ser Ala Leu Gly Lys
 50                  55                  60

Gln Leu Asn Leu Lys Leu Leu Asp Asn Trp Asp Ser Val Thr Ser Thr
 65                  70                  75                  80

Phe Ser Lys Leu Arg Glu Gln Leu Gly Pro Val Thr Gln Glu Phe Trp
                 85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190
```

```
Glu Leu Arg Gln Arg Leu Ala Ala Arg Leu Gly Ala Leu Lys Glu Asn
            195                 200                 205

Gly Gly Ala Arg Leu Ala Glu Tyr His Ala Lys Ala Thr Glu His Leu
        210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265
```

<210> SEQ ID NO 4
<211> LENGTH: 100
<212> TYPE: PRT
<213> ORGANISM: Homo sapiens

<400> SEQUENCE: 4

```
Met Lys Leu Leu Ala Ala Thr Val Leu Leu Leu Thr Ile Cys Ser Leu
1               5                   10                  15

Glu Gly Ala Leu Val Arg Arg Gln Ala Lys Glu Pro Cys Val Glu Ser
            20                  25                  30

Leu Val Ser Gln Tyr Phe Gln Thr Val Thr Asp Tyr Gly Lys Asp Leu
        35                  40                  45

Met Glu Lys Val Lys Ser Pro Glu Leu Gln Ala Glu Ala Lys Ser Tyr
    50                  55                  60

Phe Glu Lys Ser Lys Glu Gln Leu Thr Pro Leu Ile Lys Lys Ala Gly
65                  70                  75                  80

Thr Glu Leu Val Asn Phe Leu Ser Tyr Phe Val Glu Leu Gly Thr Gln
                85                  90                  95

Pro Ala Thr Gln
            100
```

<210> SEQ ID NO 5
<211> LENGTH: 147
<212> TYPE: PRT
<213> ORGANISM: Homo sapiens

<400> SEQUENCE: 5

```
Met Ala Ser His Arg Leu Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
    130                 135                 140
```

Pro Lys Glu
145

<210> SEQ ID NO 6
<211> LENGTH: 854
<212> TYPE: PRT
<213> ORGANISM: Homo sapiens

<400> SEQUENCE: 6

```
Met Pro Gly Gly Pro Gln Gly Ala Pro Ala Ala Gly Gly
1               5                   10                  15

Gly Val Ser His Arg Ala Gly Ser Arg Asp Cys Leu Pro Ala Ala
            20                  25                  30

Cys Phe Arg Arg Arg Leu Ala Arg Arg Pro Gly Tyr Met Arg Ser
            35                  40                  45

Ser Thr Gly Pro Gly Ile Gly Phe Leu Ser Pro Ala Val Gly Thr Leu
        50                  55                  60

Phe Arg Phe Pro Gly Gly Val Ser Gly Glu Glu Ser His His Ser Glu
65                  70                  75                  80

Ser Arg Ala Arg Gln Cys Gly Leu Asp Ser Arg Gly Leu Leu Val Arg
                85                  90                  95

Ser Pro Val Ser Lys Ser Ala Ala Pro Thr Val Thr Ser Val Arg
            100                 105                 110

Gly Thr Ser Ala His Phe Gly Ile Gln Leu Arg Gly Thr Arg Leu
            115                 120                 125

Pro Asp Arg Leu Ser Trp Pro Cys Gly Pro Gly Ser Ala Gly Trp Gln
130                 135                 140

Gln Glu Phe Ala Ala Met Asp Ser Ser Glu Thr Leu Asp Ala Ser Trp
145                 150                 155                 160

Glu Ala Ala Cys Ser Asp Gly Ala Arg Arg Val Arg Ala Ala Gly Ser
                165                 170                 175

Leu Pro Ser Ala Glu Leu Ser Ser Asn Ser Cys Ser Pro Gly Cys Gly
            180                 185                 190

Pro Glu Val Pro Pro Thr Pro Gly Ser His Ser Ala Phe Thr Ser
            195                 200                 205

Ser Phe Ser Phe Ile Arg Leu Ser Leu Gly Ser Ala Gly Glu Arg Gly
        210                 215                 220

Glu Ala Glu Gly Cys Pro Pro Ser Arg Glu Ala Glu Ser His Cys Gln
225                 230                 235                 240

Ser Pro Gln Glu Met Gly Ala Lys Ala Ala Ser Leu Asp Gly Pro His
                245                 250                 255

Glu Asp Pro Arg Cys Leu Ser Arg Pro Phe Ser Leu Leu Ala Thr Arg
            260                 265                 270

Val Ser Ala Asp Leu Ala Gln Ala Ala Arg Asn Ser Ser Arg Pro Glu
        275                 280                 285

Arg Asp Met His Ser Leu Pro Asp Met Asp Pro Gly Ser Ser Ser Ser
290                 295                 300

Leu Asp Pro Ser Leu Ala Gly Cys Gly Gly Asp Gly Ser Ser Gly Ser
305                 310                 315                 320

Gly Asp Ala His Ser Trp Asp Thr Leu Leu Arg Lys Trp Glu Pro Val
                325                 330                 335

Leu Arg Asp Cys Leu Leu Arg Asn Arg Gln Met Glu Val Ile Ser
            340                 345                 350

Leu Arg Leu Lys Leu Gln Lys Leu Gln Glu Asp Ala Val Glu Asn Asp
        355                 360                 365
```

```
Asp Tyr Asp Lys Ala Glu Thr Leu Gln Gln Arg Leu Glu Asp Leu Glu
        370                 375                 380

Gln Glu Lys Ile Ser Leu His Phe Gln Leu Pro Ser Arg Gln Pro Ala
385                 390                 395                 400

Leu Ser Ser Phe Leu Gly His Leu Ala Ala Gln Val Gln Ala Ala Leu
                405                 410                 415

Arg Arg Gly Ala Thr Gln Gln Ala Ser Gly Asp Asp Thr His Thr Pro
            420                 425                 430

Leu Arg Met Glu Pro Arg Leu Leu Glu Pro Thr Ala Gln Asp Ser Leu
        435                 440                 445

His Val Ser Ile Thr Arg Arg Asp Trp Leu Leu Gln Glu Lys Gln Gln
    450                 455                 460

Leu Gln Lys Glu Ile Glu Ala Leu Gln Ala Arg Met Phe Val Leu Glu
465                 470                 475                 480

Ala Lys Asp Gln Gln Leu Arg Arg Glu Ile Glu Glu Gln Glu Gln Gln
                485                 490                 495

Leu Gln Trp Gln Gly Cys Asp Leu Thr Pro Leu Val Gly Gln Leu Ser
            500                 505                 510

Leu Gly Gln Leu Gln Glu Val Ser Lys Ala Leu Gln Asp Thr Leu Ala
        515                 520                 525

Ser Ala Gly Gln Ile Pro Phe His Ala Glu Pro Pro Glu Thr Ile Arg
    530                 535                 540

Ser Leu Gln Glu Arg Ile Lys Ser Leu Asn Leu Ser Leu Lys Glu Ile
545                 550                 555                 560

Thr Thr Lys Val Cys Met Ser Glu Lys Phe Cys Ser Thr Leu Arg Lys
                565                 570                 575

Lys Val Asn Asp Ile Glu Thr Gln Leu Pro Ala Leu Leu Glu Ala Lys
            580                 585                 590

Met His Ala Ile Ser Gly Asn His Phe Trp Thr Ala Lys Asp Leu Thr
        595                 600                 605

Glu Glu Ile Arg Ser Leu Thr Ser Glu Arg Glu Gly Leu Glu Gly Leu
    610                 615                 620

Leu Ser Lys Leu Leu Val Leu Ser Ser Arg Asn Val Lys Lys Leu Gly
625                 630                 635                 640

Ser Val Lys Glu Asp Tyr Asn Arg Leu Arg Arg Glu Val Glu His Gln
                645                 650                 655

Glu Thr Ala Tyr Glu Thr Ser Val Lys Glu Asn Thr Met Lys Tyr Met
            660                 665                 670

Glu Thr Leu Lys Asn Lys Leu Cys Ser Cys Lys Cys Pro Leu Leu Gly
        675                 680                 685

Lys Val Trp Glu Ala Asp Leu Glu Ala Cys Arg Leu Leu Ile Gln Ser
    690                 695                 700

Leu Gln Leu Gln Glu Ala Arg Gly Ser Leu Ser Val Glu Asp Glu Arg
705                 710                 715                 720

Gln Met Asp Asp Leu Glu Gly Ala Ala Pro Ile Pro Pro Arg Leu
                725                 730                 735

His Ser Glu Asp Lys Arg Lys Thr Pro Leu Lys Val Leu Glu Glu Trp
            740                 745                 750

Lys Thr His Leu Ile Pro Ser Leu His Cys Ala Gly Gly Glu Gln Lys
        755                 760                 765

Glu Glu Ser Tyr Ile Leu Ser Ala Glu Leu Gly Glu Lys Cys Glu Asp
    770                 775                 780
```

```
Ile Gly Lys Lys Leu Leu Tyr Leu Glu Asp Gln Leu His Thr Ala Ile
785                 790                 795                 800

His Ser His Asp Glu Asp Leu Ile Gln Ser Leu Arg Arg Glu Leu Gln
                805                 810                 815

Met Val Lys Glu Thr Leu Gln Ala Met Ile Leu Gln Leu Gln Pro Ala
            820                 825                 830

Lys Glu Ala Gly Glu Arg Glu Ala Ala Ser Cys Met Thr Ala Gly
        835                 840                 845

Val His Glu Ala Gln Ala
    850

<210> SEQ ID NO 7
<211> LENGTH: 526
<212> TYPE: PRT
<213> ORGANISM: Homo sapiens

<400> SEQUENCE: 7

Met Ala Ser Asn Asp Tyr Thr Gln Gln Ala Thr Gln Ser Tyr Gly Ala
1               5                   10                  15

Tyr Pro Thr Gln Pro Gly Gln Gly Tyr Ser Gln Gln Ser Ser Gln Pro
            20                  25                  30

Tyr Gly Gln Gln Ser Tyr Ser Gly Tyr Ser Gln Ser Thr Asp Thr Ser
        35                  40                  45

Gly Tyr Gly Gln Ser Ser Tyr Ser Ser Tyr Gly Gln Ser Gln Asn Thr
    50                  55                  60

Gly Tyr Gly Thr Gln Ser Thr Pro Gln Gly Tyr Gly Ser Thr Gly Gly
65                  70                  75                  80

Tyr Gly Ser Ser Gln Ser Ser Gln Ser Ser Tyr Gly Gln Gln Ser Ser
                85                  90                  95

Tyr Pro Gly Tyr Gly Gln Gln Pro Ala Pro Ser Ser Thr Ser Gly Ser
            100                 105                 110

Tyr Gly Ser Ser Ser Gln Ser Ser Tyr Gly Gln Pro Gln Ser Gly
        115                 120                 125

Ser Tyr Ser Gln Gln Pro Ser Tyr Gly Gly Gln Gln Ser Tyr Gly
    130                 135                 140

Gln Gln Gln Ser Tyr Asn Pro Pro Gln Gly Tyr Gly Gln Gln Asn Gln
145                 150                 155                 160

Tyr Asn Ser Ser Ser Gly Gly Gly Gly Gly Gly Gly Gly Gly Gly Asn
                165                 170                 175

Tyr Gly Gln Asp Gln Ser Ser Met Ser Ser Gly Gly Gly Ser Gly Gly
            180                 185                 190

Gly Tyr Gly Asn Gln Asp Gln Ser Gly Gly Gly Gly Ser Gly Gly Tyr
        195                 200                 205

Gly Gln Gln Asp Arg Gly Gly Arg Gly Arg Gly Gly Ser Gly Gly Gly
    210                 215                 220

Gly Gly Gly Gly Gly Gly Tyr Asn Arg Ser Ser Gly Gly Tyr Glu
225                 230                 235                 240

Pro Arg Gly Arg Gly Gly Gly Arg Gly Gly Arg Gly Gly Met Gly Gly
            245                 250                 255

Ser Asp Arg Gly Gly Phe Asn Lys Phe Gly Gly Pro Arg Asp Gln Gly
        260                 265                 270

Ser Arg His Asp Ser Glu Gln Asp Asn Ser Asp Asn Asn Thr Ile Phe
    275                 280                 285

Val Gln Gly Leu Gly Glu Asn Val Thr Ile Glu Ser Val Ala Asp Tyr
290                 295                 300
```

```
Phe Lys Gln Ile Gly Ile Ile Lys Thr Asn Lys Lys Thr Gly Gln Pro
305                 310                 315                 320

Met Ile Asn Leu Tyr Thr Asp Arg Glu Thr Gly Lys Leu Lys Gly Glu
                325                 330                 335

Ala Thr Val Ser Phe Asp Asp Pro Pro Ser Ala Lys Ala Ala Ile Asp
            340                 345                 350

Trp Phe Asp Gly Lys Glu Phe Ser Gly Asn Pro Ile Lys Val Ser Phe
        355                 360                 365

Ala Thr Arg Arg Ala Asp Phe Asn Arg Gly Gly Asn Gly Arg Gly
370                 375                 380

Gly Arg Gly Arg Gly Gly Pro Met Gly Arg Gly Gly Tyr Gly Gly Gly
385                 390                 395                 400

Gly Ser Gly Gly Gly Arg Gly Gly Phe Pro Ser Gly Gly Gly
            405                 410                 415

Gly Gly Gly Gln Gln Arg Ala Gly Asp Trp Lys Cys Pro Asn Pro Thr
                420                 425                 430

Cys Glu Asn Met Asn Phe Ser Trp Arg Asn Glu Cys Asn Gln Cys Lys
                435                 440                 445

Ala Pro Lys Pro Asp Gly Pro Gly Gly Pro Gly Gly Ser His Met
450                 455                 460

Gly Gly Asn Tyr Gly Asp Asp Arg Arg Gly Gly Arg Gly Gly Tyr Asp
465                 470                 475                 480

Arg Gly Gly Tyr Arg Gly Arg Gly Gly Asp Arg Gly Gly Phe Arg Gly
                485                 490                 495

Gly Arg Gly Gly Gly Asp Arg Gly Gly Phe Gly Pro Gly Lys Met Asp
                500                 505                 510

Ser Arg Gly Glu His Arg Gln Asp Arg Arg Glu Arg Pro Tyr
            515                 520                 525

<210> SEQ ID NO 8
<211> LENGTH: 89
<212> TYPE: PRT
<213> ORGANISM: Homo sapiens

<400> SEQUENCE: 8

Met Gly Ile Leu Lys Leu Gln Val Phe Leu Ile Val Leu Ser Val Ala
1               5                   10                  15

Leu Asn His Leu Lys Ala Thr Pro Ile Glu Ser His Gln Val Glu Lys
                20                  25                  30

Arg Lys Cys Asn Thr Ala Thr Cys Ala Thr Gln Arg Leu Ala Asn Phe
            35                  40                  45

Leu Val His Ser Ser Asn Asn Phe Gly Ala Ile Leu Ser Ser Thr Asn
        50                  55                  60

Val Gly Ser Asn Thr Tyr Gly Lys Arg Asn Ala Val Glu Val Leu Lys
65                  70                  75                  80

Arg Glu Pro Leu Asn Tyr Leu Pro Leu
                85

<210> SEQ ID NO 9
<211> LENGTH: 154
<212> TYPE: PRT
<213> ORGANISM: Homo sapiens

<400> SEQUENCE: 9

Met Ala Thr Lys Ala Val Cys Val Leu Lys Gly Asp Gly Pro Val Gln
1               5                   10                  15
```

```
Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
 50                  55                  60

Phe Asn Pro Leu Ser Arg Lys His Gly Pro Lys Asp Glu Glu Arg
 65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
130                 135                 140

Leu Ala Cys Gly Val Ile Gly Ile Ala Gln
145                 150

<210> SEQ ID NO 10
<211> LENGTH: 140
<212> TYPE: PRT
<213> ORGANISM: Homo sapiens

<400> SEQUENCE: 10

Met Asp Val Phe Met Lys Gly Leu Ser Lys Ala Lys Glu Gly Val Val
 1               5                  10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
 50                  55                  60

Asn Val Gly Gly Ala Val Val Thr Gly Val Thr Ala Val Ala Gln Lys
 65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
130                 135                 140

<210> SEQ ID NO 11
<211> LENGTH: 758
<212> TYPE: PRT
<213> ORGANISM: Homo sapiens

<400> SEQUENCE: 11

Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45
```

```
Gln Thr Pro Thr Glu Asp Gly Ser Glu Glu Pro Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
                180                 185                 190

Leu Gly Asp Leu His Gln Glu Gly Pro Pro Leu Lys Gly Ala Gly Gly
            195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
                260                 265                 270

Ser Lys Val Ser Thr Glu Ile Pro Ala Ser Glu Pro Asp Gly Pro Ser
            275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
                340                 345                 350

Glu Pro Ser Glu Lys Gln Pro Ala Ala Ala Pro Arg Gly Lys Pro Val
            355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
                405                 410                 415

Pro Gly Ser Ser Asp Pro Leu Ile Gln Pro Ser Ser Pro Ala Val Cys
                420                 425                 430

Pro Glu Pro Pro Ser Ser Pro Lys Tyr Val Ser Ser Val Thr Ser Arg
            435                 440                 445

Thr Gly Ser Ser Gly Ala Lys Glu Met Lys Leu Lys Gly Ala Asp Gly
    450                 455                 460
```

```
Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
            485                 490                 495

Lys Thr Pro Pro Ser Ser Gly Glu Pro Pro Lys Ser Gly Asp Arg Ser
        500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
        530                 535                 540

Val Val Arg Thr Pro Pro Lys Ser Pro Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
            660                 665                 670

Ser Leu Asp Asn Ile Thr His Val Pro Gly Gly Gly Asn Lys Lys Ile
        675                 680                 685

Glu Thr His Lys Leu Thr Phe Arg Glu Asn Ala Lys Ala Lys Thr Asp
690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
                725                 730                 735

Val Asp Ser Pro Gln Leu Ala Thr Leu Ala Asp Glu Val Ser Ala Ser
            740                 745                 750

Leu Ala Lys Gln Gly Leu
        755

<210> SEQ ID NO 12
<211> LENGTH: 414
<212> TYPE: PRT
<213> ORGANISM: Homo sapiens

<400> SEQUENCE: 12

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
65                  70                  75                  80
```

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
            260                 265                 270

Ser Gly Arg Phe Gly Gly Asn Pro Gly Gly Phe Gly Asn Gln Gly Gly
        275                 280                 285

Phe Gly Asn Ser Arg Gly Gly Ala Gly Leu Gly Asn Asn Gln Gly
    290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
            340                 345                 350

Asn Gln Asn Gln Gly Asn Met Gln Arg Glu Pro Asn Gln Ala Phe Gly
        355                 360                 365

Ser Gly Asn Asn Ser Tyr Ser Gly Ser Asn Ser Gly Ala Ala Ile Gly
    370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410

<210> SEQ ID NO 13
<211> LENGTH: 3142
<212> TYPE: PRT
<213> ORGANISM: Homo sapiens

<400> SEQUENCE: 13

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
            20                  25                  30

Gln Gln Gln Gln Gln Gln Pro Pro Pro Pro Pro Pro Pro Pro

```
                35                  40                  45
Pro Gln Leu Pro Gln Pro Pro Gln Ala Gln Pro Leu Pro Gln
    50                  55                  60
Pro Gln Pro Pro Pro Pro Pro Pro Pro Gly Pro Ala Val
65                  70                  75                  80
Ala Glu Glu Pro Leu His Arg Pro Lys Lys Glu Leu Ser Ala Thr Lys
                    85                  90                  95
Lys Asp Arg Val Asn His Cys Leu Thr Ile Cys Glu Asn Ile Val Ala
                100                 105                 110
Gln Ser Val Arg Asn Ser Pro Glu Phe Gln Lys Leu Leu Gly Ile Ala
                115                 120                 125
Met Glu Leu Phe Leu Leu Cys Ser Asp Asp Ala Glu Ser Asp Val Arg
    130                 135                 140
Met Val Ala Asp Glu Cys Leu Asn Lys Val Ile Lys Ala Leu Met Asp
145                 150                 155                 160
Ser Asn Leu Pro Arg Leu Gln Leu Glu Leu Tyr Lys Glu Ile Lys Lys
                    165                 170                 175
Asn Gly Ala Pro Arg Ser Leu Arg Ala Ala Leu Trp Arg Phe Ala Glu
                180                 185                 190
Leu Ala His Leu Val Arg Pro Gln Lys Cys Arg Pro Tyr Leu Val Asn
                195                 200                 205
Leu Leu Pro Cys Leu Thr Arg Thr Ser Lys Arg Pro Glu Glu Ser Val
    210                 215                 220
Gln Glu Thr Leu Ala Ala Ala Val Pro Lys Ile Met Ala Ser Phe Gly
225                 230                 235                 240
Asn Phe Ala Asn Asp Asn Glu Ile Lys Val Leu Leu Lys Ala Phe Ile
                    245                 250                 255
Ala Asn Leu Lys Ser Ser Pro Thr Ile Arg Arg Thr Ala Ala Gly
                260                 265                 270
Ser Ala Val Ser Ile Cys Gln His Ser Arg Arg Thr Gln Tyr Phe Tyr
                275                 280                 285
Ser Trp Leu Leu Asn Val Leu Leu Gly Leu Leu Val Pro Val Glu Asp
    290                 295                 300
Glu His Ser Thr Leu Leu Ile Leu Gly Val Leu Leu Thr Leu Arg Tyr
305                 310                 315                 320
Leu Val Pro Leu Leu Gln Gln Gln Val Lys Asp Thr Ser Leu Lys Gly
                    325                 330                 335
Ser Phe Gly Val Thr Arg Lys Glu Met Glu Val Ser Pro Ser Ala Glu
                340                 345                 350
Gln Leu Val Gln Val Tyr Glu Leu Thr Leu His His Thr Gln His Gln
                355                 360                 365
Asp His Asn Val Val Thr Gly Ala Leu Glu Leu Leu Gln Gln Leu Phe
    370                 375                 380
Arg Thr Pro Pro Glu Leu Leu Gln Thr Leu Thr Ala Val Gly Gly
385                 390                 395                 400
Ile Gly Gln Leu Thr Ala Ala Lys Glu Glu Ser Gly Gly Arg Ser Arg
                    405                 410                 415
Ser Gly Ser Ile Val Glu Leu Ile Ala Gly Gly Gly Ser Ser Cys Ser
                420                 425                 430
Pro Val Leu Ser Arg Lys Gln Lys Gly Lys Val Leu Leu Gly Glu Glu
                435                 440                 445
Glu Ala Leu Glu Asp Asp Ser Glu Ser Arg Ser Asp Val Ser Ser Ser
                450                 455                 460
```

```
Ala Leu Thr Ala Ser Val Lys Asp Glu Ile Ser Gly Glu Leu Ala Ala
465                 470                 475                 480

Ser Ser Gly Val Ser Thr Pro Gly Ser Ala Gly His Asp Ile Ile Thr
                485                 490                 495

Glu Gln Pro Arg Ser Gln His Thr Leu Gln Ala Asp Ser Val Asp Leu
            500                 505                 510

Ala Ser Cys Asp Leu Thr Ser Ser Ala Thr Asp Gly Asp Glu Glu Asp
            515                 520                 525

Ile Leu Ser His Ser Ser Ser Gln Val Ser Ala Val Pro Ser Asp Pro
        530                 535                 540

Ala Met Asp Leu Asn Asp Gly Thr Gln Ala Ser Ser Pro Ile Ser Asp
545                 550                 555                 560

Ser Ser Gln Thr Thr Thr Glu Gly Pro Asp Ser Ala Val Thr Pro Ser
                565                 570                 575

Asp Ser Ser Glu Ile Val Leu Asp Gly Thr Asp Asn Gln Tyr Leu Gly
            580                 585                 590

Leu Gln Ile Gly Gln Pro Gln Asp Glu Asp Glu Ala Thr Gly Ile
        595                 600                 605

Leu Pro Asp Glu Ala Ser Glu Ala Phe Arg Asn Ser Ser Met Ala Leu
610                 615                 620

Gln Gln Ala His Leu Leu Lys Asn Met Ser His Cys Arg Gln Pro Ser
625                 630                 635                 640

Asp Ser Ser Val Asp Lys Phe Val Leu Arg Asp Glu Ala Thr Glu Pro
            645                 650                 655

Gly Asp Gln Glu Asn Lys Pro Cys Arg Ile Lys Gly Asp Ile Gly Gln
            660                 665                 670

Ser Thr Asp Asp Asp Ser Ala Pro Leu Val His Cys Val Arg Leu Leu
        675                 680                 685

Ser Ala Ser Phe Leu Leu Thr Gly Gly Lys Asn Val Leu Val Pro Asp
        690                 695                 700

Arg Asp Val Arg Val Ser Val Lys Ala Leu Ala Leu Ser Cys Val Gly
705                 710                 715                 720

Ala Ala Val Ala Leu His Pro Glu Ser Phe Ser Lys Leu Tyr Lys
                725                 730                 735

Val Pro Leu Asp Thr Thr Glu Tyr Pro Glu Glu Gln Tyr Val Ser Asp
            740                 745                 750

Ile Leu Asn Tyr Ile Asp His Gly Asp Pro Gln Val Arg Gly Ala Thr
        755                 760                 765

Ala Ile Leu Cys Gly Thr Leu Ile Cys Ser Ile Leu Ser Arg Ser Arg
        770                 775                 780

Phe His Val Gly Asp Trp Met Gly Thr Ile Arg Thr Leu Thr Gly Asn
785                 790                 795                 800

Thr Phe Ser Leu Ala Asp Cys Ile Pro Leu Leu Arg Lys Thr Leu Lys
                805                 810                 815

Asp Glu Ser Ser Val Thr Cys Lys Leu Ala Cys Thr Ala Val Arg Asn
            820                 825                 830

Cys Val Met Ser Leu Cys Ser Ser Ser Tyr Ser Glu Leu Gly Leu Gln
            835                 840                 845

Leu Ile Ile Asp Val Leu Thr Leu Arg Asn Ser Ser Tyr Trp Leu Val
        850                 855                 860

Arg Thr Glu Leu Leu Glu Thr Leu Ala Glu Ile Asp Phe Arg Leu Val
865                 870                 875                 880
```

```
Ser Phe Leu Glu Ala Lys Ala Glu Asn Leu His Arg Gly Ala His His
                885                 890                 895

Tyr Thr Gly Leu Leu Lys Leu Gln Glu Arg Val Leu Asn Asn Val Val
            900                 905                 910

Ile His Leu Leu Gly Asp Glu Asp Pro Arg Val Arg His Val Ala Ala
            915                 920                 925

Ala Ser Leu Ile Arg Leu Val Pro Lys Leu Phe Tyr Lys Cys Asp Gln
            930                 935                 940

Gly Gln Ala Asp Pro Val Ala Val Ala Arg Asp Gln Ser Ser Val
945                 950                 955                 960

Tyr Leu Lys Leu Leu Met His Glu Thr Gln Pro Pro Ser His Phe Ser
                965                 970                 975

Val Ser Thr Ile Thr Arg Ile Tyr Arg Gly Tyr Asn Leu Leu Pro Ser
                980                 985                 990

Ile Thr Asp Val Thr Met Glu Asn Asn Leu Ser Arg Val Ile Ala Ala
            995                 1000                1005

Val Ser His Glu Leu Ile Thr Ser Thr Thr Arg Ala Leu Thr Phe
1010                1015                1020

Gly Cys Cys Glu Ala Leu Cys Leu Leu Ser Thr Ala Phe Pro Val
1025                1030                1035

Cys Ile Trp Ser Leu Gly Trp His Cys Gly Val Pro Pro Leu Ser
1040                1045                1050

Ala Ser Asp Glu Ser Arg Lys Ser Cys Thr Val Gly Met Ala Thr
1055                1060                1065

Met Ile Leu Thr Leu Leu Ser Ser Ala Trp Phe Pro Leu Asp Leu
1070                1075                1080

Ser Ala His Gln Asp Ala Leu Ile Leu Ala Gly Asn Leu Leu Ala
1085                1090                1095

Ala Ser Ala Pro Lys Ser Leu Arg Ser Ser Trp Ala Ser Glu Glu
1100                1105                1110

Glu Ala Asn Pro Ala Ala Thr Lys Gln Glu Glu Val Trp Pro Ala
1115                1120                1125

Leu Gly Asp Arg Ala Leu Val Pro Met Val Glu Gln Leu Phe Ser
1130                1135                1140

His Leu Leu Lys Val Ile Asn Ile Cys Ala His Val Leu Asp Asp
1145                1150                1155

Val Ala Pro Gly Pro Ala Ile Lys Ala Ala Leu Pro Ser Leu Thr
1160                1165                1170

Asn Pro Pro Ser Leu Ser Pro Ile Arg Arg Lys Gly Lys Glu Lys
1175                1180                1185

Glu Pro Gly Glu Gln Ala Ser Val Pro Leu Ser Pro Lys Lys Gly
1190                1195                1200

Ser Glu Ala Ser Ala Ala Ser Arg Gln Ser Asp Thr Ser Gly Pro
1205                1210                1215

Val Thr Thr Ser Lys Ser Ser Ser Leu Gly Ser Phe Tyr His Leu
1220                1225                1230

Pro Ser Tyr Leu Lys Leu His Asp Val Leu Lys Ala Thr His Ala
1235                1240                1245

Asn Tyr Lys Val Thr Leu Asp Leu Gln Asn Ser Thr Glu Lys Phe
1250                1255                1260

Gly Gly Phe Leu Arg Ser Ala Leu Asp Val Leu Ser Gln Ile Leu
1265                1270                1275

Glu Leu Ala Thr Leu Gln Asp Ile Gly Lys Cys Val Glu Glu Ile
```

```
            1280                1285               1290

Leu Gly Tyr Leu Lys Ser Cys Phe Ser Arg Glu Pro Met Met Ala
            1295                1300               1305

Thr Val Cys Val Gln Gln Leu Leu Lys Thr Leu Phe Gly Thr Asn
            1310                1315               1320

Leu Ala Ser Gln Phe Asp Gly Leu Ser Ser Asn Pro Ser Lys Ser
            1325                1330               1335

Gln Gly Arg Ala Gln Arg Leu Gly Ser Ser Val Arg Pro Gly
            1340                1345               1350

Leu Tyr His Tyr Cys Phe Met Ala Pro Tyr Thr His Phe Thr Gln
            1355                1360               1365

Ala Leu Ala Asp Ala Ser Leu Arg Asn Met Val Gln Ala Glu Gln
            1370                1375               1380

Glu Asn Asp Thr Ser Gly Trp Phe Asp Val Leu Gln Lys Val Ser
            1385                1390               1395

Thr Gln Leu Lys Thr Asn Leu Thr Ser Val Thr Lys Asn Arg Ala
            1400                1405               1410

Asp Lys Asn Ala Ile His Asn His Ile Arg Leu Phe Glu Pro Leu
            1415                1420               1425

Val Ile Lys Ala Leu Lys Gln Tyr Thr Thr Thr Thr Cys Val Gln
            1430                1435               1440

Leu Gln Lys Gln Val Leu Asp Leu Leu Ala Gln Leu Val Gln Leu
            1445                1450               1455

Arg Val Asn Tyr Cys Leu Leu Asp Ser Asp Gln Val Phe Ile Gly
            1460                1465               1470

Phe Val Leu Lys Gln Phe Glu Tyr Ile Glu Val Gly Gln Phe Arg
            1475                1480               1485

Glu Ser Glu Ala Ile Ile Pro Asn Ile Phe Phe Phe Leu Val Leu
            1490                1495               1500

Leu Ser Tyr Glu Arg Tyr His Ser Lys Gln Ile Ile Gly Ile Pro
            1505                1510               1515

Lys Ile Ile Gln Leu Cys Asp Gly Ile Met Ala Ser Gly Arg Lys
            1520                1525               1530

Ala Val Thr His Ala Ile Pro Ala Leu Gln Pro Ile Val His Asp
            1535                1540               1545

Leu Phe Val Leu Arg Gly Thr Asn Lys Ala Asp Ala Gly Lys Glu
            1550                1555               1560

Leu Glu Thr Gln Lys Glu Val Val Val Ser Met Leu Leu Arg Leu
            1565                1570               1575

Ile Gln Tyr His Gln Val Leu Glu Met Phe Ile Leu Val Leu Gln
            1580                1585               1590

Gln Cys His Lys Glu Asn Glu Asp Lys Trp Lys Arg Leu Ser Arg
            1595                1600               1605

Gln Ile Ala Asp Ile Ile Leu Pro Met Leu Ala Lys Gln Gln Met
            1610                1615               1620

His Ile Asp Ser His Glu Ala Leu Gly Val Leu Asn Thr Leu Phe
            1625                1630               1635

Glu Ile Leu Ala Pro Ser Ser Leu Arg Pro Val Asp Met Leu Leu
            1640                1645               1650

Arg Ser Met Phe Val Thr Pro Asn Thr Met Ala Ser Val Ser Thr
            1655                1660               1665

Val Gln Leu Trp Ile Ser Gly Ile Leu Ala Ile Leu Arg Val Leu
            1670                1675               1680
```

```
Ile Ser Gln Ser Thr Glu Asp Ile Val Leu Ser Arg Ile Gln Glu
1685             1690                1695

Leu Ser Phe Ser Pro Tyr Leu Ile Ser Cys Thr Val Ile Asn Arg
1700             1705                1710

Leu Arg Asp Gly Asp Ser Thr Ser Thr Leu Glu Glu His Ser Glu
1715             1720                1725

Gly Lys Gln Ile Lys Asn Leu Pro Glu Glu Thr Phe Ser Arg Phe
1730             1735                1740

Leu Leu Gln Leu Val Gly Ile Leu Leu Glu Asp Ile Val Thr Lys
1745             1750                1755

Gln Leu Lys Val Glu Met Ser Glu Gln Gln His Thr Phe Tyr Cys
1760             1765                1770

Gln Glu Leu Gly Thr Leu Leu Met Cys Leu Ile His Ile Phe Lys
1775             1780                1785

Ser Gly Met Phe Arg Arg Ile Thr Ala Ala Ala Thr Arg Leu Phe
1790             1795                1800

Arg Ser Asp Gly Cys Gly Gly Ser Phe Tyr Thr Leu Asp Ser Leu
1805             1810                1815

Asn Leu Arg Ala Arg Ser Met Ile Thr Thr His Pro Ala Leu Val
1820             1825                1830

Leu Leu Trp Cys Gln Ile Leu Leu Leu Val Asn His Thr Asp Tyr
1835             1840                1845

Arg Trp Trp Ala Glu Val Gln Gln Thr Pro Lys Arg His Ser Leu
1850             1855                1860

Ser Ser Thr Lys Leu Leu Ser Pro Gln Met Ser Gly Glu Glu Glu
1865             1870                1875

Asp Ser Asp Leu Ala Ala Lys Leu Gly Met Cys Asn Arg Glu Ile
1880             1885                1890

Val Arg Arg Gly Ala Leu Ile Leu Phe Cys Asp Tyr Val Cys Gln
1895             1900                1905

Asn Leu His Asp Ser Glu His Leu Thr Trp Leu Ile Val Asn His
1910             1915                1920

Ile Gln Asp Leu Ile Ser Leu Ser His Glu Pro Pro Val Gln Asp
1925             1930                1935

Phe Ile Ser Ala Val His Arg Asn Ser Ala Ala Ser Gly Leu Phe
1940             1945                1950

Ile Gln Ala Ile Gln Ser Arg Cys Glu Asn Leu Ser Thr Pro Thr
1955             1960                1965

Met Leu Lys Lys Thr Leu Gln Cys Leu Glu Gly Ile His Leu Ser
1970             1975                1980

Gln Ser Gly Ala Val Leu Thr Leu Tyr Val Asp Arg Leu Leu Cys
1985             1990                1995

Thr Pro Phe Arg Val Leu Ala Arg Met Val Asp Ile Leu Ala Cys
2000             2005                2010

Arg Arg Val Glu Met Leu Leu Ala Ala Asn Leu Gln Ser Ser Met
2015             2020                2025

Ala Gln Leu Pro Met Glu Glu Leu Asn Arg Ile Gln Glu Tyr Leu
2030             2035                2040

Gln Ser Ser Gly Leu Ala Gln Arg His Gln Arg Leu Tyr Ser Leu
2045             2050                2055

Leu Asp Arg Phe Arg Leu Ser Thr Met Gln Asp Ser Leu Ser Pro
2060             2065                2070
```

-continued

```
Ser Pro Pro Val Ser Ser His Pro Leu Asp Gly Asp Gly His Val
2075                2080                2085
Ser Leu Glu Thr Val Ser Pro Asp Lys Asp Trp Tyr Val His Leu
2090                2095                2100
Val Lys Ser Gln Cys Trp Thr Arg Ser Asp Ser Ala Leu Leu Glu
2105                2110                2115
Gly Ala Glu Leu Val Asn Arg Ile Pro Ala Glu Asp Met Asn Ala
2120                2125                2130
Phe Met Met Asn Ser Glu Phe Asn Leu Ser Leu Leu Ala Pro Cys
2135                2140                2145
Leu Ser Leu Gly Met Ser Glu Ile Ser Gly Gly Gln Lys Ser Ala
2150                2155                2160
Leu Phe Glu Ala Ala Arg Glu Val Thr Leu Ala Arg Val Ser Gly
2165                2170                2175
Thr Val Gln Gln Leu Pro Ala Val His His Val Phe Gln Pro Glu
2180                2185                2190
Leu Pro Ala Glu Pro Ala Ala Tyr Trp Ser Lys Leu Asn Asp Leu
2195                2200                2205
Phe Gly Asp Ala Ala Leu Tyr Gln Ser Leu Pro Thr Leu Ala Arg
2210                2215                2220
Ala Leu Ala Gln Tyr Leu Val Val Val Ser Lys Leu Pro Ser His
2225                2230                2235
Leu His Leu Pro Pro Glu Lys Glu Lys Asp Ile Val Lys Phe Val
2240                2245                2250
Val Ala Thr Leu Glu Ala Leu Ser Trp His Leu Ile His Glu Gln
2255                2260                2265
Ile Pro Leu Ser Leu Asp Leu Gln Ala Gly Leu Asp Cys Cys Cys
2270                2275                2280
Leu Ala Leu Gln Leu Pro Gly Leu Trp Ser Val Val Ser Ser Thr
2285                2290                2295
Glu Phe Val Thr His Ala Cys Ser Leu Ile Tyr Cys Val His Phe
2300                2305                2310
Ile Leu Glu Ala Val Ala Val Gln Pro Gly Glu Gln Leu Leu Ser
2315                2320                2325
Pro Glu Arg Arg Thr Asn Thr Pro Lys Ala Ile Ser Glu Glu Glu
2330                2335                2340
Glu Glu Val Asp Pro Asn Thr Gln Asn Pro Lys Tyr Ile Thr Ala
2345                2350                2355
Ala Cys Glu Met Val Ala Glu Met Val Glu Ser Leu Gln Ser Val
2360                2365                2370
Leu Ala Leu Gly His Lys Arg Asn Ser Gly Val Pro Ala Phe Leu
2375                2380                2385
Thr Pro Leu Leu Arg Asn Ile Ile Ile Ser Leu Ala Arg Leu Pro
2390                2395                2400
Leu Val Asn Ser Tyr Thr Arg Val Pro Pro Leu Val Trp Lys Leu
2405                2410                2415
Gly Trp Ser Pro Lys Pro Gly Gly Asp Phe Gly Thr Ala Phe Pro
2420                2425                2430
Glu Ile Pro Val Glu Phe Leu Gln Glu Lys Glu Val Phe Lys Glu
2435                2440                2445
Phe Ile Tyr Arg Ile Asn Thr Leu Gly Trp Thr Ser Arg Thr Gln
2450                2455                2460
Phe Glu Glu Thr Trp Ala Thr Leu Leu Gly Val Leu Val Thr Gln
```

|   |   |   | 2465 |   |   |   |   | 2470 |   |   |   |   | 2475 |   |
|---|---|---|------|---|---|---|---|------|---|---|---|---|------|---|

Pro Leu Val Met Glu Gln Glu Glu Ser Pro Pro Glu Glu Asp Thr
               2480                2485               2490

Glu Arg Thr Gln Ile Asn Val Leu Ala Val Gln Ala Ile Thr Ser
         2495                2500                2505

Leu Val Leu Ser Ala Met Thr Val Pro Val Ala Gly Asn Pro Ala
      2510                2515                2520

Val Ser Cys Leu Glu Gln Gln Pro Arg Asn Lys Pro Leu Lys Ala
   2525                2530                2535

Leu Asp Thr Arg Phe Gly Arg Lys Leu Ser Ile Ile Arg Gly Ile
2540                2545                2550

Val Glu Gln Glu Ile Gln Ala Met Val Ser Lys Arg Glu Asn Ile
   2555                2560                2565

Ala Thr His His Leu Tyr Gln Ala Trp Asp Pro Val Pro Ser Leu
      2570                2575                2580

Ser Pro Ala Thr Thr Gly Ala Leu Ile Ser His Glu Lys Leu Leu
         2585                2590                2595

Leu Gln Ile Asn Pro Glu Arg Glu Leu Gly Ser Met Ser Tyr Lys
            2600                2605                2610

Leu Gly Gln Val Ser Ile His Ser Val Trp Leu Gly Asn Ser Ile
   2615                2620                2625

Thr Pro Leu Arg Glu Glu Trp Asp Glu Glu Glu Glu Glu
      2630                2635                2640

Ala Asp Ala Pro Ala Pro Ser Ser Pro Pro Thr Ser Pro Val Asn
   2645                2650                2655

Ser Arg Lys His Arg Ala Gly Val Asp Ile His Ser Cys Ser Gln
      2660                2665                2670

Phe Leu Leu Glu Leu Tyr Ser Arg Trp Ile Leu Pro Ser Ser Ser
   2675                2680                2685

Ala Arg Arg Thr Pro Ala Ile Leu Ile Ser Glu Val Val Arg Ser
   2690                2695                2700

Leu Leu Val Val Ser Asp Leu Phe Thr Glu Arg Asn Gln Phe Glu
   2705                2710                2715

Leu Met Tyr Val Thr Leu Thr Glu Leu Arg Arg Val His Pro Ser
   2720                2725                2730

Glu Asp Glu Ile Leu Ala Gln Tyr Leu Val Pro Ala Thr Cys Lys
   2735                2740                2745

Ala Ala Ala Val Leu Gly Met Asp Lys Ala Val Ala Glu Pro Val
   2750                2755                2760

Ser Arg Leu Leu Glu Ser Thr Leu Arg Ser Ser His Leu Pro Ser
   2765                2770                2775

Arg Val Gly Ala Leu His Gly Val Leu Tyr Val Leu Glu Cys Asp
   2780                2785                2790

Leu Leu Asp Asp Thr Ala Lys Gln Leu Ile Pro Val Ile Ser Asp
   2795                2800                2805

Tyr Leu Leu Ser Asn Leu Lys Gly Ile Ala His Cys Val Asn Ile
   2810                2815                2820

His Ser Gln Gln His Val Leu Val Met Cys Ala Thr Ala Phe Tyr
   2825                2830                2835

Leu Ile Glu Asn Tyr Pro Leu Asp Val Gly Pro Glu Phe Ser Ala
   2840                2845                2850

Ser Ile Ile Gln Met Cys Gly Val Met Leu Ser Gly Ser Glu Glu
   2855                2860                2865

```
Ser Thr Pro Ser Ile Ile Tyr His Cys Ala Leu Arg Gly Leu Glu
    2870            2875                2880

Arg Leu Leu Leu Ser Glu Gln Leu Ser Arg Leu Asp Ala Glu Ser
    2885            2890                2895

Leu Val Lys Leu Ser Val Asp Arg Val Asn Val His Ser Pro His
    2900            2905                2910

Arg Ala Met Ala Ala Leu Gly Leu Met Leu Thr Cys Met Tyr Thr
    2915            2920                2925

Gly Lys Glu Lys Val Ser Pro Gly Arg Thr Ser Asp Pro Asn Pro
    2930            2935                2940

Ala Ala Pro Asp Ser Glu Ser Val Ile Val Ala Met Glu Arg Val
    2945            2950                2955

Ser Val Leu Phe Asp Arg Ile Arg Lys Gly Phe Pro Cys Glu Ala
    2960            2965                2970

Arg Val Val Ala Arg Ile Leu Pro Gln Phe Leu Asp Asp Phe Phe
    2975            2980                2985

Pro Pro Gln Asp Ile Met Asn Lys Val Ile Gly Glu Phe Leu Ser
    2990            2995                3000

Asn Gln Gln Pro Tyr Pro Gln Phe Met Ala Thr Val Val Tyr Lys
    3005            3010                3015

Val Phe Gln Thr Leu His Ser Thr Gly Gln Ser Ser Met Val Arg
    3020            3025                3030

Asp Trp Val Met Leu Ser Leu Ser Asn Phe Thr Gln Arg Ala Pro
    3035            3040                3045

Val Ala Met Ala Thr Trp Ser Leu Ser Cys Phe Phe Val Ser Ala
    3050            3055                3060

Ser Thr Ser Pro Trp Val Ala Ala Ile Leu Pro His Val Ile Ser
    3065            3070                3075

Arg Met Gly Lys Leu Glu Gln Val Asp Val Asn Leu Phe Cys Leu
    3080            3085                3090

Val Ala Thr Asp Phe Tyr Arg His Gln Ile Glu Glu Glu Leu Asp
    3095            3100                3105

Arg Arg Ala Phe Gln Ser Val Leu Glu Val Val Ala Ala Pro Gly
    3110            3115                3120

Ser Pro Tyr His Arg Leu Leu Thr Cys Leu Arg Asn Val His Lys
    3125            3130                3135

Val Thr Thr Cys
    3140

<210> SEQ ID NO 14
<211> LENGTH: 148
<212> TYPE: PRT
<213> ORGANISM: Homo sapiens

<400> SEQUENCE: 14

Met Lys Ala Leu Ile Val Leu Gly Leu Val Leu Leu Ser Val Thr Val
1               5                   10                  15

Gln Gly Lys Val Phe Glu Arg Cys Glu Leu Ala Arg Thr Leu Lys Arg
                20                  25                  30

Leu Gly Met Asp Gly Tyr Arg Gly Ile Ser Leu Ala Asn Trp Met Cys
            35                  40                  45

Leu Ala Lys Trp Glu Ser Gly Tyr Asn Thr Arg Ala Thr Asn Tyr Asn
        50                  55                  60

Ala Gly Asp Arg Ser Thr Asp Tyr Gly Ile Phe Gln Ile Asn Ser Arg
```

```
                65                  70                  75                  80
Tyr Trp Cys Asn Asp Gly Lys Thr Pro Gly Ala Val Asn Ala Cys His
                85                  90                  95

Leu Ser Cys Ser Ala Leu Leu Gln Asp Asn Ile Ala Asp Ala Val Ala
               100                 105                 110

Cys Ala Lys Arg Val Val Arg Asp Pro Gln Gly Ile Arg Ala Trp Val
           115                 120                 125

Ala Trp Arg Asn Arg Cys Gln Asn Arg Asp Val Arg Gln Tyr Val Gln
           130                 135                 140

Gly Cys Gly Val
145

<210> SEQ ID NO 15
<211> LENGTH: 43
<212> TYPE: PRT
<213> ORGANISM: Homo sapiens

<400> SEQUENCE: 15

Asp Ala Glu Phe Arg His Asp Ser Gly Tyr Glu Val His His Gln Lys
1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40
```